(12) United States Patent
Mayer et al.

(10) Patent No.: US 11,253,732 B2
(45) Date of Patent: Feb. 22, 2022

(54) THERAPEUTIC ENERGY SYSTEMS

(71) Applicant: ENERGIZE MEDICAL LLC, Lenexa, KS (US)

(72) Inventors: Carl Mayer, Overland Park, KS (US); John Ellenz, Olath, KS (US)

(73) Assignee: Energize Medical LLC, Lenexa, KS (US)

( * ) Notice: Subject to any disclaimer, the term of this patent is extended or adjusted under 35 U.S.C. 154(b) by 170 days.

(21) Appl. No.: 16/277,825

(22) Filed: Feb. 15, 2019

(65) Prior Publication Data
US 2019/0247680 A1    Aug. 15, 2019

Related U.S. Application Data

(63) Continuation of application No. 14/494,603, filed on Sep. 24, 2014, now abandoned, which is a
(Continued)

(51) Int. Cl.
*A61N 7/02*    (2006.01)
*A61B 18/12*    (2006.01)
(Continued)

(52) U.S. Cl.
CPC .............. *A61N 7/02* (2013.01); *A61B 17/32* (2013.01); *A61B 18/1206* (2013.01);
(Continued)

(58) Field of Classification Search
CPC . A61B 18/1206; A61B 18/14; A61B 18/1477; A61B 2017/00482; A61B 2018/00178; A61B 2018/00648
See application file for complete search history.

(56) References Cited

U.S. PATENT DOCUMENTS

| 5,391,144 A | * | 2/1995 | Sakurai | ............ | A61B 17/22012 |
| | | | | | 604/22 |
| 7,582,055 B2 | * | 9/2009 | Komiya | ................ | A61B 1/018 |
| | | | | | 600/104 |

(Continued)

*Primary Examiner* — Linda C Dvorak
*Assistant Examiner* — Ryan T Clark
(74) *Attorney, Agent, or Firm* — The Fedde Law Firm; Kenton Fedde; Nathaniel Fedde

(57) ABSTRACT

The invention provides a therapeutic system comprising:
a console, wherein the console comprises a controller and an energy generator;
a therapeutic device comprising: an operational head configured for transmitting the energy output from to a biological tissue; and a memory device comprising control instructions, wherein said control instructions comprise instructions for controlling the console;
a reversible memory operable linkage linking the memory device to the controller; and
a reversible connector configured for operably linking the energy generator to the operational head.
Optionally, the energy generator is a generator of ablation energy or heat energy (e.g. RF generator) and the control instructions comprise instructions for controlling the output of the energy generator. Optionally, the control instructions comprise one or more parameters of energy output or an algorithm configured for controlling the energy output. Optionally, the system further comprises one or more secondary therapeutic devices and the control instructions comprise instructions for controlling the one or more secondary therapeutic devices. Optionally, the system further comprises one or more sensors configured for sensing parameters of energy output or biological or environmental effects of the energy output and the control instructions comprise instructions for controlling the energy output and/or secondary therapeutic devices based on the parameters of energy output or biological or environmental effects. In some embodiments, one advantage provided by the present inven-
(Continued)

tion is the use of a single console with a plurality of interchangeable reversibly connected therapeutic devices.

3 Claims, 13 Drawing Sheets

Related U.S. Application Data continuation of application No. PCT/US2013/056072, filed on Aug. 22, 2013.

(60) Provisional application No. 61/692,228, filed on Aug. 22, 2012.

(51) Int. Cl.
| | |
|---|---|
| *A61B 18/14* | (2006.01) |
| *A61N 1/44* | (2006.01) |
| *A61B 17/32* | (2006.01) |
| *A61M 16/14* | (2006.01) |
| *A61M 1/00* | (2006.01) |
| A61N 5/02 | (2006.01) |
| A61N 5/06 | (2006.01) |
| A61B 18/02 | (2006.01) |
| A61B 18/00 | (2006.01) |
| A61M 11/00 | (2006.01) |
| A61B 17/00 | (2006.01) |
| A61M 16/06 | (2006.01) |
| A61M 16/08 | (2006.01) |
| A61M 16/16 | (2006.01) |
| A61M 16/00 | (2006.01) |

(52) U.S. Cl.
CPC .......... *A61B 18/14* (2013.01); *A61B 18/1477* (2013.01); *A61M 1/84* (2021.05); *A61M 16/14* (2013.01); *A61N 1/44* (2013.01); *A61B 18/02* (2013.01); *A61B 2017/00482* (2013.01); *A61B 2018/0016* (2013.01); *A61B 2018/00178* (2013.01); *A61B 2018/00577* (2013.01); *A61B 2018/00648* (2013.01); *A61B 2018/00702* (2013.01); *A61B 2018/00821* (2013.01); *A61B 2018/00839* (2013.01); *A61B 2018/00863* (2013.01); *A61B 2018/00988* (2013.01); *A61B 2018/143* (2013.01); *A61M 11/00* (2013.01); *A61M 16/06* (2013.01); *A61M 16/0816* (2013.01); *A61M 16/0875* (2013.01); *A61M 16/16* (2013.01); *A61M 2016/0027* (2013.01); *A61M 2205/3569* (2013.01); *A61M 2205/3592* (2013.01); *A61M 2205/502* (2013.01); *A61M 2205/52* (2013.01); *A61M 2205/6018* (2013.01); *A61M 2205/70* (2013.01); *A61N 5/025* (2013.01); *A61N 5/06* (2013.01)

(56) References Cited

U.S. PATENT DOCUMENTS

| | | | |
|---|---|---|---|
| 2013/0053840 A1* | 2/2013 | Krapohl | A61B 18/1445 606/33 |
| 2015/0126998 A1* | 5/2015 | Batchelor | A61B 18/1445 606/42 |

* cited by examiner

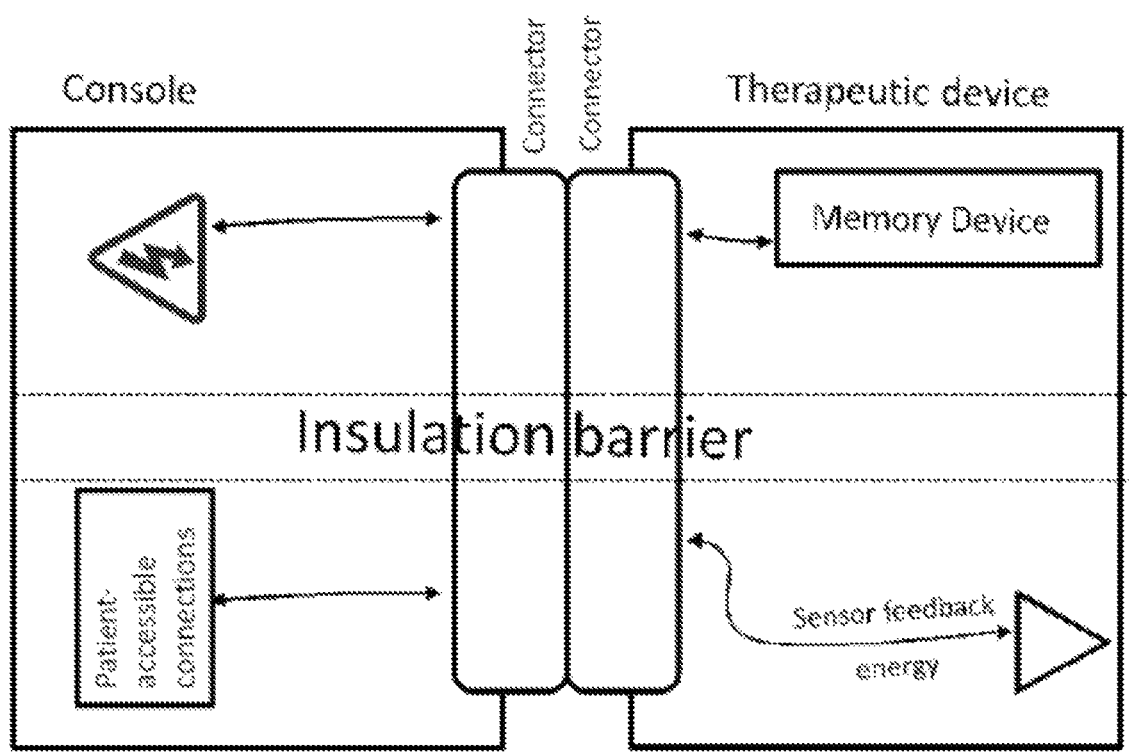

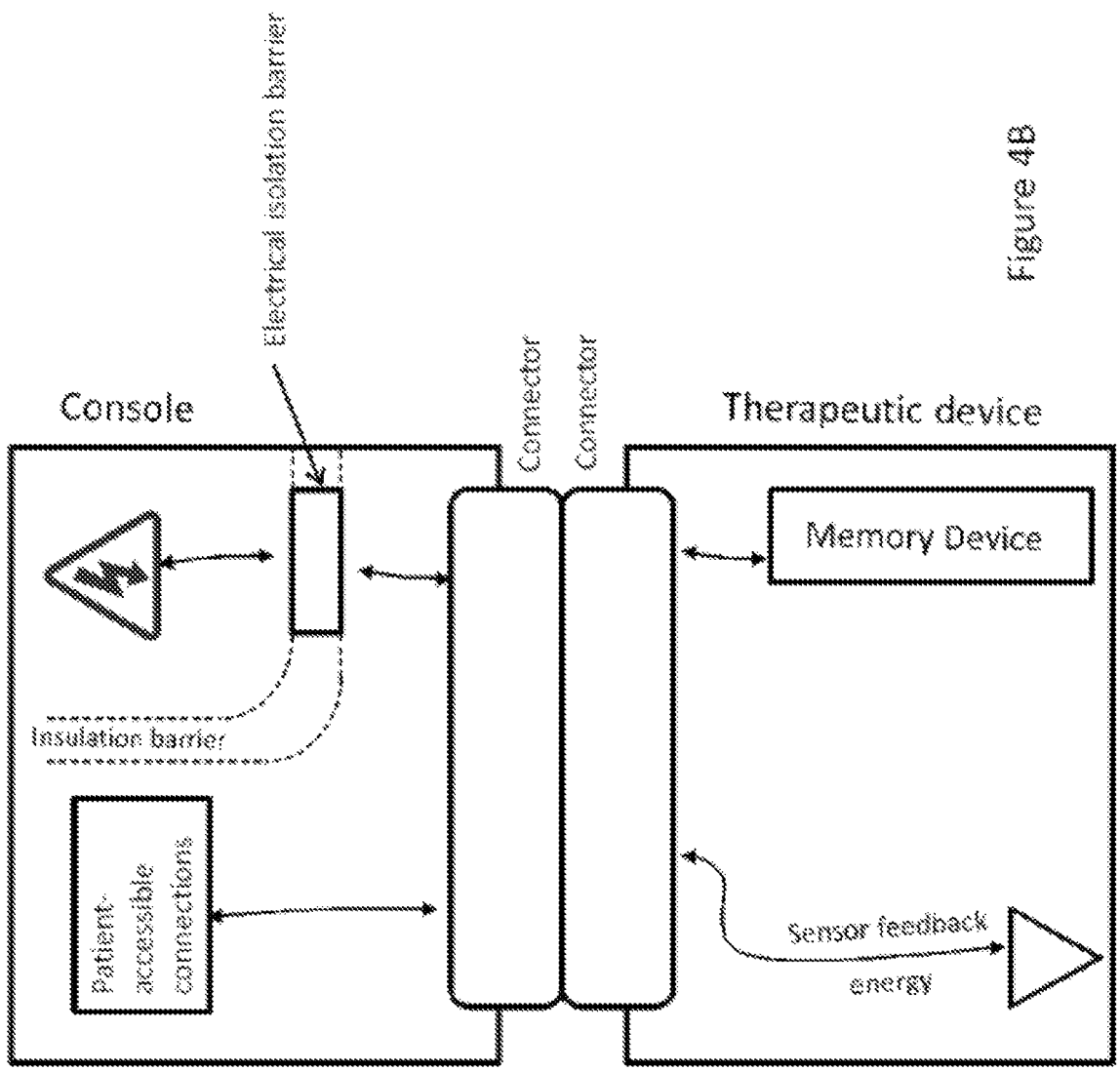

THERAPEUTIC ENERGY SYSTEMS

RELATED APPLICATIONS

This application is a continuation of U.S. application Ser. No. 14/494,603 filed 24 Sep. 2014, which is a continuation of International Application PCT/US2013/056072 filed 22 Aug. 2013 which claims the priority of U.S. Provisional Patent Application No. 61/692,228 filed 22 Aug. 2012, the contents of each of which are incorporated herein by reference in its entirety.

TECHNICAL FIELD

The present invention relates to therapeutic devices.

BACKGROUND

The delivery of radio frequency ('RF') energy to target biological tissue is known for a variety of purposes. In one particular application, RF energy is delivered for ablating the target tissue.

Conventional RF devices comprise a console (RF generator and controller) and a removable operational head (e.g. RF probe or RF catheter) configured for contacting the target tissue. A limitation of conventional RF devices is that each console is typically configured for only a limited number of operational heads. For example, at the time of purchasing new operational heads for a new technique, it is common to acquire, at the same time, a dedicated console. Consequently, there is a significant cost associated with purchasing, storing and maintaining a dedicated console for each of a large variety of operational heads. As an alternative, some consoles can accept a number of different operational heads; however, the controller must be re-programmed, re-calibrated or reset by the operator each time new unique operational head is introduced into the market or each time the operator wishes to change the output parameters of the generator.

Shah et al. (U.S. Pat. No. 7,258,688) describes one attempt to overcome these limitations by providing an RF generator that stores a plurality of operating modes specific to respective probe types. The RF generator further comprises an automatic probe type detector to enable the selection of the respective operating mode. Accordingly, the system described by Shah et al. is limited to probe types and modes pre-configured into the generator. Shah et al. do not teach storing the operating modes or control instructions on the probe.

Eubanks et al. (US 2011/0106004), describes interventional catheter assemblies, operating systems and adaptive interface components allow operation of a variety of interventional catheter assemblies, including infusion catheters, aspiration catheters and interventional catheters that provide both infusion and aspiration, using a common control console housing infusion and aspiration systems. Control instructions for operating the interventional catheter assembly and protocols for verifying system matches and operating conditions maybe encoded in hardware, firmware or software, such as a memory or storage device, provided in the interventional catheter assembly. Eubanks et al. fail to teach a catheter assembly comprising memory instructions for controlling user interface of a console. Further, Eubanks et al. fail to teach a catheter assembly comprising memory instructions for controlling RF output of a reversibly connected RF generator.

What is needed in the art is a flexible system enabling the use of a variety of different removable therapeutic devices with a common console.

SUMMARY OF THE INVENTION

The invention provides a therapeutic system comprising:
a console, wherein the console comprises a controller and an energy generator (e.g. RF generator); a therapeutic device comprising: an operational head configured for transmitting the energy output of the energy generator to the biological tissue; and a memory device comprising control instructions, wherein said control instructions comprise instructions for controlling the console ('control instructions');
a reversible memory operable linkage linking the memory device to the controller; and
a reversible connector configured for operably linking the energy generator to the operational head.

The control instructions can comprise instructions for controlling any component of the therapeutic system. Optionally, the control instructions comprise instructions for controlling the output of the energy generator (e.g. the control instructions comprise parameters of energy output such as RF output). Optionally, the system further comprises a secondary device (e.g. UI, sensor, or d/t device) and the control instructions comprise instructions for controlling the secondary device. Optionally the console comprises a user interface ('UI') and the control instructions comprise instructions for controlling the UI (e.g., the control instructions for displaying limits of operation, therapy transition criteria, or parameters such as sensed parameters or parameters stored on the memory device. Optionally, the control instructions that are operating head-specific, clinician-specific, or patient-specific).

Optionally, the control instructions comprise at least two sets of alternatively selectable control instructions (e.g. alternative instructions for controlling the energy output), for example, a first set configured for a first procedure and a second set configured for a second procedure.

Optionally, the energy generator is an RF generator, an ultrasound generator, a microwave generator, or a laser generator.

Optionally, the reversible connector comprises the reversible memory operable linkage, e.g. a wired communications linkage. Alternatively, the reversible memory operable linkage comprises a wireless communications linkage (e.g. electromagnetic or optical).

Optionally, the energy generator is an RF generator or other electromagnetic energy generator and the control instructions comprise one or more parameters of RF output or other energy output. Optionally, the one or more parameters of RF output or other energy output comprise one or more of: voltage, current, temperature, stimulation rate, pulse rate, pulse duration, ramp time, frequency, waveshape, and power.

Optionally, the system further comprises one or more sensors. Optionally, the reversible connector is configured for operably linking the one or more sensors to the controller. Optionally, the one or more sensors are configured for sensing or monitoring ('monitoring') one or more parameters. Optionally, the one or more parameters are selected from: an energy (e.g. RF) output parameter, an environmental condition, a biological condition), a therapeutic device condition (e.g. user input condition such as button, indicator, lever, or switch status). Optionally, the control instructions comprise instructions for controlling the sensor and/or for controlling the RF output (e.g. modulating RF output differentially) based on the monitored one or more parameters.

Optionally, the therapeutic device comprises an energy delivery head and at least one additional therapeutic head. Optionally, the control instructions further comprise instructions for controlling the at least one additional therapeutic head. Optionally, the at least one additional therapeutic heads are selected from: an irrigation head (e.g. cannula or lumen for connection to a fluid pump), an aspiration head (e.g. cannula or lumen for connection to a fluid pump), a lighting head, an expandable device, a cutting head, and one or more RF heads.

Optionally, the control instructions comprise one or more parameter values or one or more algorithms, e.g. for conducting a therapeutic procedure or otherwise controlling connected devices or providing instruction.

Optionally, the control instructions comprise one or more parameters selected from energy output parameters, UI output parameters, calibration parameters, verification parameters, capability parameters, and input parameters.

Optionally, the memory device is proximal to the reversible connector. Optionally, the memory device and the operable linkage share a common housing (e.g. plug housing).

Optionally, the operational head is an RF ablation head. Optionally, the RF ablation head is a nerve ablator.

Optionally, the therapeutic device comprises one or more of: a needle, a probe, a catheter, a patch, and a handpiece.

Optionally, the operational head is configured for connection to or insertion into a patient. Optionally, the operational head comprises a needle, a blade, a patch, a cutting wire, an application plate, a catheter, or a probe.

Optionally, the therapeutic system comprises a plurality of said therapeutic devices, wherein each therapeutic device is connected to a console by an independent reversible connector and each therapeutic device comprises a memory device reversibly linked to the console. Optionally, the second therapeutic device comprises a second memory device comprising control instructions, wherein said control instructions comprise instructions for controlling the second therapeutic device. Alternatively, a memory device of a first therapeutic device optionally comprises instructions for controlling a second therapeutic device of the system. Optionally, the second therapeutic device and the first therapeutic device share an operational head or comprise operational heads comingled together. Optionally, the second therapeutic device is a fluid pump.

The invention also provides a therapeutic method using a system of the present invention.

The invention also provides a device family comprising said system and a plurality of additional therapeutic devices, each comprising a unique set of control instructions. The invention also provides a method of a) selecting a first therapeutic device from the plurality; b) connecting the first therapeutic device to the console, c) performing a first therapeutic procedure with the first therapeutic device, d) removing the first therapeutic device from the console, and e) repeating steps a)-d) using a second therapeutic device of the plurality.

BRIEF DESCRIPTION OF THE DRAWINGS

FIGS. 4A and 4B depict examplary therapeutic devices useful in the present invention.

DETAILED DESCRIPTION OF THE INVENTION

Figure 1A:
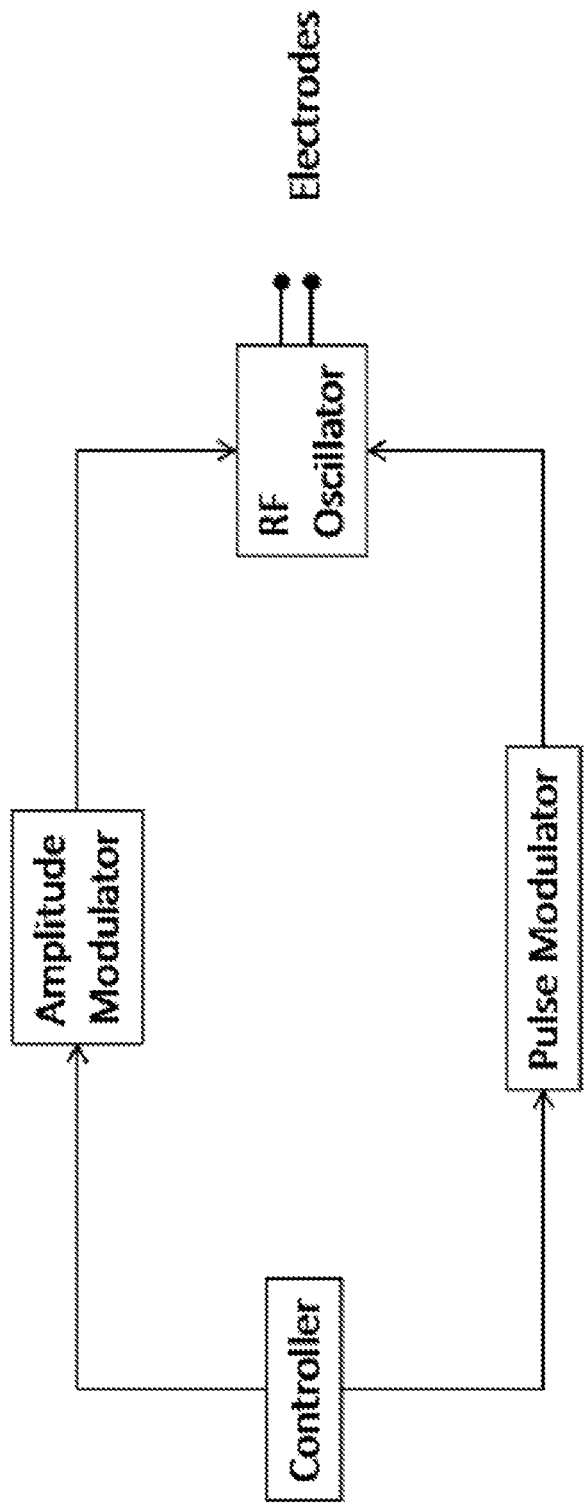
FIGS. 1A and 1B depict examplary RF generators useful in the present invention.

As used here, the following definitions and abbreviations apply.

"Examplary" (or "e.g." or "by example") means a non-limiting example.

"Non-volatile memory" means memory that does not require power to retain stored information. Optionally, the memory device of the therapeutic device comprises non-volatile memory.

"Volatile memory" means memory requires power to retain stored data.

Optionally, the memory device of the therapeutic device comprises volatile memory and the therapeutic device comprises a battery configured for powering the memory device. The battery is optionally configured for continuously powering the memory device when the therapeutic device is not in use or not connected to the RF generator.

"Controlling" means affecting the behavior and/or appearance of a system or a system component or the resulting outcome produced by that system or system component. Examples of optional system components include UI (e.g. display such as a screen or an input such as a button), energy generators, operating heads (e.g. RF head), sensors, and any device connected to the console or therapeutic device. As another example, controlling a sensor can comprise receiving feedback from the sensor and affecting the behavior of another component based on said feedback.

Connector

According to the present invention, at least one connector is provided for reversibly connecting a therapeutic device to a console. Such a reversible connector can be configured in any manner that provides an operable linkage between the console (or component thereof) and the therapeutic device (or component thereof) upon connection of the therapeutic device to the console using the connector. The connector is configured to provide an operable linkage between the energy generator of the console and the operational head of the therapeutic device, thus providing a reversibly connected therapeutic device. Optionally, the system comprises one or more additional connectors for reversibly connecting one or more devices (e.g. a secondary device) to the console, e.g. by linkage directly to the console (e.g. to any console component) or by indirect linkage to the console (e.g. by linkage to a second console or other device that is itself linked to the first console, e.g. by a communications link). Optionally, a connector used in the invention is configured to provide a plurality of operable linkages, e.g. any two, three or four members of the group consisting of a first energy linkage, a second energy linkage, a memory linkage, and a sensor linkage.

Optionally, the connector comprises interacting couplers, at least one on the console side ('console-side connector') and at least one on the therapeutic device side ('therapeutic device-side connector'), or in the case of a secondary device, on an optional secondary device side ('secondary device-side connector'). Examples include a jack/plug configuration, e.g. wherein a plug is provided on the therapeutic device or a secondary device and a respective the jack is provided on a console. In this configuration, a system is optionally provided with at least console having a jack and a plurality of therapeutic devices, each having a plug that interacts with the jack, e.g. to provide interchangeable therapeutic devices. Similarly, such interacting couplers can optionally be provided to connect interchangeable secondary devices to a console.

Optionally, the connector comprises a plurality of terminals, e.g. a pin connector. Optionally, the connector is configured to simultaneously operably link a plurality of components of the therapeutic device with the console upon connection of the connector. For example, the connector can be configured to simultaneously connect at least one energy delivery terminal, sensory linkage terminals, and optionally memory linkage terminals.

Optionally, the connector comprises an operable linkage (e.g. electrical terminals for conducting RF output) connecting the energy generator to one or more electrodes of the operational head of the therapeutic device.

Optionally, the connector comprises an operable linkage (e.g. communication bus) connecting the controller of the console to the memory device of a therapeutic device.

Optionally, the connector comprises an operable linkage (e.g. electrical terminals) connecting an optional power source such a DC source, an AC source, or an AC/DC transformer of the console to one or more components (e.g. memory device) of the therapeutic device.

Optionally, the connector comprises an operable linkage (e.g. cannula or tubing set) connecting an optional fluid pump of the console with a secondary device head (e.g. aspiration or infusion port) of the therapeutic device.

Optionally, the connector comprises one or more cannulas. Optionally, the cannulas are configured to conduct a fluid such as a gas or liquid, or to deliver to a subject a device such as a stent or an implantable device.

The connector is not limited to a connector having a particular type of operable linkage. Any operable linkages are useful in connectors. The configuration of operable linkages will, of course, depend on the nature of the component operably linked through the connector. For example, electrically conductive terminals can be used to provide operable linkages for connection one or more of: an RF generator, a controller, a power source, data communication connections or a display. As another example, a cannula can be provided as operable linkage to a fluid pump. The skilled artisan will recognize other operable linkages useful in the present invention.

Optionally, a therapeutic device side connector or a secondary-device side connector comprises a memory device. Optionally, the therapeutic device side connector or a secondary-device side connector, or memory device thereof can be detached from the therapeutic device or secondary device. Such embodiments allow, for example, a user to easily remove the memory device from the therapeutic device and send the memory device (e.g. ship a small, lightweight memory device) to a second party (e.g. manufacture) for inspection or retrieval of data (e.g. a procedure log recorded on the memory device)

Optionally, the connector comprises interacting couplers, at least one on the console side and at least one on the therapeutic device side, wherein the interacting couplers are configured to provide one or more of:
- a. Feedback of connection status such as tactile feedback (e.g. "snap" upon successful connection) or illumination feedback (e.g. light upon successful connection);
- b. magnetic coupling (e.g. magnets of opposite polarity placed on the console side and therapeutic device side);
- c. visual alignment (e.g. marks on the console side and therapeutic device side that align upon successful connection);
- d. mechanical alignment and coupling (e.g. male/female couplers);
- e. thermal reference for temperature sensing;
- f. thermal coupling;
- g. fluid alignment;
- h. a locking mechanism; and
- i. a reuse control mechanism Console A system of the present invention comprises at least one console comprising an energy (e.g. RF) generator and a controller, wherein the console is configured for accepting the connector for operably linking a therapeutic device to the console.

Optionally, the console further comprises a user interface ('UI'). Optionally, the user interface comprises a display and/or a user input device.

Optionally, the console further comprises a display. Optionally, the display is a screen, e.g. LCD screen or projector (e.g. pico-projector).

Optionally, the console further comprises a user input device. Optionally, the user input device comprises one or more of: a keyboard, keys, a touch-screen, a switch, a wheel, a mouse, voice and audio recognition device, foot switch, hand control, retinal scanner, a clapper and a dial.

Optionally, the console further comprises a housing. Optionally, the housing is configured for accepting the connector (e.g. comprises a jack for the connector). The housing optionally encloses one or more of: the RF generator, the controller, a display, and a user input device.

Optionally, the console further comprises a power supply. Optionally, the power supply is a battery or an AC/DC transformer.

Optionally, the console further comprises a local memory device (also referred to herein as 'console memory').

Optionally, the console is a computer. Optionally, the computer comprises
- a. a processor, e.g. microprocessor configured for use as the RF generator controller or a microprocessor in communication with the RF generator controller;
- b. a local memory device;
- c. a connector configured for connection to the connector of the therapeutic device; and
- d. a structure (e.g. a motherboard or other circuit board) configured for operably linking the processor to the other components of the computer (e.g. local memory device, RF generator, and connector).

Examplary consoles of the present invention are configured to provide one or more of the following functions:
- a) Attachment to (e.g. through a connector) a removable therapeutic device, such as a needle, probe, catheter, patch, handpiece, wire, plate, mesh, balloon through which energy such as RF energy is applied to a patient;

b) Delivery of a range of therapeutic energies to a patient via the therapeutic device;
c) Monitoring a plurality of energy monitoring, biological, physiological, physical and environmental parameters relevant to the patient's treatment and convert these into computer-readable data;
d) Providing a user input device to the operator to initiate, alter, or halt the delivery of energy such as RF energy to the patient;
e) Providing a user interface (e.g. text, graphics, and/or sounds) that presents feedback to the operator regarding the status of energy delivery and the monitored parameters;
f) Starting, stopping, or changing energy delivery based on the monitored parameters;
g) Providing warning, alerts, alarms, or other advice to the operator based on the monitored parameters; and
h) Reading data stored in the memory of an attached therapeutic device;

In one embodiment, the invention provides a system comprising a plurality consoles connected by a data link between controllers ('communications link'). Optionally, the plurality at least comprises a first console configured to provide a first medical function (e.g. diagnostic or therapeutic function) and a second console configured to provide a second medical function. The medical functions are optionally any medical functions provided by a d/t device (e.g. therapy such as energy delivery or sensing such as imaging) Each of the first and second consoles are optionally reversibly or non-reversibly connected to a d/t device such as a therapeutic device or diagnostic device for control thereof. The controllers of the first and second consoles can be configured to provide coordinated medical functions, for example, by providing control instructions on memory such as console memory or therapeutic device memory of a connected therapeutic device. The first and second medical functions are each optionally a therapeutic function (e.g. energy generation) or a diagnostic function (e.g. imaging). Optionally, at least the first console is reversibly connected to a therapeutic device. Optionally, the second console is reversibly connected to a therapeutic device or a diagnostic device. Examples of useful console combinations include ablation/irrigation, ablation/imaging (e.g. as detailed in Example 18), and vaporization/ventilation (e.g. as detailed in Example 16).

Energy Generator

A system of the present invention comprises at least one energy generator configured for control by a controller. Useful energy generators include any generator of therapeutic energy or diagnostic energy.

Optionally, the system comprises an energy generator configured to provide a therapeutic energy selected from electromagnetic energy, mechanical energy, thermal energy, and electrical energy.

Optionally, the system comprises an energy generator configured to provide electromagnetic energy selected from RF energy, microwave energy, and light energy (e.g. laser).

Optionally, the system comprises an energy generator configured to provide mechanical energy selected from irrigation (e.g. fluid pump for cooling), pneumatic pressure (e.g. ventilator for ventilation, compression sleeve), inert gas pressure (e.g. insufflation) and sonic energy (e.g. ultrasound generator for therapy).

Optionally, the system comprises an energy generator configured to heat or ablate a target biological tissue. For example, the system can comprise an RF generator, an ultrasound generator, a microwave generator, a cryoablation generator, or a laser generator.

Optionally, the system comprises an energy generator configured to produce diagnostic energy. Examples of useful diagnostic energy include imaging energy such as an electromagnetic imaging energy. Useful imaging energies include magnetic energy or RF imaging energy (e.g. as in an MRI device) and X-ray energy (e.g. as in CAT, PET, and fluoroscopy devices).

Optionally, the system comprises an RF generator. The RF generator can comprise any RF energy source. Optionally, the RF energy source is an RF oscillator. The RF generator can be configured to produce any RF energy. Optionally, the RF energy is ablation energy or cutting energy.

Optionally, the RF generator is configured for producing RF energy at a plurality of frequencies, amplitudes, crest factors, and/or pulse characteristics.

Optionally, the RF generator comprises one or more RF modulators, e.g. an amplitude modulator, a pulse modulator, and/or a frequency modulator.

Optionally, the RF generator is configured for operating in a frequency range of about 80 kHz to about 15 MHz.

Optionally, the RF generator is configured to operate in a sinusoidal or a non-sinusoidal wave form.

Optionally, the RF generator is configured to operate with a power output in the range of about 1 W to about 500 W.

Optionally, the RF generator comprises a plurality of output channels. Additionally or alternatively, the console comprises a plurality of RF generators.

An examplary RF generator useful in the present invention comprises an RF energy source such as an RF oscillator, wherein the RF generator is configured for amplifying and modulating the RF energy. The RF generator is configured for producing RF energy at a plurality of frequencies, e.g. by providing an RF oscillator with variable frequency output or by providing an RF frequency modulator coupled to the RF oscillator. The generator can be configured, e.g. as depicted in FIG. 1A or B.

The RF generator can be controlled by any controller. Optionally, the controller of the RF generator is the same controller that communicates with the memory device of a connected therapeutic device. Alternatively, the controller of the RF generator is optionally configured to be in communication with a one or more controllers configured to access the memory device of a therapeutic device.

Controller

A system of the present invention comprises at least one controller configured to:
 a. access data stored on a memory device (e.g. memory device of a connected therapeutic device), wherein the data comprises control instructions; and
 b. control at least one console component (e.g. energy generator) according to the control instructions.

Any controller is useful in the present invention. Optionally, the controller comprises a microcontroller such as a microprocessor. Other useful controller types include reconfigurable logic devices such as FPGA, CPLD, special-purpose computing engines such as graphics processing units (GPU), process controllers such as a PLC, and operational amplifier circuits, etc.

In general, the controller can be configured to control (i.e. send data or analog signals to and/or receive data or analog signals from) input or output ('I/O') devices of the system such as the energy (e.g. RF) generator; the memory device of the therapeutic device (also referred to herein as 'therapeutic device memory' or the 'memory device'); and optional devices of the system such as a sensory- or therapeutic-type device (e.g. fluid pump or an additional energy generator), a local memory device ('local memory'), a user interface (e.g. user input device and/or user output device).

The controller can optionally be a single controller connected to and configured to control the I/O devices or, or alternatively, can comprise a collection of controllers in communication with each other or with a common controller. Optionally, the controller comprises two or more independent controllers selected from: an energy (e.g. RF) generator controller, a memory device controller, a serial or parallel device controller, and a display controller. Optionally, the controller comprises a primary controller (e.g. microprocessor such as those used in desktop computers) and one or more secondary controllers, wherein each of the one or more secondary controllers is controlled by the primary controller and in-turn controls a console device (e.g. energy generator controller).

Optionally, the controller is configured for controlling a user interface. Optionally, the user interface comprises an output device and/or an input device. Examples of useful output devices include a graphic user interface ('GUI') or a non-graphical user interface such as an LED or text-based display.

Optionally, the controller is configured for controlling a display (e.g. screen).

Optionally, the controller is configured for controlling an input device. Examples of useful input devices include a user input device and a sensor. The controller can control an input device, e.g. by receiving data or feedback (e.g. analog electrical feedback such as voltage or resistance induced by a temperature sensor or other input device) and performing a designated function (e.g. controlling another component or computing a sensed condition such as temperature).

Optionally, the controller is configured for controlling a user input device. Examples of user input devices include key-type inputs (e.g. keyboard), mouse, footswitch, and touchscreens.

Optionally, the console comprises memory local to the controller. The memory can be configured to provide one or more or all of the following:
  a) Basic operating-system services such as storing files, creating standard interfaces, executing programs.
  b) Low-level control and monitoring of Therapeutic RF or other energy delivery.
  c) Low-level control and monitoring of the monitored parameters.
  d) Display text and images to the display.
  e) Sound audio from speakers.
  f) Communicate with standard networking and communication interfaces such as Ethernet, USB, Firewire.
  g) Export patient and treatment history information to networking interfaces.
  h) Export patient and treatment history information to operator-removable mass storage devices such as a USB Mass Storage device.
  i) Export patient and treatment history information to printers.
  j) Add, replace, or modify software or control instructions contained one the memory of the therapeutic device.
  k) A framework for retrieving an algorithm or parameter from the therapeutic device and executing the algorithm to control the operation of the console or therapeutic device (e.g. configuration management software, or a script interpreter).

Energy Generator Control

According to the present invention, at least one controller is configured to control the output of the energy (e.g. RF) generator according to the control instructions on the memory device of a connected therapeutic device.

Optionally, the controller is configured to control one or more energy (e.g. RF) output parameters selected from: pulse parameters (e.g. pulse duration and/or pulse frequency), amplitude, energy frequency, and wave shape. Optionally, the value of the one or more energy (e.g. RF) output parameters is obtained from the memory device.

Optionally, the controller is configured to modulate the output of an RF energy source. Optionally, the controller is configured to control a modulator of RF output. Optionally, the modulator is selected from an amplitude modulator, a pulse modulator, a frequency modulator, or a combination thereof. Alternatively, the controller is optionally configured for modulating an energy source of the energy generator, e.g. to produce a modulated waveform directly. Optionally, the controller is configured to obtain control instructions for said modulating from the memory device.

Optionally, the controller is configured to carry out an algorithm comprising a plurality of steps, wherein at least one of the steps comprises controlling the energy (e.g. RF) generator. Optionally, the algorithm, or portion thereof, is stored on and obtained from the memory device. Alternatively, the algorithm is optionally stored locally and comprises one or more variables (e.g. parameter variables), wherein the values of the one or more variables are obtained from the memory device.

Optionally, the controller is configured for carrying out an algorithm, wherein the algorithm or portion thereof is stored on the memory device of a connected therapeutic device. Optionally, at least one of the steps comprises controlling the energy (e.g. RF) generator.

Optionally, the controller is configured for carrying out an algorithm stored locally, wherein the algorithm comprises one or more variables (e.g. parameter variables), wherein the values of at least one of the one or more variables are stored on the memory device. The controller is configured to obtain the values from the memory device and set the variables using the values.

Optionally, algorithms carried out by the controller comprise a plurality of steps, including therapeutic steps and optional sensing steps, wherein at least one of said steps comprises controlling the energy (e.g. RF) generator.

Optionally, instructions for controlling the energy generator are provided on a memory device of a reversibly connected therapeutic device.

Memory Device Control

According to the present invention, at least one controller is configured for accessing data stored on the memory device of a connected therapeutic device.

Optionally, the controller is configured to obtain control instructions from the memory device, e.g. a set of parameter values, one or more algorithms, or a combination thereof.

Optionally, the controller of the console is configured to directly access a memory device of a connected therapeutic device (e.g. the connector provides operable linkage directly to console controller from the memory device). Alternatively, the therapeutic device optionally comprises an independent controller configured to access the memory device and communicate data therefrom to the controller of the console (e.g. the connector provides operable linkage to console controller from a controller of the memory device).

Optionally, instructions for controlling the memory device of a therapeutic device are provided on a local memory device.

User Output Control

Optionally, at least one controller is configured for controlling a user output graphic interface. Optionally, the controller comprises one or more independent user output controllers (e.g. graphics microprocessor) for controlling the user output.

Optionally, the user output comprises one or more of: a speaker, a graphic interface. Optionally, the graphic interface is a display, a projector, a screen, or a device comprising one or more LEDs, LCDs, CRTs, or VFDs.

Optionally, the controller is configured to display data stored on the memory device of the therapeutic device. Optionally, the displayed data comprises one or more of: ID code or identifier of the therapeutic, manufacture date of the therapeutic device, expiration date of the therapeutic device, use data of the therapeutic device, settings adjusting the energy delivery or treatment, or control instructions (e.g. parameter values).

Optionally, the controller is configured for controlling a user output based on the control instructions of the memory device. For example, the control instructions can be configured to specify a parameter of user output such as text size, graph axes, update rate, filtering, color, units of values, precision of values, acceptable ranges of values, and value or conditioning of sensor signals to trigger alarms or alerts. Additionally or alternatively, the control instructions can comprise a trigger parameter (e.g. temperature, ECG, or heart rate) which triggers a step of controlling (e.g. displaying or alerting via) the user output device.

Optionally, the controller is configured for displaying a real-time report or a post-procedure report, e.g. a report of any of: parameters stored on the memory device or sensed parameters or energy output parameters encountered during a therapeutic procedure.

Optionally, the controller is configured for presenting (e.g. visually or audibly) input sensed during a therapeutic procedure.

Optionally, instructions for controlling the user output device are provided on a memory device of a reversibly connected therapeutic device.

User Input Device Control

Optionally, at least one controller is configured for controlling a user input device. Optionally, the user input device comprises a one or more of: a keyboard, keys, a touchscreen, a switch, a wheel, a mouse, voice and audio recognition device, foot switch, hand control, retinal scanner, a clapper and a dial.

Optionally, the user input device is provided on the console or on the therapeutic device.

Optionally, instructions for controlling the user input device are provided on a memory device of a reversibly connected therapeutic device.

Secondary Device Control

Optionally, the controller is configured to control one or more secondary devices. Useful secondary devices include any device that provides a sensory function (e.g. temperature sensor, force sensor, or imaging device) or therapeutic function (e.g. irrigation).

The controller can be configured to control one or more secondary devices in any manner. Optionally, the controller is configured to obtain control instructions for controlling the secondary device from the memory device of the therapeutic device. Optionally, the memory device of the therapeutic device comprises instructions for controlling an energy generator and instructions for controlling a secondary device. Optionally, the control instructions comprise an algorithm comprising at least one step of controlling the secondary device and at least one step of controlling the energy generator. Optionally, at least one of said steps is dependent on at least one other step (e.g. controlling irrigation dependent on temperature, or controlling an energy generator dependent on temperature or contact force).

Optionally, the one or more secondary devices comprise a sensor (e.g. environmental sensor such as a temperature sensor or ECG) and controlling the sensor optionally comprises obtaining feedback from the sensor.

Optionally, the one or more secondary devices comprise a secondary therapeutic device (e.g. fluid pump or expandable device) and controlling the secondary therapeutic device comprises initiating, terminating, or modulating output of the secondary therapeutic device.

Therapeutic Device

According to the present invention, a therapeutic device can be connected to a console to operate the therapeutic device. The therapeutic device comprises an operational head, a memory device, and a therapeutic device-side connector for operable linkage to a console-side connector. Optionally, the therapeutic system comprises a plurality of therapeutic devices, each with a different operational head.

Optionally, the therapeutic device comprises one or more secondary devices (e.g. a sensor or a device with a therapeutic function).

Optionally, the therapeutic device comprises a connecting cable connecting the operational head to the connector.

Operable Linkage

According to the present invention, the therapeutic device is operably linked to a console. Components of a therapeutic device (e.g. the operational head and the memory device) can be operably linked to the console in any manner that allows control of the components by the console. Accordingly, a system of the invention comprises, as operable linkages, at least one communications linkage (e.g. memory operable linkage for transmitting data from a memory device) and at least one energy linkage (e.g. wires for transmitting RF energy).

Optionally, the operable linkage further comprises one or more of: an electrical power linkage, a mechanical linkage, and a secondary device linkage.

Optionally, the operable linkage comprises an electrical power linkage. For example, operational heads which require electrical power can be connected to the console via electrical wiring of the therapeutic device operably linked through the connector. Alternatively, operational heads which require electrical power can comprise a battery and a communications linkage to the console.

Optionally, the energy linkage is configured for transmitting energy selected from RF energy, ultrasound energy, laser energy, and microwave energy.

Optionally, the communications linkage comprises any wired or wireless linkage configured for transmitting data to or from the operational head or the memory device of the therapeutic device. For example, a wired communications linkage can be provided in the connector of the therapeutic device, or alternatively, the console and the therapeutic device can each comprise a wireless transmitter or receiver configured to communicate with each other (e.g. electromagnetic linkage based such as Bluetooth communications linkage or optical linkage)

Optionally, the operable linkage comprises a mechanical linkage. The mechanical linkage can be any linkage that imparts movement at the operational head by a driver (e.g. motor, solenoid, piezo transducer, cylinder, pneumatic pump or fluid pump) optionally provided in the console. Optionally, the mechanical linkage is provided through the connector of the therapeutic device. Optionally, the mechanical linkage comprises a cannula (e.g. for conducting a fluid as in aspiration or infusion or to power hydraulically powered instruments), or one or more levers, gears, cams, cranks, springs, belts, or wheels.

Optionally, the operable linkage comprises a secondary device linkage. The secondary device linkage can be any linkage configured to allow control of a secondary device. Optionally, the secondary device linkage comprises a therapeutic device linkage or a sensory device ("sensor") linkage. For example, one embodiment provides a therapeutic device comprising a sensor (e.g. temperature sensor), and the therapeutic device comprises a sensory device linkage configured to transmit feedback from the sensor (e.g. electrical wires for electrical current- or voltage-based feedback).

Operational Head

A therapeutic device useful in the present invention comprises one or more operational heads. The operational head is any component that is operably linked to the console and interacts with (e.g. contacts) a patient to provide a therapeutic or sensory function. According to the present invention, the therapeutic system comprises at least one therapeutic device comprising an operational head, wherein the operational head comprises an energy (e.g. RF) delivery head as an operational head.

Optionally, the energy delivery head is selected from: an RF head, an ultrasound head, a laser head, and a microwave head. Optionally, the energy delivery head is an RF head comprising one or more RF electrodes.

Optionally, the operational head comprises a secondary device, e.g. a sensor, a device with a therapeutic function, or a combination thereof.

Optionally, the operational head (e.g. RF head) comprises one or more of: a catheter, a hand tool, forceps, a needle, a probe, a plate, a blade, and a wand.

Optionally, the therapeutic device comprises at least one therapeutic head selected from: a second energy delivery head (e.g. RF ablation head), an expandable device, an aspiration or infusion head, a compression head, an irrigation head, a lighting instrument, a medication head, a cauterizing head, a saw, and a blade.

Optionally, the therapeutic device comprises an irrigation head. Optionally, the irrigation head is a closed irrigation loop head or an open irrigation head. Optionally, the therapeutic device comprises a singly maneuverable device comprising an energy delivery head and an irrigation head (e.g. an irrigated ablation catheter such as an open-loop or closed irrigation catheter).

Optionally, the therapeutic device comprises at least one sensory head (e.g. a sensor configured to sense an environmental effect at a target site or a biological effect on a patient). For example, the at least one sensory head can comprise a sensor of any parameter taught herein, e.g. a sensor of energy (e.g. RF) output, a sensor of an environmental condition (e.g. temperature or humidity), a biological signal (e.g. respiration, ECG or EMG), or a force sensor (e.g. contact force sensor of energy delivery head).

Optionally, the therapeutic device comprises at least one sensory device ('sensor') selected from: a temperature sensor, a heart rate sensor, an EMG head, an ECG head, a pressure sensor, a voltage sensor, an imaging head, a current sensor, an impedance sensor, a sensor of RF output (e.g. any RF output parameter), a chemical sensor, a fluid flow sensor, imaging sensor within a balloon catheter (e.g. fiber optic imager). Useful sensory signals can be provided about (e.g. in or on) an energy delivery head (e.g. temperature sensor in the tip of an ablation catheter) or provided on a separate operational head (e.g. a heart rate sensor in a location remote to an ablation catheter).

Optionally, the therapeutic device comprises a temperature sensor. Examples of useful temperature sensors include thermistors, resistance temperature detectors (RTD), and thermocouples. A temperature sensor can be operably linked to the console controller, e.g. by a pair of wires. Optionally, through such a temperature sensor linkage, the controller can receive feedback from the temperature sensor indicative of the temperature, e.g. temperature-dependent voltage of a thermocouple or temperature-dependent resistance of a thermistor. Optionally, a temperature sensor is provided about an energy delivery head (e.g. in an ablation catheter). Optionally, the therapeutic device comprises an RF head, at least one sensory device configured for monitoring an environmental condition and at least one sensory head configured for monitoring RF output.

Optionally, the operational head is configured for insertion into a subject. For example, the operational head can comprise a catheter, tube, introducer, or a needle configured for contact with or insertion into a subject.

Optionally, the therapeutic device comprises one or more therapeutic heads selected from: an RF head, an expandable device (e.g. balloon), an aspiration or infusion head, an irrigation head, a lighting instrument, a medication head a cauterizing head, a saw, and a blade.

Optionally, the operational head comprises a therapeutic head and a sensory head (e.g. a temperature sensor, force sensor, or both). Optionally, the operational head comprises an energy delivery (e.g. RF) head and an irrigation head. Optionally, the operational head comprises an energy delivery (e.g. RF head), an irrigation head, and a sensory head. For example the operational head can be an irrigated catheter (e.g. open loop or closed loop) comprising an energy delivery (e.g. RF) electrode on the outer tip of the catheter and optionally one or more sensors in or on the catheter tip.

Optionally, the therapeutic device comprises a plurality of operational heads joined or formed together as a single device that can be maneuvered into contact with a patient. For example, a plurality of therapeutic heads and/or sensors (e.g. an energy delivery head, an irrigation head, and a temperature sensor can be combined into a single maneuverable device (e.g. catheter).

Examples of useful operational heads such as energy delivery catheters and useful combinations of heads (e.g. energy delivery, sensory, and irrigation) are taught by U.S. Pat. Nos. 5,913,856, 7,591,816, US 20030004506, and U.S. Pat. No. 6,210,406.

RF Head

According to the present invention, the therapeutic device optionally comprises an RF head as an operational head. The RF head can be any device that transmits radio frequency energy from a connected RF generator to a subject. Exemplary RF heads of the present invention comprise an RF heating heads such as an RF ablation head, an RF fulguration head, an RF coagulation head, or RF cutting head.

Optionally, the RF head comprises one or more electrodes operably linked (e.g. electrically linked) to an RF generator of the console for delivering RF energy from the RF generator to tissue. Optionally, the RF head is a monopolar head, a bipolar head or a combination of both (e.g. phased array).

Optionally, the RF head is a thermal RF head. The thermal RF head can be any RF head configured to deliver RF energy having a heating effect, for example configured to cause ionic agitation, or friction, increasing the temperature of a target material. For example, the RF head can be configured to heat tissue or other materials. Optionally, the thermal RF head is any of: an RF ablation head, an RF cutting head, or an RF coagulation head.

Optionally, the RF head is a RF ablation head. The RF ablation head can be any RF head configured to deliver RF energy having an ablating effect.

Optionally, the RF head comprises a catheter, a hand tool, forceps, a needle, or a wand.

Optionally, the RF head comprises a catheter. An RF catheter can comprises, for example, a cannula with an RF electrode exposed at the tip. Useful RF catheters are taught, for example, by U.S. Pat. Nos. 5,913,856, 7,591,816, US 2003/0004506, and U.S. Pat. No. 6,210,406.

RF heads such as RF ablation heads can be configured in any manner. For example, an RF head can comprise at least two electrodes: a transmitting electrode for delivering energy and a return electrode for the return of the energy. The RF head can be configured as a monopolar head or a bipolar head. A monopolar RF head comprises a transmitting electrode configured for placement in proximity to a target tissue and a return electrode (sometimes referred to as an indifferent electrode) configured for placement distally to the target tissue (e.g. placement on the patient's skin, e.g. using a skin patch electrode). A bipolar RF head can comprise a transmitting electrode and a receiving electrode both in proximity to the target tissue. A head may optionally contain a plurality of electrodes which alternate polarity, phase, or connectivity to provide selective treatment.

Electrodes of an RF head can be made of any electrically conductive material. Examples include gold, silver, carbon, platinum, platinum-iridium, nickel titanium, and stainless steel.

Although RF heads and RF generators are provided in examplary systems, the invention also contemplates therapeutic systems having any energy delivery head and any energy generator. Accordingly, any of the RF heads taught herein can alternatively be configured as any other electromagnetic energy (e.g. microwave) delivery head and provided in a system with a console having the appropriate energy generator.

Memory Device

According to the present invention, a therapeutic device comprises a memory device comprising control instructions as data. The memory device can be configured in any manner that that allows communication between the memory device and a controller when the connector of the therapeutic device is connected to the controller or a console comprising the controller.

Any memory device is useful in the present invention.

The memory device can comprise any memory type. Useful memory types include non-volatile and volatile memory.

Optionally, the memory device comprises non-volatile memory. Optionally, the non-volatile memory is selected from read only memory (ROM), programmable read only memory (PROM), erasable programmable read only memory (EPROM), flash memory, battery-backed-up random access memory (RAM), non-volatile RAM, ferromagnetic RAM, magnetic data storage apparatus, including tape drives and disk drives, optical data storage apparatus, electrically erasable programmable read only memory (EEPROM), an SD card (e.g. SDHC, SDXC, or SDSC), a USB device (e.g. Universal Serial Bus (USB) 1.1, USB 2.0 or USB 3.0), or devices substantially identical to an SD or USB device but contained in a non-industry-standard package.

Optionally, the memory device comprises EEPROM. The EEPROM can be, e.g. any non-volatile, semiconductor memory device comprising memory cells which may be written to and erased on a byte-by-byte basis. Examples of useful EEPROM memory include SPI or I2C EEPROM memory.

Optionally, the memory device comprises flash memory. The flash memory can be,
  e.g. any non-volatile, semiconductor memory device that is erasable only in block. Examples of useful flash memory include SPI, SD, USB or I2C flash memory Optionally, the memory device is configured in any manner that allows the data (e.g. parameters or algorithms) on the memory device to be read by the controller but not modified by the controller. This configuration, e.g., prevents users from purposefully or accidentally modifying, updating, or overwriting the data.

Optionally, the memory device is operably linked to the connector of the therapeutic device. In this embodiment, the memory device is configured in any manner such that, upon connection of the connector to a controller (e.g. plugging the therapeutic device into a console comprising the controller and an RF generator), the controller can access the memory device. Optionally, the connector comprises communication wires for connecting the memory device to the controller. Optionally, the connector comprises powered wires for powering the memory device.

Optionally, the memory device is removable connected to the therapeutic device. Optionally, the memory device comprises a personal computer type connector (e.g. USB, firewire, or serial connection). In this embodiment, the memory is optionally configured to allow transfer of data to a personal computer, e.g. upon disconnecting the memory device from the therapeutic device and connecting to a computer.

Controller

Optionally, the therapeutic device comprises a controller for controlling the memory device or the operating head of the therapeutic device. The controller can be any controller (e.g. microprocessor).

Optionally, the controller of the therapeutic device is configured to control (e.g. read from or read from and write to) the memory device or the operating head of the therapeutic device and communicate with the controller of the energy (e.g. RF) generator when the connector of the therapeutic device is connected to the controller of the RF generator.

Optionally, the controller of the therapeutic device is configured to modify (e.g. write to) the memory device or the operating head of the therapeutic device and communicate with the controller of the energy (e.g. RF) generator when the therapeutic device is connected to the console.

Optionally, the controller of the therapeutic device is configured to control one or more optional secondary devices (e.g. sensor or device with a therapeutic function).

Cable

Optionally, the therapeutic device comprises a cable operably linking the connector to the operating head or memory device.

Optionally, the cable comprises one or more electrical wires operably linked to the connector such that the RF generator can transmit RF energy through said electrical wires.

Optionally, the cable comprises one or more communication wires operably linked to the connector such that the controller of the RF generator can communicate with the memory device or controller thereof.

Optionally, the cable comprises one or more sensing wires operably linked to the connector such that the controller of the energy (e.g. RF) generator can receive information from the operating head (e.g. temperature information from a thermocouple).

Optionally, the cable comprises one or more cannulas or lumens for carrying fluids (e.g. liquids or gases) or other materials to and from the operating head.

Data

According to the present invention, the memory device of a therapeutic device comprises data specific to the therapeutic device, a procedure for which the therapeutic device is configured, or a secondary device comprised by the system. The data includes control instructions, wherein the control instructions comprise instructions for controlling the console. Optionally, the control instructions comprise instructions for controlling one or more of: the energy (e.g. RF) generator, an optional secondary device (e.g. sensor, imaging device, UI, and/or second therapeutic device), or any an optional I/O device such as a peripheral, a personal computer, or a second console.

Optionally, the system comprises a secondary device and the therapeutic device memory further comprises instructions that are specific to the secondary device or a procedure for which the secondary device is configured). Additionally or alternatively, the optional secondary device comprises memory device having control instructions (e.g. control instructions specific to the secondary device or a procedure for which the secondary device is configured).

The instructions for controlling the console can comprise any instructions that cause the console controller to control (e.g. send or receive data or analog signals to or from) a console device (e.g. energy generator) or an I/O device connected to the console or communicate with (e.g. send raw or interpreted instructions to) a second controller such as a controller of a second console.

Optionally, the control instructions comprise one or more parameters, one or more executable instructions, or both.

Optionally, the control instructions comprise executable instructions such as algorithms, control software, or scripts. Additionally or alternatively, the control instructions optionally comprise parameters that are input into executable instructions (e.g. general algorithms that reference the parameters) stored on the therapeutic device memory, an optional console memory device, or an optional secondary device memory.

Optionally, the control instructions comprise one or more parameters. Optionally, the parameters comprise one or more of output parameters (e.g. energy output parameters and/or UI output parameters), input parameters (e.g. monitored parameters), calibration parameters, verification parameters, and capability parameters.

Optionally, the control instructions comprise an operating mode characterized by a plurality of energy (e.g. RF) output parameters.

Optionally, the control instructions comprise instructions for controlling or interacting with one or more secondary devices of the system or therapeutic device.

Optionally, control instructions may be machine readable (i.e. binary executable instructions), scripted (i.e. written in a format interpreted by the controller), select from pre-defined actions or database of actions available to the controller, source code (i.e. compiled and the executed by the controller), or a combination thereof.

Optionally, the data further comprises an ID code. The ID code can be any identifier of the therapeutic device or operational head thereof. For example, the ID code can be a serial number. An ID code can be used, e.g. to identify the type of therapeutic device to the controller or a user thereof, to identify predetermined operating parameters or executable instructions stored locally to the controller (e.g. in a lookup table comprising the ID code stored locally to the controller), to identify the facility in which the therapeutic device was used or is intended for use, to identify the facility in which the therapeutic device was manufactured, to identify a clinician by whom the therapeutic device was used or is intended for use, to identify the region for which the therapeutic device was manufactured or intended for use, to identify a brand, division or company associated with the therapeutic device, to identify a console or console software version for which the therapeutic device or data of its memory is configured.

Optionally, the therapeutic device memory device or data thereof comprises one or more of copy-protection, a console software update, region protection, expiration protection, and reprocessing protection.

Optionally, the therapeutic device memory comprises a console software update. For example, the memory device can comprise, complete software updates of the console, including operating system and applications, partial updates of the console software, include some elements of operating system and applications, graphics or display resources customizable elements per customer, changes in workflow rules (i.e. require operator to confirm parameter before beginning therapy), updates of keys (symmetric or asymmetric) which will be used to authenticate future devices, updates of keys (symmetric or asymmetric) which when authenticated by another operator action (such as entering a code) allow the console to be used for a specific number of treatments, updates of the number of uses which the console may perform before requiring a further authorization, or scripts or instructions to copy diagnostic or historical data from the console to the memory device.

Optionally, the data is stored in an encrypted form, which is readable only by an authorized console or an authorized computer. This configuration can be used, e.g. in preventing theft of algorithms and counterfeiting of therapeutic devices.

Optionally, the data stored is encrypted such that is readable only by a subset of consoles, preventing use by unauthorized consoles.

Optionally the encryption is symmetric or asymmetric encryption.

Optionally the encryption may require a challenge-response sequences between the console and therapeutic device.

Optionally the controller may modify the data stored on a therapeutic device so that it is rendered unauthorized for all or a subset of consoles.

A set of control instructions can be tailored, for example, to a specific therapeutic device, energy delivery head (e.g. RF catheter), a specific region (e.g. geographic region), and/or therapeutic procedure.

A system of the invention can comprise one or more memory devices comprising data, wherein at least one of said memory devices is comprised by a therapeutic device. Collectively, the data is configured to at least cause the system to produce a therapeutic or diagnostic effect. Optionally, the system comprises at least one additional memory device such as a console memory device, a memory device of an optional secondary device, or both. Optionally, the system comprises a single memory device comprising all of the data (e.g. control instructions) required by the system to function. Alternatively, the system optionally comprises a plurality of memory devices that collectively comprise the data. Optionally, the system comprises at least one additional memory device such as a console memory device, a memory device of an optional secondary device, or both. Optionally, the therapeutic device memory or optional secondary device memory comprises control instructions specific to a device or procedure and the console comprises a memory device comprising system software (e.g. operating system and/or general algorithms) configured for obtaining, interpreting, and/or carrying out the control instructions stored on the therapeutic device.

Although the data taught hereinabove are advantageously provided on therapeutic device memory or secondary device memory, the invention also contemplates embodiments in which some data is provided on therapeutic device memory or secondary device memory and some data is provided on console memory.

Examplary data useful in the memory device of a therapeutic device is configured to specify to the controller one or more (e.g. each) of the following:

a) The conditions which must exist as defined by the therapeutic device, monitored parameters, and console hardware (e.g. RF generator) to initiate a therapeutic procedure.
b) How the RF energy delivered to the patient is controlled; the algorithms which adjust the amount, rates, and duration of the energy delivered to the patient.
c) The parameters which are monitored and how they affect the RF energy to be delivered; the feedback inputs and gains into the algorithms.
d) The parameters which are to be displayed to the operator via the user interface.
e) The representation (i.e. textual, graphical, refresh rates) and format of the parameters displayed to the operator via the user interface.
f) The parameters which the operator is allowed to modify the treatment and the ranges within said parameters can be modified.
g) The conditions of RF energy output, or the monitored parameters which cause an algorithm to adjust to a new phase or type of energy delivery with different amounts, rates, or durations.
h) The conditions of RF energy output, or monitored parameters which cause the change in operator of other connected equipment (e.g. changing the flow rate of an infusion pump connected to the generator via the USB or Ethernet interfaces)
i) The changes in the representation of the parameters displayed on the user interface when changes in control algorithm or monitored parameters change.
j) The conditions of RF energy output, or of the monitored parameters, for which the Operator should be alerted via the user interface.
k) The messages/indications which are displayed to the operator when being alerted and the allowed responses.
l) The conditions of RF energy output, or of the monitored parameters, for which the RF output is immediately terminated.
m) The messages/indications which are displayed to the operator when delivery has been terminated.
n) The messages/indications which should be displayed to the operator when the operator manually terminates the delivery of RF output.
o) The audio tones which to be sounded by the generator during the states of operation of RF output, alarms, and user interface events.
p) The information which is to be included in a printed or exported (e.g. as a PDF or text document) report summarizing the treatment.
q) The format of exported or printed reports.
r) The information which is to be transmitted via a network interface summarizing the treatment. For example information transmitted to an Electronic Medical Record (EMR) system.
s) The detailed information of the RF output and monitored parameters (e.g. temperature, power, impedance, heart rate as measured several times per second during a treatment) which should contained in a log file or technical database contained within the RF generator.
t) The detailed information and format in which it is to be transmitted in real time to an external device via a communications or networking interface.
u) The means by which to determine the state (i.e. condition of) the Therapeutic Device and its appropriateness for use.
v) The means by which to determine the authenticity of the therapeutic device.
w) The means by which to limit the usage of the therapeutic device.
x) The detailed or summary information of the RF output, operator-adjustable parameters, monitored parameters, alerts, and end state of treatment which should be stored in an operator-accessible database within the generator.
y) The detailed or summary information of the RF output, operator-adjustable parameters, monitored parameters, alerts, and end state of treatment which should be stored in the therapeutic device memory.
z) Translations to dialects, languages or regionally appropriate output of data sent to the display, peripherals or via the network interface
aa) Configuration information to control data transmission to remote locations
bb) Calibration-related information including expiration and action to take upon expiration
cc) Verification instructions for ensuring the console or device is meeting minimum performance requirements.

Parameters

Optionally, the control instructions of a therapeutic device memory or secondary device memory comprise at least one parameter ('parameter').

Useful parameters include any parameters used by a controller to control a system device (e.g. energy generator, therapeutic device, or secondary device). For example, a parameter can be used by an algorithm stored locally to the console or stored on the memory device of the therapeutic device or secondary device. Optionally, the algorithm can provide a step of controlling the console based on the parameter, e.g. by providing the step of controlling the console (e.g. reducing power of energy output) as a dependent variable of an independent variable defined by the parameter or value thereof (e.g. maximum temperature or impedance change). Additionally or alternatively, the parameter can define a trigger (e.g. a sensed conduction such as parameter value) that initiates a step of control (e.g. discontinuing energy output or outputting an alarm to a user output device).

Optionally, the parameter is any of the following types: a target value (e.g. target power or voltage output, target temperature sensed, or target temperature range of the target site), a value limit (e.g. maximum or minimum temperature), or a value trend or pattern (e.g. trend of impedance values that indicate proper contact of electrodes to a target site).

Additionally, the parameter optionally defines an absolute value, a change in value, or a rate of change in value (e.g. temperature or impedance).

Useful parameters include input (e.g. sensed or monitored) parameters, output parameters (e.g. parameters of energy output), or device parameters (e.g. verification parameters, calibration parameters, capability parameters). Optionally, the parameters comprise one or both of an input parameter (e.g. sensed parameter) and an output parameter. Optionally, the input parameter comprises a trigger and the output parameter comprises an event triggered by the trigger (e.g. trigger is change in temperature or impedance and the output parameter is the power of energy output to provide when the trigger value is sensed). Optionally, a reversibly connected memory device comprises an input parameter (e.g. target value, trigger value, or value limit), and an algorithm is provided (e.g. on console memory or on a reversibly connected memory device) that causes the system to monitor (e.g. continuously or periodically sense) the parameter (e.g. temperature, button status, or heart rate) and compare the value of the monitored parameter to the value of the input parameter stored on the memory device.

Optionally, the memory device of the therapeutic device, a secondary device, or the console comprises a plurality of settings, wherein each setting comprises a set of one or more parameter values (e.g. energy output parameter values). Optionally, the system is configured such that the user can select a setting from the plurality of settings.

Optionally, the control instructions comprise one or more output parameters, e.g. an energy output parameter or a UI output parameter.

Optionally, the control instructions comprise one or more energy output parameters,
 e.g. stored on a therapeutic device memory. Useful energy output parameters include any parameters of energy output by an energy generator. Optionally, the energy generator is a generator of a therapeutic energy selected from wave, mechanical, plasma, cryoablation, and electroporation. Optionally, the therapeutic energy is wave energy selected from electromagnetic (e.g. RF or microwave), sonic (e.g. ultrasound or HIFU), laser, or nerve stimulation.

Optionally, the control instructions comprise one or more energy output parameters of electromagnetic energy, e.g. RF or microwave energy. Optionally, the one or more energy output parameters are selected from voltage, current, temperature, duty-cycle, pulse rate, pulse duration, pulse shape, ramp time, treatment time, joules delivered, frequency, waveshape, power, phase, and channel used.

Optionally, the control instructions comprise one or more energy output parameters of sonic energy, e.g. ultrasound or HIFU. Optionally, the one or more energy output parameters are selected from beam intensity, beam phase, power, frequency, channels used, duty cycle, current, voltage, pulse rate, pulse duration, pulse shape, ramp time, treatment time, waveshape, phase, and joules delivered.

Optionally, the control instructions comprise one or more energy output parameters of laser energy. Optionally, the one or more energy output parameters are selected from average power, peak power, beam intensity, beam size, voltage, current, duty-cycle, pulse rate, pulse duration, pulse shape, ramp time, treatment time, phase, joules delivered, and channels used.

Optionally, the control instructions comprise one or more energy output parameters of nerve stimulation energy. Optionally, the one or more energy output parameters are selected from stimulation rate, waveshape, current, voltage, pulse rate, pulse duration, pulse shape, ramp time, treatment time, frequency, phase, power, channel used.

Optionally, the control instructions comprise one or more energy output parameters of mechanical energy, e.g. irrigation energy. Optionally, the one or more energy output parameters are selected from flow rate, pressure, pump speed, pump torque, flow shape, ramp time, duration, and volume delivered.

Optionally, the control instructions comprise one or more energy output parameters of plasma energy. Optionally, the one or more energy output parameters are selected from gas flow rate, power, voltage, initiation output level, duty cycle, pulse rate, pulse duration, pulse shape, ramp time, treatment time, joules delivered, and channels.

Optionally, the control instructions comprise one or more energy output parameters of cryoablation energy. Optionally, the one or more energy output parameters are selected from coolant flow, thermoelectric power, thermoelectric current, coolant pressure, pulse frequency, pulse duty cycle, ramp rate, and treatment time.

Optionally, the control instructions comprise one or more energy output parameters of electroporation energy. Optionally, the one or more energy output parameters are selected from voltage, charge, pulse rate, pulse width, joules, number of pulses, and treatment duration.

Optionally, the control instructions comprise one or more UI output parameters, e.g. stored on therapeutic device memory or secondary device memory. Optionally, the one or more UI output parameters comprise notification parameters and/or display parameters. Useful notification parameters include data displayed (e.g. screens, triggers, ranges of accepted values, or any parameter or value thereof sensed (e.g. monitored) or stored on a memory device) or alerts (e.g. warnings or alarms). Useful display parameters include text size, graph axes, update rate, filtering, color, units of values, and precision of values.

Optionally, the control instructions comprise one or more capability parameters, e.g. stored on therapeutic device or secondary device memory. The capability parameter can be,
 e.g. any capability parameter of hardware local to the memory device (e.g. therapeutic device memory comprising a capability parameter of the therapeutic device). Useful capability parameters include compatible or incompatible modes of operation, compatible or incompatible devices (e.g. compatible or incompatible secondary devices, therapeutic devices, or consoles or energy generators).

Optionally, the control instructions comprise one or more verification parameters,
 e.g. stored on a therapeutic device memory or secondary device (e.g. intermediate device or d/t device) memory. The verification parameters can be, e.g. parameters used by the controller to verify that the system, or connected device (e.g. therapeutic device or secondary device) thereof is properly configured or verified for use. Useful verification parameters include use data, recommend number of uses, model number, company/brand, Produced for, Production Plant, time or date of production, maximum number of uses allowed, authentication (e.g. key) of a local device (e.g. authentication of a therapeutic device provided on therapeutic device memory), authentication of a remote device (e.g. authentication of an intermediate device provided on therapeutic device memory), re-use prevention rules, sterilization validity information, sterilization expiration date, device serial number, device authorized for use for this system, device authorized for use in the country or geography in which this system was sold, device authorized for use with this system based on systems owner, device authorized for use with this system based on system's brand name, device authorized for use with this system based on feature set, device authorized for use with this system based on the total number of treatments authorized for this system, device authorized for use with this system based on the re-use history of this device, as well as authentication key(s) of data stored on the memory device, such as a) software updates encrypted with symmetric (single key) or asymmetric (public/private) methods, the validity of which must be confirmed before the system will provide therapy, b) authorization keys encrypted with symmetric (single key) or asymmetric (public/private) methods, the validity of which must be confirmed before the system will provide therapy, or c) memory device data such as parameters encrypted with symmetric (single key) or asymmetric (public/private key) methods, the validity of which must be confirmed before the system will provide therapy.

Optionally, the control instructions comprise one or more calibration parameters,
 e.g. stored on a therapeutic device memory or secondary device. The calibration parameters can be, e.g. any calibration parameters corresponding to hardware that is local to the memory device on which the calibration parameters are stored (e.g. calibration parameters of a therapeutic device energy delivery head stored on the therapeutic device memory). Optionally, the calibration parameters comprise structural calibration parameters and/or functional calibration parameters. Optionally, the hardware is selected from an energy delivery head, a secondary device (e.g. an intermediate device or d/t device), and a sensor (e.g. pressure sensor, contract for censor, or temperature sensor).

Optionally, the control instructions comprise one or more calibration parameters of an energy delivery head. Optionally, the energy delivery head is selected from a wave energy delivery head, a mechanical energy delivery head, a plasma energy delivery head, a cryoablation energy delivery head, and an electroporation energy delivery head, a pneumatic pressure head, a vaporizer head, or an irrigation head (e.g. irrigation catheter). Optionally, the calibration parameters are stored on a memory device local (e.g. not reversibly connected) to the hardware described by the calibration parameters.

Optionally, the control instructions comprise one or more calibration parameters of a wave energy delivery head (e.g. electrode), e.g. one or more calibration parameters for energy delivery and/or one or more calibration parameters for imaging or other detection. Useful calibration parameters for energy delivery include loss factors, impedances, including for example R-L-C values, Z and Phase, complex Z and S parameters, surface area, maximum energy allowed, diameter, energy coupling factors, physical lengths (needles, tips, probes, cables), electrode exposure lengths, distance between electrodes, impedances between electrodes, impedance between channels or wiring leads, resonant frequencies, thermal impedance, thermal time constant, temperature feedback gains, offsets, and characteristic equations, and cooling flow rate. Useful calibration parameters for imaging or detection include length, area, mass, orientation, volume, opacity, and antenna coupling coefficient (e.g. of a first energy delivery head).

Optionally, the control instructions comprise one or more calibration parameters of a pneumatic pressure head or vaporizer head (e.g. head ventilator or vaporizer head such as patient tube). Useful calibration parameters include tube resistance, tube diameter, tube volume, tube length, pressure vs. flow characteristic equation parameters, vaporizer output characteristic equations, leak rate, O2 Perfusion sensor characterization curves, and O2 sensor gains, offsets, and characteristic equation parameters.

Optionally, the control instructions comprise one or more calibration parameters of an irrigation head (e.g. irrigation catheter). Useful calibration parameters include tube diameter, tube volume, tube length, maximum pressure allowed, maximum flow rate allowed, pressure vs. flow characteristic equation parameters, recommended flow rate, balloon volume, flow vs. cooling characteristic equation parameters, electrode size, and pressure measurement characteristic equation parameters.

Optionally, the control instructions comprise one or more calibration parameters of an intermediate device. Useful calibration parameters include impedance, loss factors, frequency characterization, length, contact impedance, temperature measurement characteristic equation parameters, pressure measurement characteristic equation parameters, and inter-signal impedances.

Optionally, control instructions comprise an input parameter. Optionally, the input parameter can be parameter that is used by the controller to control (e.g. modulate, initiate, terminate, or prevent) an output such as an energy (e.g. RF) output or user output device (e.g. display such as to indicate alarms or states of a workflow). Optionally, the input parameter is a parameter of sensory input (i.e. a parameter that can be detected using a sensor), e.g. an environmental condition or a therapeutic device condition, an image parameter, a user input parameter (e.g. toggle status), or any energy output parameter that can be sensed. Optionally, the input parameter provides a target value, value limit, or value trend, e.g. that can be sensed by a sensor or monitored.

Optionally, the control instructions comprise an input parameter that is an effect of treatment, for example, therapeutic effect or side effect of energy delivery. Examples of input parameters include environmental conditions such as air pressure, temperature, or chemical composition, or biological conditions such as ECG, EEG, EMG, or EOG, heart rate, respiration, oxygen saturation level, carbon dioxide saturation level, de-oxygenated hemoglobin level, blood pressure, breath rate, blood flow, and muscle contraction. Optionally, the input parameter is stored on the therapeutic device memory.

Optionally, the control instructions comprise a therapeutic device condition or a secondary device condition. Examples include contact force or pressure, temperature, acceleration, impedance, phase, volume, position, disconnection, flow rate, chemical composition, rate of change of impedance, rate of change of temperature, rate of change in pressures, change in power required to maintain temperature, change in power required to maintain impedance, change in power required to maintain pressure, and change in power required to maintain flow. Optionally, the parameter is stored on the therapeutic device memory.

Optionally, the control instructions comprise an image parameter, e.g. image contrast (e.g. monitored image contrast to trigger delivery of additional contrast agent), radiological marker movement, and radiological marker position. Optionally, the image parameter is stored on the therapeutic device memory.

Optionally, the parameter comprises state transition criteria and standards for controlling a change in user output device (e.g. display), energy output, or secondary device state.

Optionally, the parameter comprises an RF output parameter. Optionally, the RF output parameter comprises one or more of voltage, current, time, temperature, stimulation rate, pulse rate, pulse duration, ramp time, frequency, amplitude, power, waveshape, power and channel used (for multi-channel configurations).

Optionally, the parameter comprises an environmental condition parameter as an input parameter (e.g. trigger value, target value, or value limit). For example, the environmental condition can be a condition of a biological tissue (e.g. target tissue) or a condition of an organism comprising target tissue. Optionally, the environmental condition is a condition affected by energy output (e.g. temperature or impedance changes due to boiling or popping of fluid at a target site). Optionally, the parameter is a diagnostic parameter. Optionally, the parameter is any parameter that can be monitored by an optional sensor. Optionally, the parameter defines one or more of temperature, impedance, voltage, force, pressure, fluid flow, light/optics, sound, chemical composition, thermal time constant, cross-conduction between multiple channels, image or appearance (e.g. fibre-optic imaging within balloon catheter), respiration rate, electrical activity (e.g. ECG, EEG, EMG, or EOG such as morphological feature or rate) in a tissue such as the heart, retina, cerebral cortex, or any muscle tissue, or a biological (e.g. therapeutic- or non-therapeutic-) effect of a therapeutic head of the therapeutic device.

Optionally, the input parameter comprises a therapeutic device condition parameter. Optionally, the parameter defines one or more of: damage (e.g. damage of an operational head), configuration, use (e.g. duration of use, time and/or date of first or previous use, or expiration), impedance, voltage, fluid flow, thermal time constant, pressure or contract force (e.g. of RF electrode on target site), and user input status (e.g. status of a user input device of the therapeutic device such as a toggle button).

Optionally, the input parameter comprises a therapeutic device condition parameter that indicates whether the therapeutic device is functioning as intended ('verification parameter'). The verification parameter is optionally any parameter that changes as a result of damage to the therapeutic device. For example, the verification parameter can indicate damage to the operational head, the connector, or operable linkages in the therapeutic device. Optionally, the verification parameter defines one or more of minimum thermistor impedance maximum thermistor impedance, minimum thermocouple impedance, maximum thermocouple impedance, minimum RF impedance, maximum RF impedance, minimum change in temperature due to RF pulse, maximum change in temperature due to RF pulse, pressure change due to fluid injection, minimum pressure sensor impedance, and maximum pressure sensor impedance. Optionally, the memory device of the therapeutic device comprises data indicating the expected value of the verification parameter for an undamaged therapeutic device and the controller compares the actual value of the parameter (e.g. by sensor) to the expected value to determine if the therapeutic device is damaged.

According to the present invention, a parameter can optionally be stored on the memory device and used by the controller to perform a therapeutic procedure (e.g. configured or modulate the energy generator and/or secondary devices such as a user interface or secondary therapeutic devices such as a fluid pump). The values of parameters stored on the memory device can be used, e.g. as triggers or dependent variables in algorithms of the controller or can be used for comparison with sensed or monitored parameter values of a sensor as well as outputted parameters of energy out.

Optionally, the system comprises one or more settings (e.g. stored on a therapeutic device memory, secondary device memory, or console memory), wherein each setting comprises one or more parameters, wherein the at least one of the values of said one or more parameters are stored on a reversibly connected memory device (e.g. a therapeutic device memory or a secondary device memory). The parameters can optionally be any parameters taught herein that are stored on a memory device.

Optionally, the system comprises one or more settings of energy delivery that are selectable by the controller or system user.

Examples of settings for an energy delivery head include, e.g. wave energy delivery head (e.g. RF electrode), treatment temperature, treatment time, power, voltage, stim amplitude, stim rates, stim pulse width, electrodes to energize, fluid flow rate, duration of treatment, joules to deliver, size of lesion, shape of lesion, joules to absorb (cooling), maximum voltage, maximum flow rate, minimum flow rate, channels to use, type of procedure, anatomy targeted, data output formats, audible volumes.

Examples of useful of settings for a pneumatic pressure head or vaporizer head include fluid flow rate, fluid volume to deliver, humidification level, pneumatic flow rate, pneumatic pressure, patient type (adult/pediatric, weight, age, gender), breath modes allowed, breath rates allowed, tidal volumes allowed, spontaneous breath intervals allowed, breath rate alarms, breath tidal volume alarms, forced-breath timeout, breath mode parameters, intra-cycle pressures (i.e. pip), inter-cycle pressures (i.e. PEEP), target oxygen perfusion, vascular support pressures, vascular support pressure gradients, and vascular compression rates.

Examples of useful of settings for an irrigation head include tube diameter, volume to inject, contrast agent flow rate, pressure to maintain, maximum pressure to allow, allowable leakage rate, bubble detection sensitivity, and fluid pre-heat/cool temperature.

Although the parameters taught herein are advantageously provided on therapeutic device memory or secondary device memory, the invention also contemplates embodiments in which some parameters are provided on therapeutic device memory or secondary device memory and some parameters are provided on console memory.

Executable Instructions and Algorithms

Optionally, the control instructions comprise executable instructions or algorithms ('algorithms'). Useful algorithms include any algorithms that instruct the controller to control the console, a connected therapeutic device, an optional secondary device, or any I/O device (e.g. a peripheral device).

Optionally, one or more algorithms are stored on the memory device of the therapeutic device or a secondary device. Alternatively, one or more algorithms are optionally stored on a console memory device, wherein the algorithms reference once or more parameters stored on the therapeutic device memory.

Optionally, the control instructions comprise one or more treatment algorithms, predictive algorithms, or control algorithms.

Optionally, the control instructions comprise a treatment algorithm. Useful treatment algorithms include any sequence of energy delivery events controlled by the occurrence of or change in sensed or stored parameters. The sequence can be, e.g. any sequence which has been shown to be effective at causing a therapeutic effect.

Optionally, the control instructions comprise a predictive algorithm. Useful predictive algorithms include any a sequence of energy delivery events which are driven by the controller to produce a certain outcome (i.e. lesion size), based on an equation, computerized model, simulation which is calculated by the console and informed by the occurrence of or change in sensed or stored parameters.

Optionally, the control instructions comprise a control algorithm. Useful control algorithms include any sequence of adjustments in the energy delivered by the console made by the controller which are calculated to maintain a sensed parameter, or multiple sensed parameters, at a predefined level or vector, based on sensory inputs. Examples useful control algorithm structures include a control law or a feedback control system, as is known in the art.

Optionally, the control instructions comprise an algorithm comprising one or more of the following steps, perform a step of therapy (e.g. energy output), perform a step of sensing or monitoring (e.g. temperature or connection status), perform a step of controlling a user interface, perform a step of controlling a memory device, perform a step of controlling an imaging device, or make a calculation. Examples of useful calculations include, e.g. functions or equations referring to a parameter (e.g. as a dependent variable), e.g. as a trigger value, limit, or target value. Other useful calculations include calculation of a sensed condition based on sensor feedback (e.g. calculation of temperature based on thermocouple feedback), calculations based on a control law, for example a PID control loop, such that target values are maintained, calculations advancing the state of a computerized model of the system to predict a parameter not directly measured, calculations comparing the state of a computerized model of the system, measuring the discrepancies between the modeled and measured system, adjusting the model more accurately represent the system, and predict parameters not directly measured, and calculations which filter, integrate, or otherwise condition sensor feedback to provide a derived sensor input suitable for triggering, limit, or a target value.

Optionally, a useful algorithm comprises a combination of steps selected from a) a sensing step and a therapy step (e.g. a step of therapy dependent on sensed condition); b) a sensing step and a UI output step (e.g. sensing and displaying value or result of sensed condition), a sensing step and a step of controlling another device (e.g. a fluid flow increase triggering an ablation energy change).

Optionally, a useful algorithm comprises one or more steps of controlling energy output. Optionally, the one or more steps of controlling energy output comprise one or more of enabling energy output (e.g. upon connection and verification of a therapeutic device), initiating energy output (e.g. upon sensing or detecting that parameters in an allowable region or target range, operator has selected valid settings, and operator has activated the initiation mechanism), terminating energy output (e.g. based on user input such as activating a termination mechanism, upon conclusion of an algorithm, upon a termination condition based on sensed condition, upon termination condition based on predicted outcome reached, or upon termination based on an detected fault or failure of the console, therapeutic device or other device such as a secondary device), and modulating energy output (e.g. a change in energy output based on sensed condition to maintain target value).

Optionally, a useful algorithm comprises one or more steps of controlling a UI. Examples of useful steps of controlling a UI include displaying screens, fields, alerts, or workflows, displaying feedback from sensors or imaging device, displaying feedback from predictive models (is this already included in calculations), displaying calculations, displaying settings from which the operator must select to inform the control of the device(s), displaying device and secondary device verification information, and displaying previous data stored on a therapeutic device or secondary device.

Optionally, a useful algorithm comprises one or more steps of controlling a memory device. Optionally, the steps of controlling a memory device comprise reading from (e.g. obtaining parameters or other stored data) or writing to the memory device (e.g. storing data of energy delivery record to the memory device such as storage of the sequence of some or all of sensed values, storage of initiation events, storage of termination events, or storage of energy modulation sequence).

Optionally, a useful algorithm comprises one or more steps of controlling an imaging device. Examples of useful steps of controlling an imaging device include, obtaining an image, obtaining spatial and tissue characterization, performing image analysis to determine the relative position of energy delivery electrodes or head to that of anatomical structures, informing the user of adjustments to the make to the device position to achieve intended orientation of energy delivery electrodes or head and anatomical structures, controlling the injection of contrast agent to improve information of electrode and anatomical feature orientation, adjusting the orientation or position of the imaging head to improve the information of electrode and anatomical feature orientation, and adjusting the orientation or position of the patient to improve the information of electrode and anatomical feature orientation.

Optionally, a useful algorithm comprises one or more steps of controlling an input device (e.g. sensor), e.g. a step of obtaining or monitoring feedback from the input device. Such steps of controlling an input device can be used, e.g. to trigger an event (e.g. any described herein), as target value, as a limit, to applying calibration parameters to obtain more accurate readings, obtaining parameters settings to achieve correct sensitivity and frequency response, or trigger the sampling of an input measurement.

Optionally, a useful algorithm comprises one or more steps of making calculations. Optionally, the one or more calculations are selected from lesion calculations (e.g. lesion size, lesion shape, lesion position, amount of energy absorption by a tissue, and effect of a combination of energy from optional multiple electrodes), lung calculations (e.g. lung volume, lung compliance, lung resistance, or work of breathing), sequential compression device calculations (e.g. rate of venous bed engorgement, rate of compression sequences), optical diagnostic device calculations (e.g. oxygen saturation, CO partial pressure, or $CO_2$ partial pressure) and surgical navigation device calculations (e.g. orientation to target, orientation to critical anatomical structures, distance to target, or distance to critical anatomical structures).

Any type algorithm is useful in the present invention. For example, the algorithm can be machine code (i.e. executed directly by the controller) or can be written in any programming language (e.g. BASIC, Lua, Java, or FORTH) for which an interpreter is provided local to the controller. Optionally, the algorithm is provided as any of: a binary image directly by the console controller; dynamically linked libraries, e.g. binary images executable by the console controller, but do so by being 'called' by the software of a pre-existing higher-level application or framework; a textual representation (e.g. XML or plain-text script file), which specifies the operations to be performed to a pre-existing higher-level application or framework; a programming language; and an intermediate language which is compiled into an efficient machine-readable format which is not the native instructions of the console controller, such as p-code or Java bytecode, and is interpreted by a virtual machine pre-existing on the console.

Optionally, the algorithm instructs the controller to control an energy generator, a therapeutic head of the therapeutic device, an optional sensory head of the therapeutic device, or a secondary device.

Optionally, the algorithm comprises one or more parameter values. The one or more parameters are optionally any parameters taught herein. In this embodiment, the algorithm can be provided on the memory device of the therapeutic device. Alternatively, the algorithm references one or more parameters, the values of which are not provided by the algorithm. In this alternative embodiment, optionally a) the algorithm and the parameter values can both be stored on the memory device of the therapeutic device; or b) the algorithm can be stored locally to the controller and the parameter values can be stored on the memory device of the therapeutic device.

Optionally, the algorithm is configured for controlling one or more output devices based on the input from one or more input devices. For example, the algorithm can comprise a step of controlling an output device (e.g. energy generator such as RF generator or fluid pump or a user output device such as a UI) that is dependent or triggered by the input from a sensor (e.g. temperature sensor, ECG, or impedance sensor).

Optionally, the algorithm comprises one or more steps of initiation, termination, prevention (e.g. prevention of output), or modulation (e.g. modulation of output). Optionally, the steps are triggered steps, e.g. the algorithm comprises (or references) parameter values that must be present prior to the controller carrying out a step (e.g. a trigger that automatically results in carrying out of the step or a trigger that allows the carrying out of a step).

Optionally, the algorithm comprises instructions for conducting an RF procedure ('RF algorithm').

Optionally, the algorithm is an RF algorithm comprising or referencing one or more parameters taught herein. Optionally, the algorithm provides one or more of: channel(s) to control; average power to deliver; peak power to deliver; duration of delivery; temperature to maintain; voltage to maintain; current to maintain; maximum power to be used to maintain voltage; maximum power to be used to maintain current; maximum power to be used to maintain temperature; minimum power to be used to maintain temperature; maximum number of joules to deliver; maximum voltage allowed; maximum current allowed; time to ramp to temperature; time to ramp to power; profile, or intermediate points on power vs. time curve, to be followed while changing power; profile, or intermediate points on temperature vs. time curve, to be followed while changing temperature; modulation period of RF energy; modulation duty cycle of RF energy; frequency of RF energy; control systems gains (e.g. proportional, integral, and/or derivative gains in temperature and power PID control loops); estimates of parameters used to predict the response of the patient/device system such as thermal mass, thermal time constant, or energy lost to blood flow, etc. Optionally, the algorithm provides one or more triggers.

Optionally, the algorithm (e.g. RF algorithm) comprises one or more triggers. The triggers can be any parameters or parameter values that that cause the controller to perform a step or a series of steps ('segment' or 'states') in a workflow such as a sensory step, an output step (e.g. RF output), or a step of setting one or more other triggers. Optionally, the one or more triggers are selected from: absolute maximum temperature limit, absolute minimum temperature limit; absolute maximum power limit; absolute minimum power limit; absolute maximum impedance limit; absolute minimum impedance limit; relative temperature change; relative power change; relative impedance change; expiration of time; rate of change of temperature; rate of change of impedance; rate of change of power; activation of an RF power activation switch; activation of an RF power activation footswitch; activation of an RF power activation hand switch; ECG feature; ECG rhythm; ECG rate; respiration rate; change in thermal time constant; and change in losses due to blood flow.

Optionally, the algorithm (e.g. RF algorithm) comprises one or more parameters or parameter values that allow or prevent initiation of a therapeutic procedure. Optionally, the parameters include one or more of: target RF impedance (e.g. max or min); target therapeutic device temperature (e.g. max or min); use status of the therapeutic device (e.g. used or unused status); duration of the previous use of the therapeutic device; authentication of therapeutic device; damage status of the therapeutic device; expiration status; detection or non-detection of pulsatile flow; contact force (e.g. max or min); ECG rhythm; ECG feature detection operating; irrigation flow e.g. of an aspiration or infusion device (e.g. max or min); irrigation pressure, e.g. of an aspiration or infusion device (e.g. max or min); and inflation pressure e.g. of an expandable device (e.g. max or min).

Software

A console useful in the invention optionally comprises a memory device ('console memory') comprising system software configured to control the console.

The system software can, for example, provide a framework for controlling devices, running algorithms, and parsing parameters from reversibly connected memory devices (e.g. therapeutic device memory or secondary device memory). Optionally, the framework comprises a programming language. Optionally, the programming language comprises any of the following: scripted language (i.e. Lua, Forth) sequences languages for defining treatment algorithms, control algorithms, or predictive algorithms; compiled objects or dynamic-link-libraries containing embedded implementations of Treatment, Control, or Predictive algorithms; scripted language (i.e. Lua, Forth) sequences for customized reports; scripted language sequences for customized user interfaces; or scripted language sequences for customized electronic communications such as custom databases, email, hospital information systems (HIS), laboratory information systems (LIS), or standardized health information reporting i.e. health Level Seven International (HL7).

Optionally, the system software comprises a configuration management function. Optionally, the configuration management function is configured for conflict resolution and/or to obtain rules from a memory device (e.g. a reversibly connected memory device such as therapeutic device memory or secondary device memory).

Optionally, system software obtains clinical rules or business rules from a memory device. Optionally, the business rules are any rules which prescribe how conflicts of device and software appropriateness should be resolved (e.g. If a memory device has software older than what is already installed, should the software be 'downgraded' before use; or when at least one of the devices in the system has passed its expiration date, should the user be able to override). Optionally, the clinical rules are any rules that prescribe how conflicts of treatment algorithms should be resolved (e.g. one device in the system contains information that a flow rate of 20 ml/min should be used, but another contains information that 25 ml/min should be used. Should one device overrule the other based on type or age? Should the operator be queried to resolve?). Examples of useful rules include identification of compatible device combinations, identification of compatible software, instructions for selecting a software version, instructions to downgrade or upgrade software, an override rule, an error-possessing rule, a data-write rule, or a display rule.

Optionally, the system software is configured to obtain a software update from a reversibly connected memory device (e.g. therapeutic device memory or secondary device memory).

Optionally, the system software comprises executable Instructions and algorithms,
  e.g. any described in the Executable Instructions and Algorithms section above. For example, the system software can comprise treatment algorithms, control algorithms, predictive algorithms, and/or any algorithm, e.g. that references one or more parameters or algorithms stored on a reversibly connected memory device (e.g. therapeutic device memory or secondary device memory).

Optionally, the system software comprises one or more specifications. Device specifications can be any target or acceptable values of parameters (e.g. verification parameters, capabilities, or calibration parameters), e.g. stored as data on a console, that are used for comparison with the actual parameter values stored on a reversibly attached device. Optionally, the system is configured to prevent treatment if the device specifications listed on the console memory do not match the respective parameter values listed on the therapeutic device memory or an optional secondary device memory.

Optionally, the console comprises a console memory device comprising one or more calibration parameters or capabilities parameters of an internal or local device ('internal parameters') such as an energy generator. Such internal parameters such as internal calibration parameters can be used by the controller, e.g. to determine how to achieve a given output using the internal device (e.g. energy generator) or how to interpret a given input from a sensor.

Secondary Device

In one embodiment, a system of the invention comprises a first console comprising a first energy generator and a reversibly connected first therapeutic device comprising a first memory device and a first operational head having a first energy delivery head configured for transmitting the energy output of the first energy generator ('first energy output') and the system further comprises at least one additional electronic device comprising an I/O device that provides a second function other than transmitting the first energy output to the first energy delivery head ('secondary device'). Optionally, the instructions for controlling the secondary device are provided on a reversibly linked memory device (e.g. the first memory device or an optional memory device of the secondary device). Examples of useful systems comprising a secondary device are detailed in Example 13 through Example 19.

Figure 7:
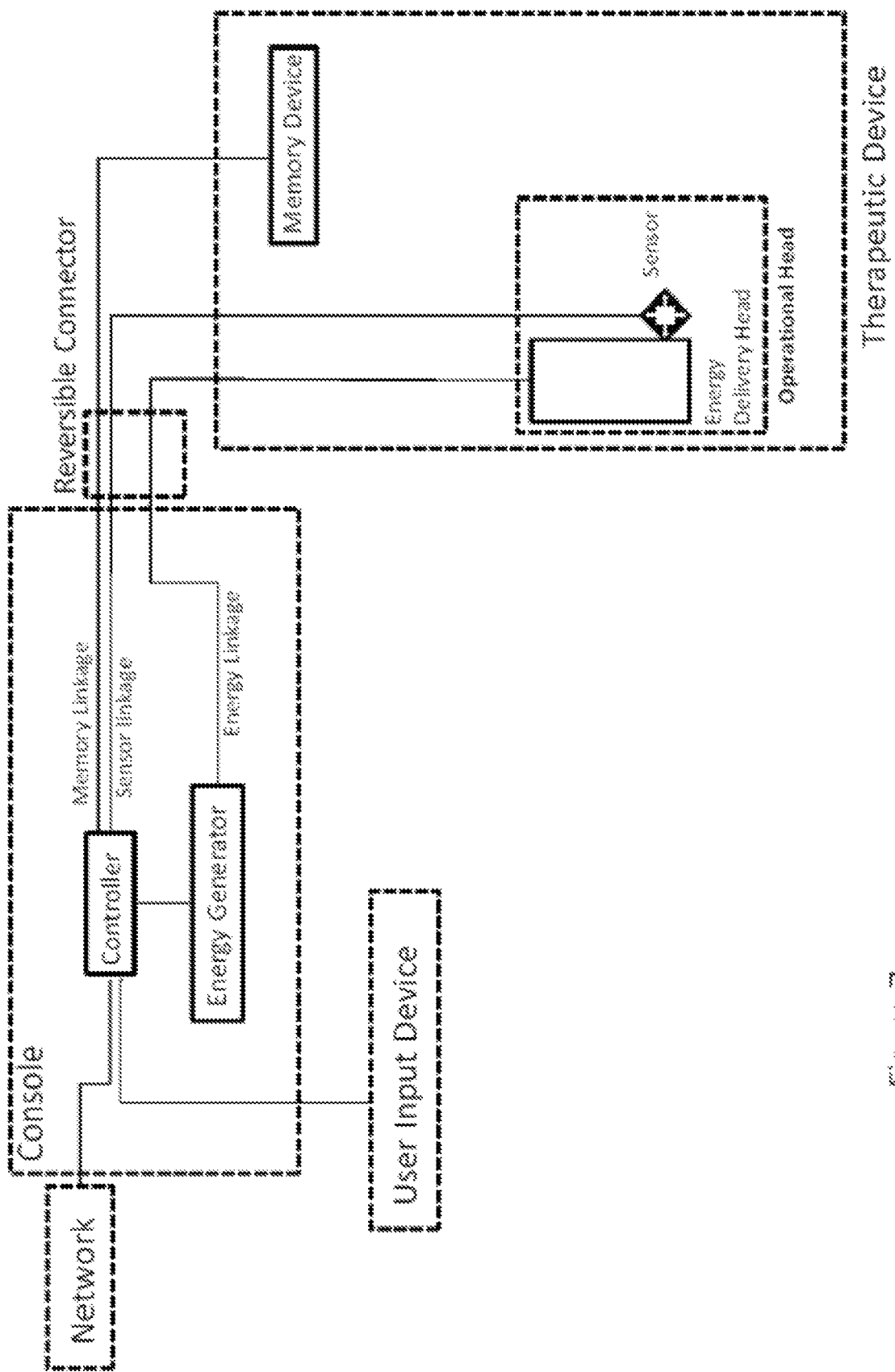
FIG. 7 depicts an examplary system of the present invention.

The secondary device can be operably linked to a system controller in any manner. The secondary device can be, e.g. provided by the therapeutic device, the operational head thereof (e.g. a sensor in a catheter tip or a sensor of a therapeutic device as depicted in FIG. 7), or operably linked to the console controller separately (e.g. a fluid pump connected to the console through a different connector than the therapeutic device, e.g. as depicted in FIG. 8).

Optionally, the secondary device comprises any d/t device or other I/O device configured to operate in cooperation with the energy delivery head, for example, to conduct a therapeutic procedure such as ablation. Examples of such systems are detailed in Example 13 through Example 19.

Useful secondary devices include any d/t device. Optionally the d/t device is a sensor or a device providing a therapeutic function.

Figure 8:
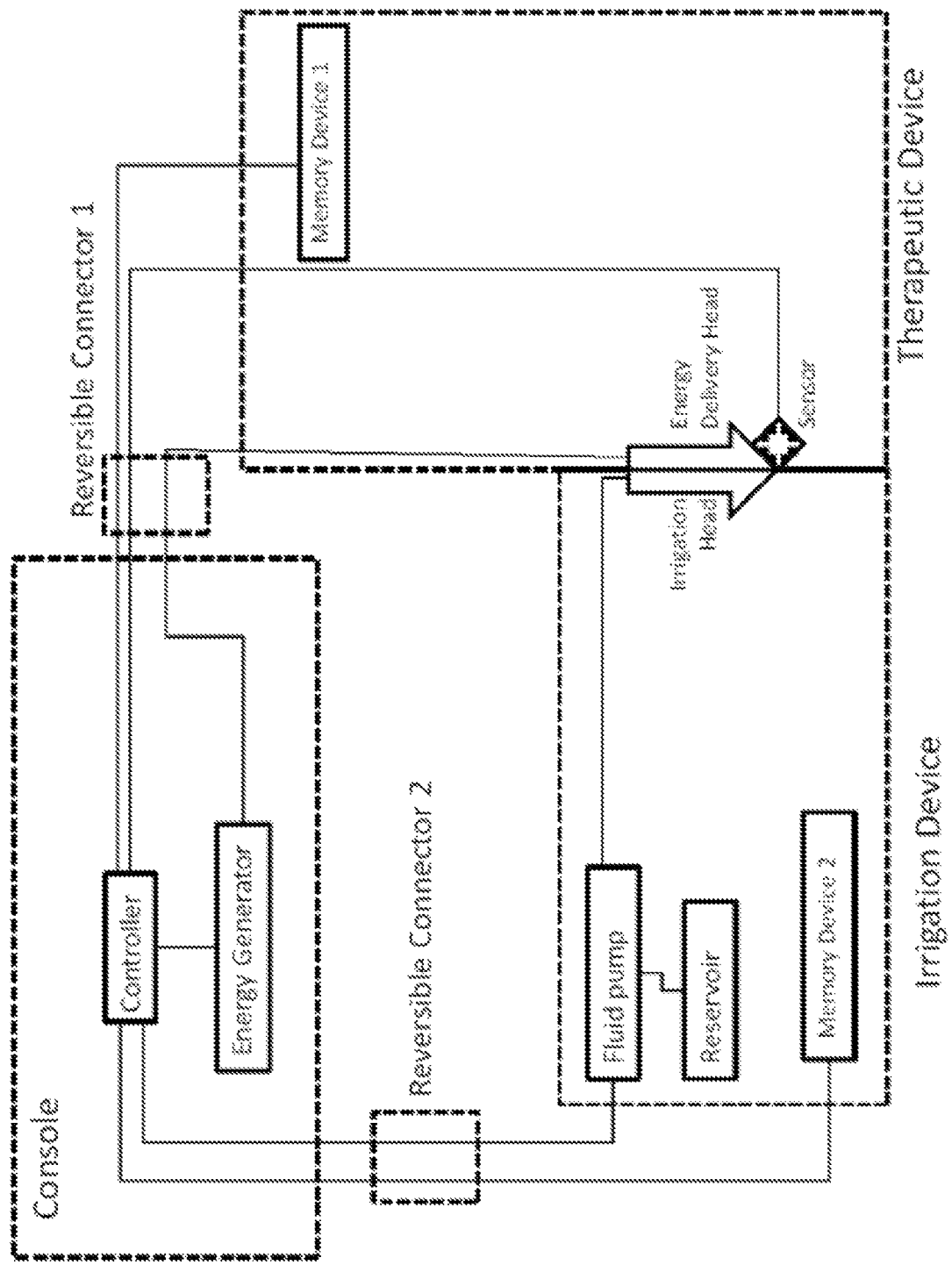
FIG. 8 depicts an examplary system of the present invention.
Figure 9:
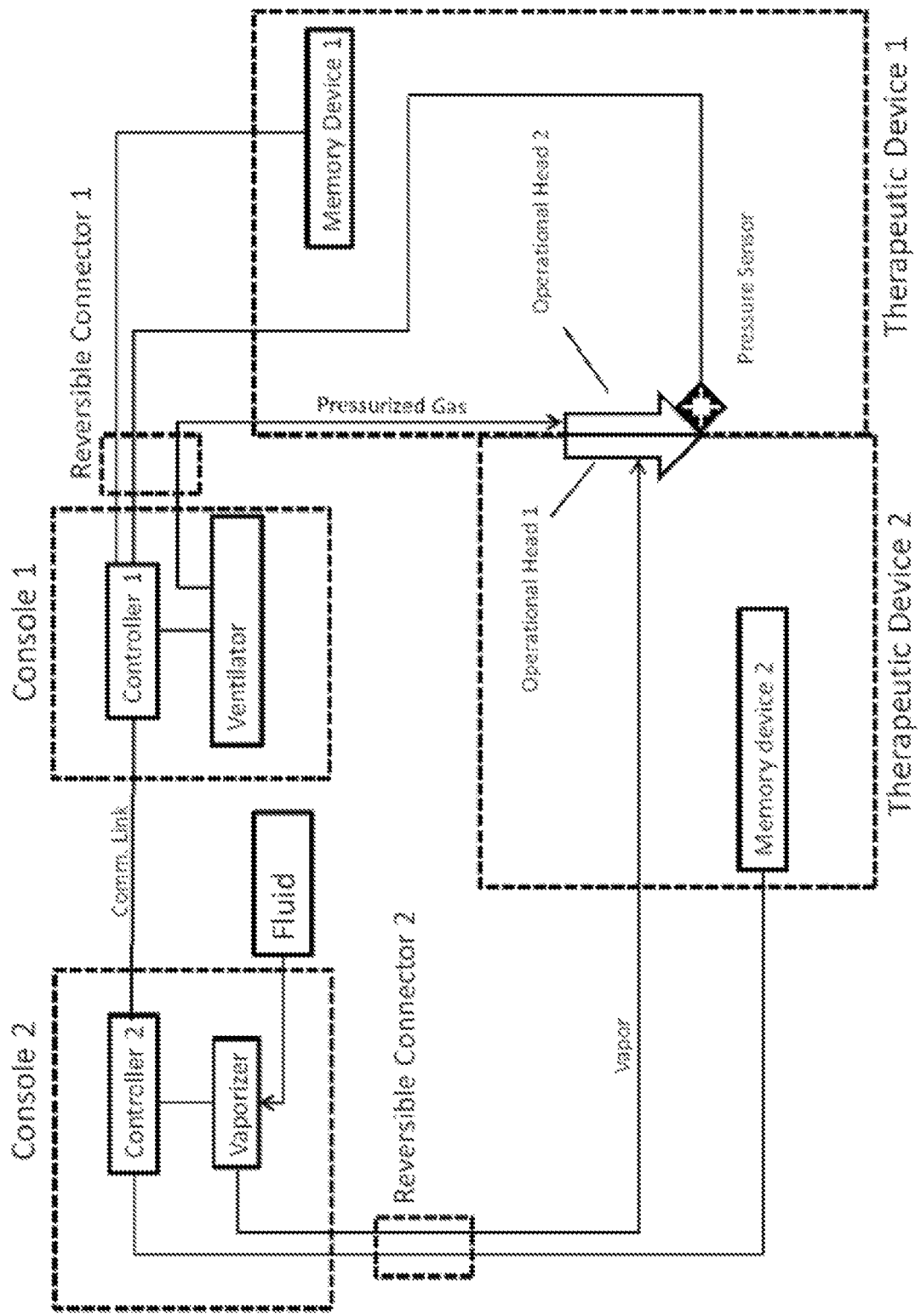
FIG. 9 depicts an examplary system of the present invention.
Figure 11:
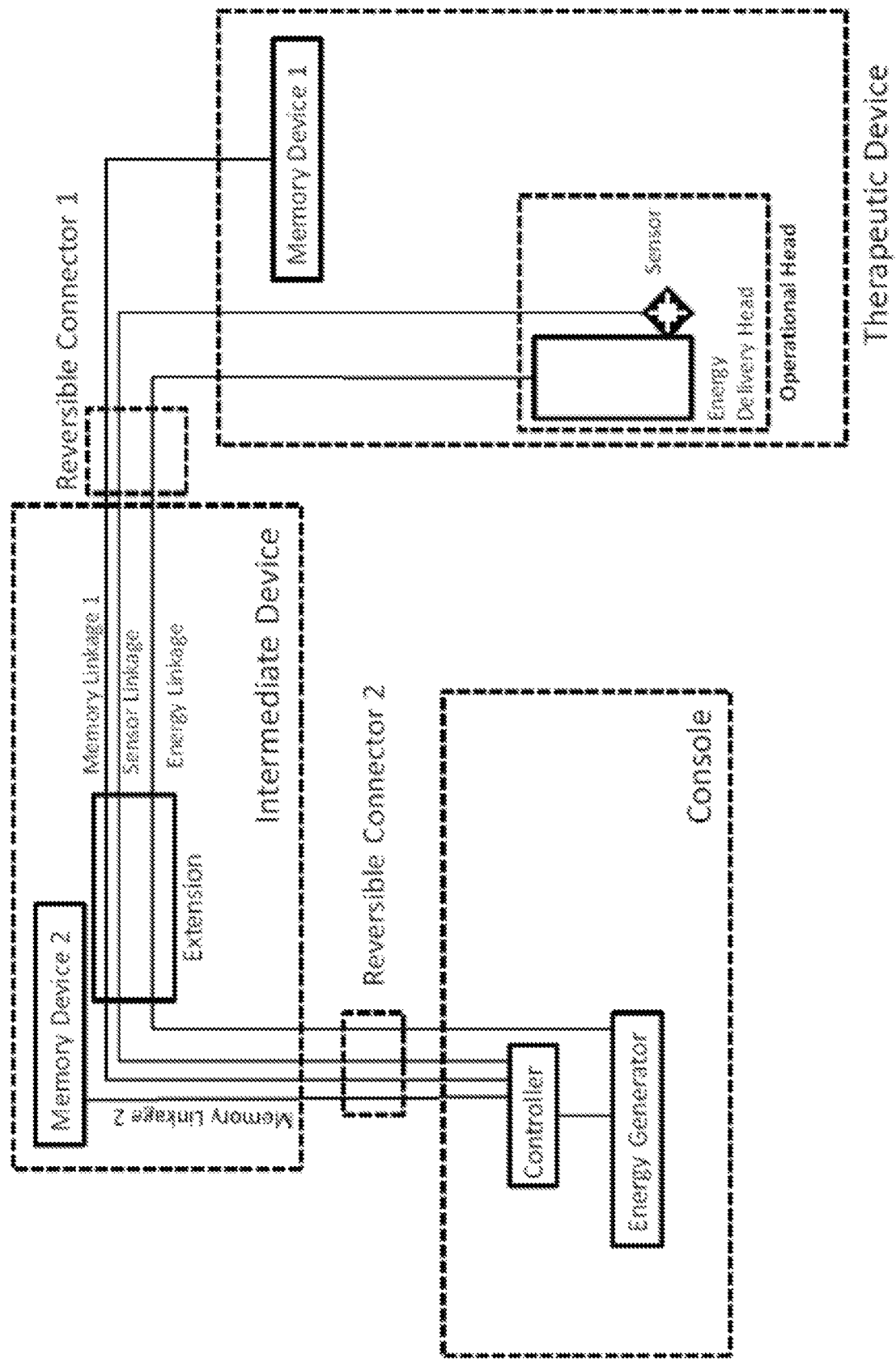
FIG. 11 depicts an examplary system of the present invention.

Optionally, the secondary device is any of:
  a. a sensor or other d/t device provided by the therapeutic device, or operational head thereof (e.g. the sensor depicted in FIG. 7 or FIG. 9);
  b. a second therapeutic device is reversibly connected to the console (e.g. by an independent reversible connector, e.g. as depicted in FIG. 8), optionally comprising reversibly linked memory (e.g. as depicted in FIG. 8);
  c. a secondary device comprising a console (i.e. a second console) with a communications link to the first console (e.g. as depicted in FIG. 9);
  d. a d/t device reversibly connected to the console (e.g. the sensor depicted in FIG. 7 or FIG. 8, the sensor or second therapeutic device depicted in FIG. 9,) or non-reversibly connected to the console (e.g. embedded in) the console; or
  e. an intermediate device positioned between reversibly connected to both the console and the therapeutic device (e.g. to provide a serially connected chain of devices), e.g. as depicted in FIG. 11.

Exemplary Systems with a Secondary Device

In one embodiment, the invention provides a system comprising:
  a. a first console comprising a first energy generator and a first controller configured for controlling the energy output of the first energy generator ('first energy output'), optionally wherein the first energy output comprises therapeutic energy;
  b. a first therapeutic device comprising:
    I. an operational head comprising a first energy delivery head configured for transmitting the first energy output to a target site; and
    II. a first memory device comprising control instructions for said controlling the first energy output;
  c. a first reversible connector configured for operably linking the first energy generator to the first energy delivery head;
  d. a first reversible memory operable linkage configured for operably linking the first memory device to the first controller; and
  e. an electronic device comprising an input or output device ('I/O device') configured for providing a function other than said transmitting the first energy output to the target site ('secondary device'), wherein:
    i. the secondary device is operably linked to the first controller; and
    ii. optionally, the system comprises control instructions for controlling the secondary device on a memory device that is reversibly linked to the first controller.

Examples of such an embodiment are provided by Example 13 through Example 19.

Optionally, the first energy generator is a first therapeutic energy generator. Optionally, the first therapeutic energy generator is a generator of energy selected from electromagnetic energy (e.g. RF energy, microwave energy, and laser energy), mechanical energy (e.g. sonic energy, irrigation or fluid pump, or pneumatic pressure), thermal energy (e.g. heat ablation), freezing energy (e.g. cryosurgery energy) and electrical energy (e.g. electrocautery energy, electrosurgery energy, or electroporation energy). Optionally, the first therapeutic energy generator is a generator of energy selected from ablation energy, cutting energy, and thermal energy. Optionally, the first therapeutic energy generator is a generator of energy selected from RF energy, sonic (e.g. ultrasound) energy, microwave energy, laser energy, cryoablation energy, plasma energy, electroporation energy, and high intensity focused ultrasound (HIFU) energy.

Optionally, the first memory device comprises the control instructions for controlling the secondary device. Additionally or alternatively, the secondary device optionally comprises a second memory device comprising control instructions for controlling the secondary device, optionally wherein the second memory device is reversibly linked to the first controller.

Optionally, the secondary device comprises any I/O device that transmits (i.e. sends and/or receives) data or analog signals to or from a controller. Optionally said controller is the first controller (e.g. controller 1/pressure sensor depicted in FIG. 9) or a second controller in communication with the first controller (e.g. controller 2/vaporizer depicted in FIG. 9). Optionally, the I/O device is reversibly linked to the first controller (e.g. by a second reversible connector), e.g. the sensor depicted in FIG. 7, the fluid pump or sensor depicted in FIG. 8, the pressure sensor depicted in FIG. 9, or the vaporizer depicted in FIG. 9 when the communications link comprises a reversible communications link. Optionally, the I/O device is reversibly linked or non-reversibly lined to a second controller (e.g. the vaporizer depicted in FIG. 9, or the imaging device depicted in FIG. 10), wherein the second controller is reversibly linked to the first controller (e.g. by a reversible data link connector such as an Ethernet cable).

Optionally, the secondary device comprises a second memory device (e.g. memory device 2 of FIG. 8, FIG. 9, or FIG. 11). Optionally, the second memory device comprises instructions for controlling the secondary device, instructions for controlling the therapeutic device, instructions for controlling the first console, or instructions for controlling an optional second console to which the secondary device is operably linked.

Optionally, the secondary device comprises an I/O device that provides a therapeutic or diagnostic function ('d/t device').

Optionally, the secondary device comprises an I/O device selected from a second energy generator, a user interface ('UI'), and an intermediate device.

Optionally, the secondary device comprises a second energy generator, wherein the second energy generator is a generator of a diagnostic energy or a therapeutic energy. Optionally, the secondary device comprises a second controller configured to control the second energy generator, e.g. provided together in a second console. Optionally, the second energy generator is reversibly linked to a second operational head configured for transmitting the output of the second energy generator to a target tissue (e.g. the same or different target tissue as the output of the first energy generator) e.g. as depicted in FIG. 9. Optionally, the secondary device is reversibly linked to the first console (e.g. the irrigation device depicted in FIG. 8). Optionally, the secondary device comprises a second memory device that is reversibly linked to the first console (e.g. the second memory device depicted in FIG. 8 or FIG. 9, noting that the second memory device in FIG. 9 is indirectly linked to the first console through the second console).

Optionally, the second energy generator is a generator of therapeutic energy. Optionally, the second energy generator is a generator of therapeutic energy selected from electromagnetic energy (e.g. RF energy, microwave energy, and laser energy), mechanical energy (e.g. sonic energy, irrigation or fluid pump, or pneumatic pressure), thermal energy (e.g. heat ablation), freezing energy (e.g. cryosurgery energy) and electrical energy (e.g. electrocautery energy, electrosurgery energy, or electroporation energy). Optionally, the second energy generator is a generator of therapeutic energy selected from ablation energy, cutting energy, and thermal energy. Optionally, the second energy generator is a generator of therapeutic energy selected from RF energy, sonic (e.g. ultrasound) energy, microwave energy, laser energy, cryoablation energy, plasma energy, electroporation energy, and high intensity focused ultrasound (HIFU) energy.

Optionally, the second energy generator is a generator of diagnostic energy. Optionally, the diagnostic energy is imaging energy such as electromagnetic imaging energy (e.g. RF imaging energy or X-ray imaging energy), magnetic energy (e.g. as In magnetic resonance imaging ('MRI'). or sonic energy (e.g. as in ultrasound imaging).

Optionally, the secondary device comprises a UI. Optionally, the UI comprises a display, a speaker, or both. Optionally, instructions for controlling the secondary device comprise instructions to provide the user with feedback, optionally wherein the feedback is selected from: feedback from a temperature sensor or other sensor, connection status of the therapeutic device to the first console, authenticity of the therapeutic device, and use data of the therapeutic device. Optionally, the instructions for controlling the secondary device comprise labels, screens, fields, or workflows to be displayed or otherwise presented to a user. Optionally, instructions for controlling the UI are provided on the first memory device.

Optionally, the secondary device is an intermediate device (e.g. as depicted in FIG. 11). According to the present invention an intermediate device is any device comprising an a member configured to transmit energy output between a generator and an energy delivery head ('extension'), wherein the device comprises at least two connectors operably linked to the extension, wherein one of said connectors is configured for coupling to the console (or a serially linked intermediate device of a chain of two or more intermediate devices between the console and the therapeutic device). and the other of said connectors is configured for coupling to the therapeutic device (or a serially linked intermediate device). Optionally, the intermediate device comprises a memory device. Optionally, the memory device of the intermediate device comprises instructions for controlling the console (or energy generator thereof). For example, the instructions can comprise algorithms that are useful with the intermediate device or parameters of the intermediate device. Examples of useful parameters of the intermediate device include calibration parameters (e.g. impedance, loss factors, or frequency characterization), capability parameters (e.g. compatible or incompatible modes of operation, compatible or incompatible therapeutic devices; compatible or incompatible consoles or energy generators), and verification parameters (e.g. use data of the intermediate device, recommend number of uses of the intermediate device, authentication of the intermediate device, re-use prevention rules of the intermediate device, or sterilization validity information of the intermediate device). Optionally, the extension has a length greater than any of 30 cm, 60 cm, 90 cm, 120 cm, 150 cm, 300 cm, 500 cm, 1 m, or 2 m.

Optionally, the secondary device comprises a d/t device. Optionally, the d/t device is a diagnostic device selected from a sensor (e.g. as depicted in FIG. 7) and an imaging device (e.g. as depicted in FIG. 8). Alternatively, the d/t is an I/O device that provides a therapeutic function (e.g. the fluid pump depicted in FIG. 8 or the vaporizer depicted in FIG. 9).

Optionally, the secondary device comprises one or more sensors selected from a temperature sensor, a force sensor, an air pressure sensor, a heart rate sensor, an ECG sensor, an EEG sensor, an EMG sensor, an EOG sensor, and a respiration sensor. Optionally, the secondary device comprises an imaging device. Optionally, the secondary device comprises an imaging device and the first energy generator is a generator of therapeutic energy such as heating, freezing, cutting, or ablation energy (e.g. RF energy, sonic energy, microwave energy, and laser energy, cryoablation energy, plasma energy, electroporation energy, or high intensity focused ultrasound (HIFU) energy). Optionally, the imaging device is configured or used for imaging the energy delivery head of the first therapeutic device.

Optionally, the secondary device comprises an imaging device and the first energy generator is a generator of therapeutic energy such as heating, freezing, cutting, or ablation energy, and the first memory device comprises parameters of the first energy delivery head (e.g. parameters of an ablation electrode or tissue-contacting component) that can be correlated with feedback from the imaging device (e.g. length, area, mass, orientation, volume, opacity, or antenna coupling coefficient of the first energy delivery head). Optionally, the imaging device is configured or used for imaging the energy delivery head of the first therapeutic device. For example, the system can be configured to perform a method (e.g. via an algorithm provided on the memory device of the first therapeutic device, a memory device of the secondary device, or a console memory device) or a memory device of the first console) comprising the steps of a) obtaining the parameters of the first energy delivery head, b) obtaining imaging feedback from imaging device; and c) correlating or modifying the imaging feedback based on one or more of said parameters of the first energy delivery head, and optionally presenting said feedback on a display, and optionally wherein said feedback or presentation on a display comprises a lesion calculation, e.g. a calculation selected from lesion size, lesion shape, lesion position, amount of energy absorption by a tissue, and effect of a combination of energy from optional multiple electrodes.

Optionally, the secondary device comprises an imaging device and the first energy generator is a generator of therapeutic energy such as heating, freezing, cutting, or ablation energy, and the system is configured for transmitting feedback from the imaging device to the first controller (e.g. via an algorithm provided on the memory device of the first therapeutic device, a memory device of the secondary device, or a console memory device). Optionally, the imaging device is configured or used for imaging the energy delivery head of the first therapeutic device. Optionally, the imaging feedback transmitted from the imaging device to the first controller comprises spatial or tissue characterization information. Optionally, the first controller is configured to modulate the energy output or select or modify algorithms for energy output (e.g. via an algorithm provided on the memory device of the first therapeutic device, a memory device of the secondary device, or a console memory device) based on the transmitted imaging feedback.

Optionally, the secondary device comprises an imaging device and the first energy generator is a generator of therapeutic energy such as heating, freezing, compression, cutting, or ablation energy, wherein the first controller is configured for obtaining the parameters of the first energy delivery head and modifying or selecting treatment algorithms stored on the first memory device or a console memory device based on the obtained parameters.

Optionally, the secondary device comprises an imaging device and the first energy generator is a generator of therapeutic energy such as heating, freezing, compression, cutting, or ablation energy, wherein the first memory device comprises parameters of the first energy delivery head. Optionally, the parameters of the first energy delivery head are selected from length, area, mass, orientation, volume, opacity, antenna coupling coefficient. Optionally the parameters of the first energy delivery head are selected from size, distance, surface area, impedance, calibration and correction factors, coupling factors, frequency-specific characterizations, resonant frequency, and opacity.

Optionally, the first energy output is a therapeutic energy and the secondary device comprises a sensor of an effect (e.g. biological effect or environmental effect) of the therapeutic energy. For example, the therapeutic energy can be ablation or heating energy (e.g. RF energy, sonic energy, microwave energy, and laser energy, cryoablation energy, plasma energy, electroporation energy, and high intensity focused ultrasound (HIFU) energy) and the effect can be any of temperature, a heart rate, an ECG, an EEG, an EMG, an EOG, and a respiration rate. Optionally, the first memory device comprises instructions for obtaining feedback (e.g. digital or analog feedback) from the sensor and controlling the first energy output based on the obtained feedback (e.g. terminating or down-modulating energy feedback if temperature exceeds a temperature limit). Optionally, the first memory device comprises at least one target parameter of the sensor feedback (e.g. acceptable range of sensor readings, limits of sensor readings), optionally wherein said target parameter is a trigger for one or more control instructions of the first energy generator (e.g. initiation, termination, or modulation of energy output).

Optionally, the secondary device comprises a d/t device that provides a therapeutic function. Such a d/t device can be any I/O device that provides a therapeutic function. Optionally, the d/t device comprises a therapeutic I/O device selected from a fluid pump, a vaporizer, a ventilator, or any other therapeutic energy generator.

Optionally, the secondary device comprises a fluid pump reversibly linked to the first controller (e.g. by a second reversible connector). Optionally, the fluid pump is reversibly linked to a second energy delivery head (e.g. cannula such as a cannula of an irrigated ablation catheter), for example by a third reversible connector. Optionally, the secondary device comprises a second memory device comprising instructions for controlling the fluid pump (e.g. fluid pump parameters, or algorithms for controlling the fluid pump, e.g. based on temperature or other sensed or calculated parameters such as image contrast (e.g. the amount of contrast agent or the need for more or less imaging contrast agent irrigated by the fluid pump). Optionally, the first memory device comprises instructions for controlling the fluid pump (e.g. algorithms such for controlling the fluid pump, e.g. based on temperature or other sensed or calculated parameters). Optionally, the first memory device comprises an algorithm for controlling the fluid pump (e.g. a set of instructions comprising one or more steps of pumping fluid, e.g. based on a sensed parameter such as temperature or a calculated parameter) and the second memory device comprises parameters of the fluid pump (e.g. calibration parameters used by the first controller to operate the fluid pump according to the algorithm). Optionally, the fluid pump is further linked to a reservoir (e.g. for holding coolant, a contrast agent, or any fluid) such that fluid can be transmitted between the reservoir and the second energy delivery head.

Optionally, the secondary device comprises a second energy generator and a second energy delivery head reversibly linked thereto (e.g. as depicted in FIG. 9). Optionally, the secondary device comprises a second memory device (e.g. comprising instructions for controlling the secondary device). Optionally, the secondary device comprises a therapeutic device comprising the second energy delivery head and a second memory device (e.g. as depicted in FIG. 9). Optionally, the second memory device is reversibly linked to the first controller (e.g. as depicted in FIG. 9). Optionally, the secondary device comprises a second controller configured for control of the second energy generator and the second memory device is reversibly linked to the second controller (e.g. as depicted in FIG. 9). Optionally, the second energy delivery head is reversibly connected to the first controller, for example, by a reversible connecter positioned between the second energy delivery head and the first controller; or by a reversible connecter positioned between the first controller and a second controller, wherein the second energy delivery head is reversibly or non-reversibly linked to the second controller and/or a second energy generator controlled by the second controller.

Optionally, the secondary device comprises 1) a second console comprising a second energy generator and a second controller; and 2) a second therapeutic device comprises a second memory device and a second energy delivery head, wherein the second energy delivery head and the second memory device are reversibly linked to the second console (e.g. by reversible energy delivery linkage and reversibly memory linkage, respectively), and wherein the first console is reversibly or non-reversibly linked to the second console (e.g. a data link connecting the first controller and second controller), for example as depicted in FIG. 9. For example, in addition to the first console and first therapeutic device, the system comprises a secondary device, wherein:
  a. a secondary device comprises:
    i. a second console comprising a second energy generator and a second controller configured for controlling the energy output of the second energy generator ('second energy output');
    ii. a second therapeutic device comprising:
      a) a second energy delivery head configured for transmitting the second energy output to a target site; and
      b) a second memory device comprising control instructions for said controlling the second energy output;
    iii. a second reversible connector configured for operably linking the second energy generator to the second energy delivery head; and
    iv. a second reversible memory operable linkage configured for operably linking the second memory device to the second controller; and
  b. the system comprises a data link connecting the first controller and the second controller.

In any system comprising a plurality of generators such as a first energy generator and a second energy generator, the two energy generators can be any combination of energy generators. Optionally, the two energy generators are any two energy generators that provide simultaneous or other coordinated therapy and/or diagnostic function. Optionally, the system is configured or used for targeting the energy output of the two energy generators to the same target site. Optionally, the first and second energy generators can be a therapeutic energy generator and an imaging energy generator. As another example, the first and second energy generators can each be therapeutic energy generators (e.g. a first and second ablation or heat energy generators). Optionally, the first and second energy generators are any combination listed in Table 1.

TABLE 1

| Energy Generator Combinations | |
|---|---|
| First | Second |
| heat or ablation energy generator | imaging energy generator |
| heat or ablation energy generator | fluid pump |
| ventilator | vaporizer |

Optionally, the secondary device comprises a second energy delivery head. In such an embodiment, the first energy delivery head and the second energy delivery head are optionally comingled together and/or configured to transmit the respective energies to the same target site. Examples of a shared target site include a body cavity, a body lumen, and an organ. Examples of comingled energy delivery heads include a) a catheter, or other operational device, comprising an energy delivery electrode as a first energy delivery head (e.g. for transmitting ablation energy to a target site) and a cannula as a second energy delivery head (e.g. a cannula configured for irrigating fluid to and/or from the target site, e.g. an open or closed loop irrigation catheter); b) a patient tube circuit or facemask as a first energy delivery head (e.g. for transmitting pneumatic energy from a ventilator) and, as the second energy delivery head, an inlet (e.g. port for introduction of gas or vapor) to the patient tube circuit or facemask. Similarly, a sensory head (e.g. a temperature sensor or contact force sensor) of a secondary device can also be comingled with the first energy delivery head and/or configured sense an environmental or biological effect at the target site, for example, a catheter comprising energy delivery electrodes and one or more sensors.

Configuration Management Software

Optionally, a system of the invention comprises configuration management software. According to the present invention, 'configuration management software' is any software configured to obtain data from two or more of memory devices of the system, and provide a set of control instructions for a therapeutic procedure using less than all of said data. At least one of said memory devices is a reversibly connected memory device (e.g. memory device of a reversibly connected therapeutic device or secondary device). Optionally, at least two of the two or more memory devices are reversibly connected memory devices. An example of a system comprising configuration management software is detailed in Example 19

Optionally, the configuration management software is provided on a memory device local to the console. Alternatively, the configuration management software can be provided on the memory device of a reversibly connected therapeutic device or secondary device and uploaded or run on the console controller.

Optionally, the set of control instructions for a therapeutic procedure comprises an algorithm (e.g. a treatment algorithm), one or more parameters, or a controller software update.

Optionally, the configuration management software configured for interpreting and/or implementing, said data.

Optionally, the data comprises a set of control instructions from each of the two or more of memory devices.

Optionally, the configuration management software is configured for conflict resolution between two sets of control instructions. Optionally the conflict resolution comprises identifying an inconsistent or incoherent combination of the at least two sets of control instructions and providing a set of control instructions for a therapeutic procedure, for example, by selecting a set of control instructions from the two sets of control instructions or selecting portions from the two sets of control instructions. Optionally, the inconsistent or incoherent combination of control instructions are inconsistent or incoherent combination of parameters (e.g. different target values of a parameter such as when a first set of control instructions comprise a target temperature that is different from a target temperature provided by a second set of control instructions). Optionally, the inconsistent or incoherent combination of the at least two sets of control instructions comprises any of:
 a. control instructions provided on two respective memory devices, each containing a software update for one or more consoles which are different from the other;
 b. control instructions provided on two respective two memory devices, each containing settings or algorithms which are different from the other;
 c. first control instructions provided on a reversibly connected memory device which contain settings for a device, and a console memory device which also contains second control instructions comprising settings for said device which are different than the settings of the first control instructions;
 d. first control instructions provided on a reversibly connected memory device contains a first software version for the console, and a console memory device which contains a second software version for the console, wherein the second software version is a more recent version than the first software version;
 e. control instructions provided on a reversibly connected memory device comprising a first software version for the console, and control instructions provided on another memory device which comprise a second software version for the console, wherein the first software version is different than the second software version;
 f. control instructions provided on a reversibly connected memory device which specify use with an compatible connected device or console, wherein the system comprises a connected device or console other than said an compatible connected device or console;
 g. control instructions provided on a memory device that contains a list of one or more compatible therapeutic devices, sensory devices, or console, wherein said system includes a therapeutic device, sensory device, or console that is not provided in the list;
 h. control instructions provided on a memory device that contains a list of one or more incompatible therapeutic devices, sensory devices, or console, wherein said system includes a therapeutic device, sensory device, or console that is provided in the list;
 i. control instructions provided by respective memory devices that comprise non-redundant control instructions or parameter.
 j. control instructions provided by respective memory devices, wherein at least one of the sets of control instructions comprises less than a full set of instructions required to perform a therapeutic procedure
 k. control instructions provided by respective memory devices, wherein at least one of the control instructions reference a console, therapeutic device, or secondary device which is not connected to the system.

Optionally, the configuration management software is configured for obtaining data (e.g. software, parameters, or algorithms) from the at least two memory devices determining the most-appropriate combination of data to use for a therapeutic procedure.

Optionally, the configuration management software is configured to obtain one or more business rules or clinical rules from at least one memory device. Optionally, the one or more business rules or clinical rules are selected from:
 a. an identification of combinations of other devices are compatible with a particular device;
 b. an identification of which software is compatible with device combinations;
 c. instructions for selecting a software version from one of the memory devices
 d. instructions to downgrade console software or to utilize newer software provided by a reversibly connected memory device when a console's memory device contains more-recent software or information than that specified by any currently connected reversibly connected memory device;
 e. an override rule, optionally wherein said override rules an override configured to run when instructions on a reversibly connected memory device indicate that its respective therapeutic device or secondary device has use limits, optionally wherein the override rule specifies whether treatment can proceed if a device has met or exceeded its use or re-use limit
 f. an error-processing rule, optionally wherein the error-processing rule specifies if treatment can initiate when memory is not present in a reversibly connected device, or the memory cannot be read;
 g. a data-write rule, optionally wherein the data-write rule specifies which memory device, should be written with data or feedback from the current therapeutic procedure and
 h. a display rule, optionally wherein the display rule specifies the information that is displayed to the user for a given combination of devices.

Optionally the configuration management software is configured for ranking two or more memory devices, or control instructions provided thereby, and selecting data associated with a higher ranking. Optionally, ranking is based on any of: software version or date, device capabilities, region or geographic region, and user selection.

Other Optional Configurations

Isolation Barrier

A system of the present invention optionally comprises an alternating current (AC) user interface (e.g. display) and/or other high voltage device in the console, wherein the memory of the therapeutic device comprises an electrical linkage (e.g. memory wires) to the console or high voltage device thereof, and the system further comprises an isolation barrier between high voltage device and the energy (e.g. RF) output operable linkage.

The mechanics of placing a memory device within a patient-applied therapeutic device can sometimes produce s electrical safety concerns. Frequently RF Generators are powered via AC Outlets or otherwise connected to other equipment which does so. The patient can optionally be protected from such voltages. For example, the memory wires can ultimately be connected to the UI system because that system optionally requires a large part of the data which could be stored on the memory, and is optionally at the 'top' of the computing/control hierarchy. The UI may not, however, provide enough isolation from AC to be connected to a patient. Thus, the memory wires can optionally be positioned an effective distance away from the patient applied energy output operable linkage (i.e. using a large connector providing an insulation barrier), as depicted in FIG. 4a, or an additional level of isolation is optionally provided. This additional level of isolation optionally comprises an electronic isolation barrier, e.g. as depicted in FIG. 4b, such as opto-isolators, transformers, MEMS-based electromagnetic couplers, or a combination thereof.

Methods

A system of the present invention can be used in any therapeutic procedure.

Optionally, the therapeutic procedure is an RF procedure. The RF procedure can be any procedure that utilizes RF energy to provide a therapeutic effect.

Optionally, the therapeutic procedure is a heating procedure such as RF heating or other heating energy. Optionally, the heating procedure is an ablation procedure, a cutting procedure, a coagulation procedure, an occlusion procedure, or a procedure that induces or modulates metabolic processes in a target tissue.

Optionally, the therapeutic procedure is an RF procedure selected from: vision correction (e.g. to reshape a cornea), tumor ablation, sleep apnea treatment (e.g. use of RF energy to reduce volume of tongue), snoring treatment (e.g. RF energy delivered by a thin probe through the lining of the palate into the deeper tissues, creating a lesion that reduces the volume of soft tissue and elevates the palate), cosmetic surgery (e.g. RF energy delivered for the treatment of skin in dermatology and plastic surgery applications, e.g. to tighten and/or conform skin by thermal restructuring of the dermal collagen matrix with stiffening), reduction of an enlarged prostate, treatment for rapid heartbeat syndrome, tightening loose joints, treatment of varicose veins, treatment of back pain, treatment of incontinence, a pain management procedure, a cardiac procedure (e.g. to destroy abnormal electrical pathways contributing to cardiac arrhythmia), a tumor reduction or removal procedure, and a dermatology procedure such as skin resurfacing.

Optionally, the RF procedure is an RF ablation procedure. The RF ablation procedure can be any procedure that kills cells by application of RF energy. Optionally, the procedure is a nerve ablation procedure or a tumor ablation procedure (e.g. Lung, kidney, breast, rectal, colon, bladder, esophageal, brain, pancreatic, skin, cervical, ovarian, prostate, stomach, lymphatic, bone or liver tumor). Optionally, the procedure ablates an electrical pathway that enables an undesirable condition (e.g. atrial fibrillation).

Optionally, the RF procedure is a nerve ablation procedure. Optionally, the nerve ablation procedure is used to treat pain, e.g. by destroying the ability of a nerve to transmit pain signals. Optionally, the nerve is a nerve surrounding the facet joints on either side of the lumbar spine. Optionally, the procedure comprises ablating sympathetic nerves to affect a change in physiologic parameter (e.g. renal nerve ablation).

Optionally, the RF procedure comprises delivering RF energy to a target tissue selected from: brain, elbow, eyes, heart, kidney, knee, liver, nose, ovary, prostate, spine, and tongue.

Optionally, the RF procedure comprises delivering RF energy to impart any of: ablation, rhizotomy, coagulation cauterization, and lesioning at a target site.

Systems of the present invention can be configured to perform any of the therapeutic procedures taught herein. For example, the controller, RF generator, and therapeutic device can be specifically configured to perform any of the therapeutic procedures. With the teachings provided herein, one skilled in the art can readily provide such configurations.

Superior Properties

Systems of the present invention provide one or more superior properties. For example, the system can have any of the following properties:

no longer require salespeople, biotechs or other personnel to carry a software upgrade to the RFG;

no longer are forced to develop, build and certify an entirely new software release for each new catheter or device—the necessary incremental additions come with the catheter. This means a significant reduction in cost for medical device equipment manufacturers for building and releasing new software releases for each new treatment.

A major reduction in time-to-market for new treatments no longer require a separate RFG for each new clinical treatment (i.e. a pain generator, an asthma treatment generator, a renal denervation generator, a facial nerve (glabella furrowing) generator, etc. One generator does all of these treatments with the specific control software and user interface software stored in the catheter. The generator could be wheeled from the interventional radiology suite over to the neurosurgery suite with no modification other than plugging in the appropriate catheter for the appropriate procedure.

A drastic reduction in capital equipment costs for the hospitals since the same RFG can be used for multiple different procedures where it current requires a different RFG for each procedure.

A drastic reduction in the cost of sustaining, maintaining and servicing RFGs in hospitals and doctors' offices.

A new capability for removing the connector portion of the catheter and sending it back to the manufacturer as a part of a verification and maintenance program.

An increase in the amount of reuse of design elements, documentation, and testing in new applications, increasing the reliability of new applications, and reducing the regulatory burden of bringing new applications to market.

A new capability to determine whether an energy generator such as an RF generator ('RFG') may contain a latent defect introduced inadvertently into the production process and then to "disable" the RFG from further use for patient safety.

A drastic reduction in the business risk of having new and innovative therapeutic devices copied and sold by unauthorized agents.

EXAMPLES

Example 1 Therapeutic System

Figure 5:
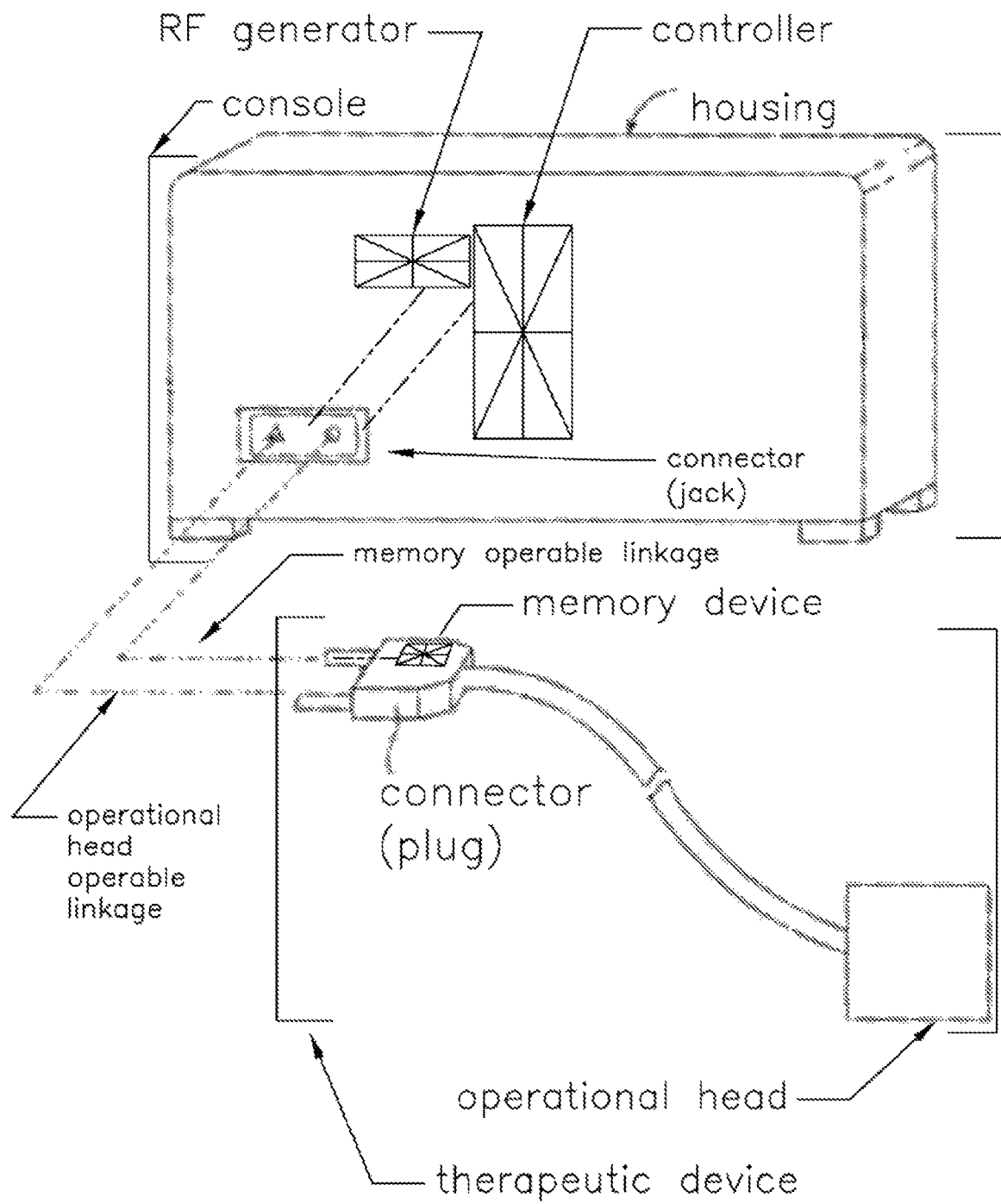
FIG. 5 depicts an examplary system of the present invention.

FIG. 5 depicts one embodiment of the present invention. The system comprises
a. a console comprising an RF generator and a controller configured for controlling the RF output of the RF generator;
b. a therapeutic device comprising:
  i. an operational head configured for receiving the RF output and delivering RF energy to the biological tissue; and
  ii. a memory device comprising control instructions for said controlling the RF output; and
c. a reversible connector configured for operably linking:
  i. the RF generator to the operational head; and
  ii. the memory device to the controller.

The connector on the console side comprises a jack. The connector on the therapeutic device side comprises a plug configured for the jack.

The operational head comprises an RF ablation head comprising a pair of electrodes configured in monopolar or bipolar mode. The operational head is configured as, e.g. a handpiece comprising an RF ablation catheter and/or needle.

The memory operable linkage comprises a communications bus for linkage of the memory to the controller. The operational head operable linkage comprises a pair of electrical wires for linkage of electrodes on the operational head to the electrodes of the RF generator.

The memory device can be provided anywhere on the therapeutic device, for example, in or on the connector (plug) of the therapeutic device.

Figure 1B:
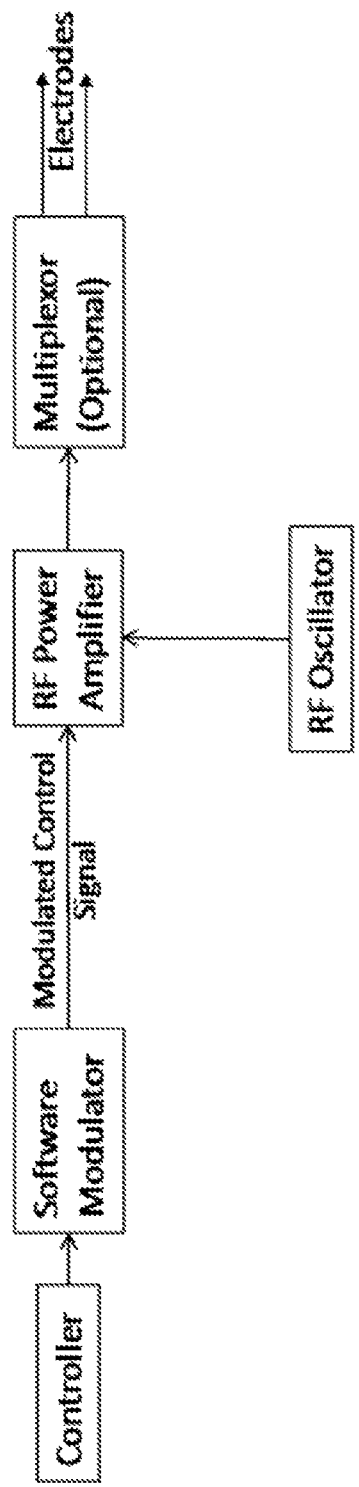

As depicted in FIG. 1A, the RF generator comprises an RF oscillator, an amplitude modulator, and a pulse modulator configured for control by the controller. Optionally, as depicted in FIG. 1B, the RF generator may be comprised of an agile RF generator from which the signal can be modulated by modulating the controlling signal rather than modulating the RF signal.

Upon connection of the therapeutic device, the controller reads the control instructions stored on the memory device and controls the RF generator in the manner indicated by the control instructions. The control instructions comprise an algorithm or a set of parameters specific to the therapeutic device or a therapeutic procedure for which the therapeutic device is configured.

The control instructions also comprise instructions for controlling a user interface, e.g. displaying information on the screen of the console including measured or monitored parameters, location and size of parameters, update rates of parameters. Further, the control instructions comprise the workflow of the generator, comprising the order of screens displayed, the information which is to be entered by the operator, the controls and conditions which must be activated and present in order to progress to a next state of the workflow. Such states may comprise of a standby state where the operator is asked to connect the therapeutic head, a programming state where the operator may adjust treatment parameters, patient information, or the user-interface preferences, a ready state where the generator is prepared to treat and is waiting for appropriate sensed conditions or activation of a control by the operator, a treatment state where energy is being delivered according to the algorithm specified by control instructions, an warning state where treatment continues but is approaching conditions which would cause treatment to stop, an alert state where the generator halted energy delivery because of inappropriate conditions of RF or a sensor input, an alarm state where the operator should take immediate action to prevent harm to the patient, and an error state where a fault with the generator or connected therapeutic device has been detected.

Figure 2:
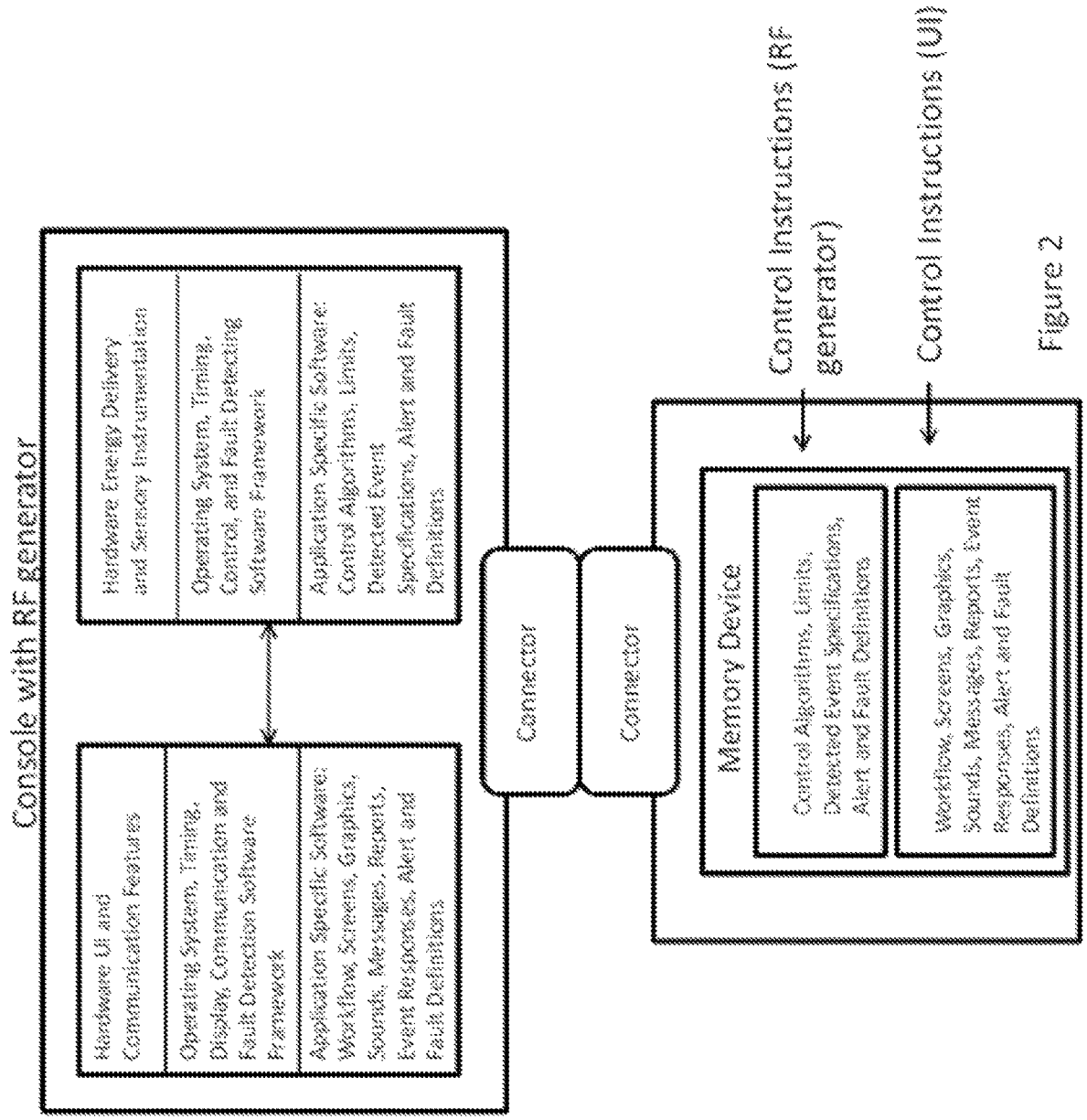
FIG. 2 depicts an examplary system of the present invention.
Figure 3:
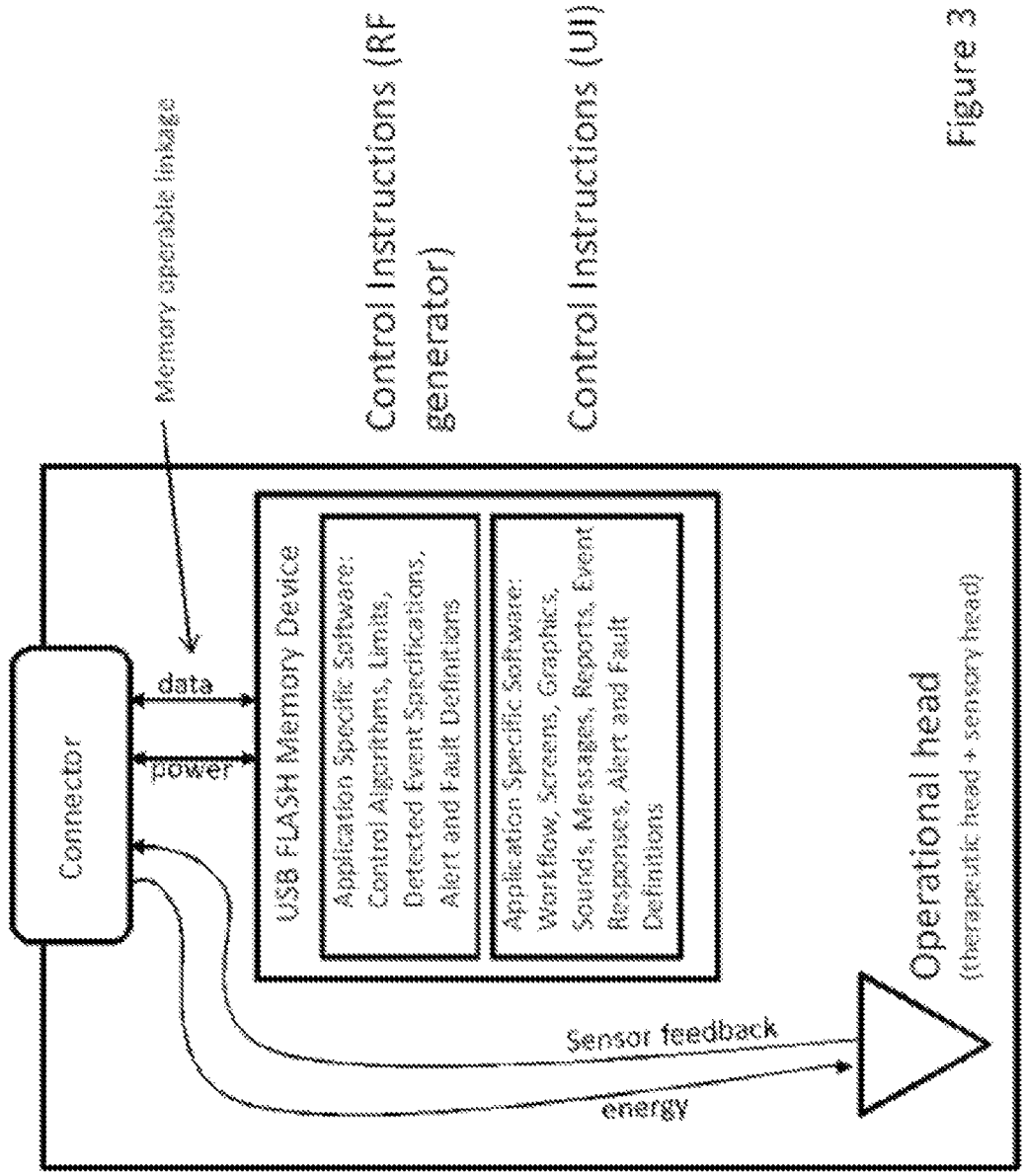
FIG. 3 depicts an examplary therapeutic device useful in the present invention.
Figure 6:
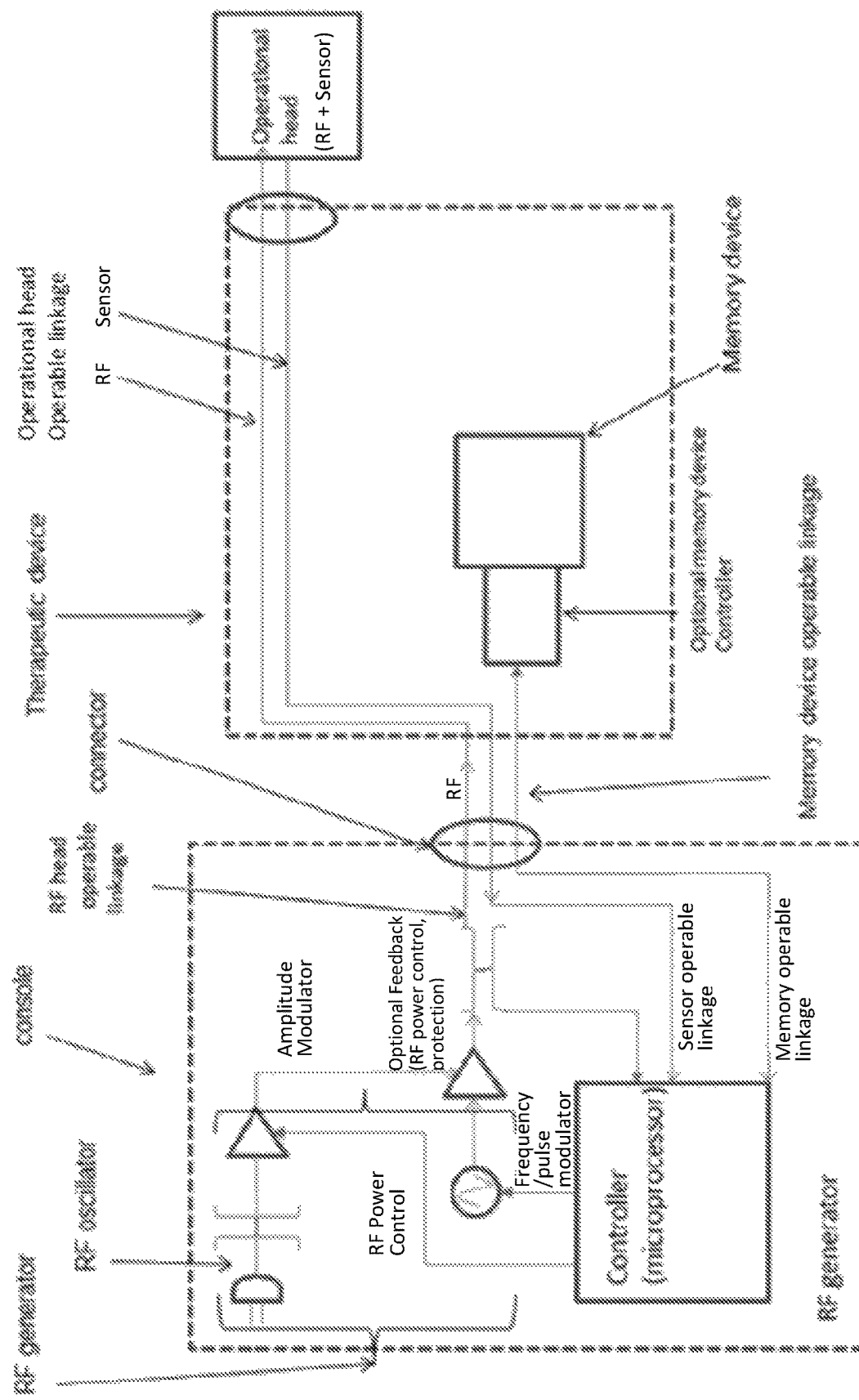
FIG. 6 depicts an examplary system of the present invention.

Optionally, the system is configured depicted in the graphical representation of FIG. 2. Optionally, the therapeutic device of the system is configured as depicted in the graphical representation of FIG. 3. Optionally, the system is configured as depicted FIG. 6.

Example 2 Therapeutic System

A system of the invention (e.g. as detailed in Example 1) is provided, wherein the control instructions contain the specifications of energy parameters (e.g. power, voltage, waveshape, duty cycle, frequency, pulse frequency, pulse duration, impedance targets, and power adjustments to apply in response to impedance changes) for the RF energy to be applied to the treatment site to cut or ablate physiological structures.

The power delivered by the energy generator is optionally specified to vary based on detection of rapid impedance changes, such as could be the case when localized boiling or 'popping' occurs. The control instructions optionally further specify impedance readings or trends which provide indications of proper or improper contact of electrodes to physiological structures. The control instructions optionally contain information as to how this information is to be displayed by the generator, containing characteristics such as text size, graph axes, update rate, filtering to be applied, colors to be used, units to be displayed, precision to be displayed, acceptable ranges of values to be displayed textually or graphically, and display and conditioning of sensor signals to trigger alarms or alerts. The control instructions optionally specify the parameters to be displayed on the screen during treatment, shown in a post-procedure report, contained in data log files, viewable over a connected web device, or any combination thereof.

Example 3 Therapeutic System

The system detailed in Example 2 is optionally further provided with one or more temperature sensors configured detect the changes in temperature of the electrode(s). The sensory input of the temperature sensors is used to limit the duration of treatment, alter the energy applied, or otherwise inform the operator of said temperatures. This function is provided by parameters in the memory device, e.g. minimum and maximum temperature limits, limits based on the rate of change of temperature, amount of alteration the energy delivery based on the temperature response observed at the electrodes, allowable ranges of thermal impedance (e.g. change in temperature as it relates to the rate or total quantity of energy delivered, or temperature response when energy is increased, reduced, or removed).

Example 4 Therapeutic System

The system detailed in Example 3 is optionally further configured such that at least one of the temperature sensors is used to provide closed-loop temperature control of the electrodes. Here additional parameters contained in the control instructions specify how temperature is controlled, based on parameters such as target temperature or cumulative degree-seconds of ablation energy. Additionally the target temperature is optionally adjusted based on impedance changes which are indicative of changes in the tissue or tissue-electrode interface.

Example 5 Therapeutic System

The system detailed in Example 2, Example 3, or Example 4 is optionally further configured to provide where a lumen or cannula for the application of fluid to the target ablation site to supplement the conductivity between the electrodes and the tissue. Here, additional parameters contained within control instructions specify the fluid flow, such as flow rate, pressure, target impedance, and target temperature.

Example 6 Therapeutic System

The system detailed in Example 2, Example 3, or Example 4 is optionally further configured to provide where a lumen or cannula for the application of fluid to cool the target ablation site. Here, additional parameters contained within control instructions specify the fluid flow, such as flow rate, pressure, target impedance, and target temperature.

Example 7 Therapeutic System

The system detailed in Example 6 is optionally further provided with additional lumens or cannulas for aspiration of the cooling fluids. Here, additional parameters contained in the control instructions specify the operations of the aspiration, such as negative pressure (vacuum), flow-rate, or temperature Example 8 Therapeutic System The system detailed in Example 7 is optionally further configured such that the injection (i.e. infusion or irrigation) and aspiration of fluids are contained within a balloon or cavity within the therapeutic head and returned via aspiration to without contact with the targeted tissue.

Example 9 Therapeutic System

The system detailed in any of Example 2 through Example 8 is optionally further provided with an ECG is sensor. The ECG sensor is provided either through an RF electrode, or via a separate sense electrode, or via additional therapeutic heads or therapeutic devices connected to the console. The ECG can be used for the purpose of synchronizing RF with cardiac activity. Here the control instructions contain information specifying the ECG morphological features to which RF should be synchronized, or detect that conditions are improper to deliver RF energy based on ECG rate or morphological features Example 10 Therapeutic System The system detailed in any of Example 2 through Example 8 is optionally further provided with a fiber-optic lumen contained within the therapeutic device which conveys spectral information from which the chemical composition of ablation products can be monitored. Here the control instructions contain information which specified the spectrum of said products as well as the parameters and algorithms by which this information would affect energy delivery.

Example 11 Therapeutic System

The system detailed in any of Example 2 through Example 10 is optionally further provided with a force sensor, active in one or multiple axes, configured to measure the application force of electrode(s) against a physiological structure at the target site. Here the control instructions comprise parameters such as contain force, frequency response, or time parameters which indicate proper/improper contact pressure, physiological pressure such as blood pressure, physiological pressures resulting from motion, such as cardiac contraction or respiration.

Example 12 Therapeutic System

The system detailed in any of any of the previous examples is optionally provided with any of the following configurations:
  a. The operational head comprises:
    i. a monopolar needle
    ii. a bipolar needle
    iii. an array of needles connected in a monopolar fashion
    iv. an array of needles connected in a bipolar fashion
    v. an array of needles connected to more than one RF output.
      a) e.g. configured to combine bipolar and monopolar energy in a phased array;
    vi. a balloon device containing one or more electrodes on its surface.
    vii. a mesh or basket which expands to contact physiological tissue at the target site
    viii. an integrated lighting device;
    ix. an integrated lighting device and an imaging device.

Example 13 Therapeutic System

A therapeutic system is provided, as depicted in FIG. 7. The system comprises
  a. a console comprising an energy generator (e.g. RF generator) and a controller configured for controlling the energy output of the energy generator;
  b. a therapeutic device comprising:
    I. an operational head comprising:
      i. an energy delivery head configured for transmitting the energy output to biological tissue; and
      ii. at least one sensor;
    II. a memory device comprising control instructions for said controlling the energy output;
  c. a reversible connector configured for operably linking the RF generator to the energy delivery head; and
  d. a reversible memory operable linkage configured for operably linking the memory device to the controller.

The energy delivery head can be any energy delivery head (e.g. RF head) such as an RF ablator, RF catheter, tissue ablator, or nerve ablator.

The reversible connector can comprise a pair of interacting couplers. For example, the interacting couplers can be a jack/plug configuration, wherein the console provides a jack configured to accept a plug provided by the therapeutic device. The reversible connector provides housing for the energy operable linkage (e.g. electrically conductive members that transmit RF signals) that connects the energy generator to the energy delivery head.

As depicted in FIG. 7, the reversible connector can also provide housing for memory operable linkage that comprises a wired linkage, for example, electrically conductive members that transmit data between the memory device of the therapeutic device and the console controller. Alternatively, the memory operable linkage can be a wireless memory linkage such as Bluetooth. In systems with a wireless memory linkage, the controller can be configured to automatically connect to the wireless memory device upon detecting connection of the reversible connector. In either embodiment, the memory device can be optionally be comprised by the therapeutic device-side of the reversible connector, e.g. provided in or on a plug (not shown).

As depicted in FIG. 7, the reversible connector can also provide a housing for sensor linkage (e.g. a pair of wires) which connects the controller to the sensor of the therapeutic device. Alternatively, the sensor linkage can be wireless or can be wired and provided though a second reversible connector.

The sensor can be a temperature sensor or other environmental sensor. The operational head can comprise the sensor in close proximity to the energy delivery head. For example, the operational head can be a catheter with an RF electrode on the outer tip and a sensor in the lumen at the catheter tip.

The system can be is configured to provide feedback to the controller or to the user (e.g. via a display or speaker). For example, the system can provide feedback from the temperature sensor (e.g. the temperature or operation status), connection status (e.g. of the therapeutic device to the console), authenticity of the therapeutic device (e.g. of manufacturer), and use data (e.g. reuse/obsolescence data) of the therapeutic device.

The memory device of the therapeutic device comprises control instructions such that, in operation with the controller, is programmed to deliver a therapeutic profile (e.g. frequencies, amplitudes, crest factors, and/or pulse characteristics). The memory device or controller is further programmed to modify the therapeutic profile (e.g. starting, stopping, or changing energy delivery based on the monitored parameters) based upon feedback, e.g. of connection status, temperature, authenticity of manufacturer and reuse/obsolescence.

The console further comprises a connection for a user input device such as a keyboard. The console further comprises a connection to a data network, such as the Internet, for conveyance of data, e.g. between the manufacturer and the health care provider.

Optionally, the system provides one or more of the following advantageous features:
- Changes in therapeutic profiles, treatment algorithms, or settings can be programmed into the memory device of the therapeutic device, allowing use with a compatible console or RF Generator without the need of a software update.
- User interface changes may be programmed into the memory device of the therapeutic device, e.g. allowing different user-interaction with the system via different labels, instructions, screens, fields, or workflows.
- Therapeutic devices or operational heads thereof can be checked for authenticity, e.g. to prevent the use of counterfeit heads.
- Use data can be stored in the memory device of the therapeutic device and modified to indicate that the therapeutic device has been used, e.g. to prevent use on another patient.
- Calibration information may be stored in one or more therapeutic devices to facilitate more accurate energy delivery and more accurate data collection, including, e.g.
- Operational Head temperature, patient temperature, impedance between one or more pairs of electrodes, rates of cooling, rates of impedance change
- Operation can be prevented when an invalid or unauthentic configuration is detected, providing additional patient safety.
- New therapeutic devices and operational heads may be introduced into the system without prior updates of the console or generator.
- A console may simultaneously support the release of new therapeutic devices or operational heads from different parties without prior knowledge or collaboration by these parties.
- The information in the memory device of the therapeutic device be used may update the software within the. Optionally future attachments of an identical therapeutic Head are then detected more quickly.
- Data collected during the procedure may be stored in the memory device of therapeutic device and returned to the manufacturer for post-treatment analysis, device performance tracking, etc.
- Data from the procedure, including therapeutic head usage and performance data, may be uploaded to the manufacturer for analysis.

Example 14 Therapeutic System

A therapeutic system is provided. The system comprises a console and a therapeutic device e.g. in the manner detailed in Example 13, and further comprises a reversibly connected secondary device (e.g. irrigation device) comprising a reversibly connected memory device. An example is depicted in FIG. 8.

Specifically, the system comprises
b. a console comprising an RF generator and a controller configured for controlling the RF output of the RF generator;
c. a therapeutic device comprising:
  I. an operational head comprising an energy delivery head;
  II. a first memory device comprising control instructions for said controlling the RF output;
d. first reversible connector configured for operably linking the RF generator to the energy delivery head of the therapeutic device;
e. a first reversible memory operable linkage configured for operably linking the first memory device to the controller;
f. an irrigation device as a secondary device comprising:
  I. a fluid pump; and
  II. a second memory device comprising instructions for controlling the fluid pump; and
g. a second reversible memory operable linkage configured for operably linking the first memory device to the controller;
h. second reversible connector configured for operably linking the controller to the fluid pump for control of the fluid pump; and
i. a sensor configured to sense an environmental condition (e.g. temperature) at the operational head.

The fluid pump is configured to deliver and/or collect fluid to/from the biological tissue at the site of the energy delivery, e.g. by providing an irrigation head (e.g. infusion port) about the operational head. Optionally, operational head (e.g. irrigation head) of the fluid pump is comingled with the energy delivery head, e.g. fixed to the energy head and provided with the RF head as a single unit (e.g. to position the fluid pump head with greater precision relative to the RF head). For example, the operational head can be a catheter comprising at the catheter tip an energy delivery electrode, an irrigation port, and optionally a sensor. Alternatively, the operational head of the fluid pump is separated from the RF head (e.g. to provide flexibility in positing the irrigation head).

The fluid is optionally any of a surgical procedure fluid, a cooling fluid, saline irrigation, a contrast agent (e.g. for fluoroscopic visualization), or local fluid (e.g. aspirated fluid from a surgical site). Optionally, the fluid pump comprises a fluid reservoir configured to provide or collect fluid to/from the operational head of the fluid pump.

Optionally, the fluid pump has its own controller that receives data (e.g. commands) from the console controller. Alternatively, the fluid pump optionally comprises a pumping mechanism that is directly powered and/or modulated by the console controller.

The second reversible connector is configured for operably linking the controller to the fluid pump for control of the fluid pump. The operable linkage can be wired or wireless. For example, wired linkage can be used to provide electrical power from the console (e.g. for powering the pumping mechanism) or a data connection between the console controller and an optional fluid pump controller. Wireless linkage can be used, e.g. to provide a wireless data connection between the console controller and an optional fluid pump controller or to provide inductive power to the fluid pump. The second memory device comprises instructions for controlling the fluid pump. For example, the second memory device can contain the specifications or parameters of the pump such that the first memory device can, through the controller, set the operation of the pump to achieve the desired therapeutic profile.

Optionally, at least one of the first and second memory devices can provide control instructions for (e.g. specify actions of) either the therapeutic device, the irrigation device, or both.

Optionally, the system is configured to identify a specific combination of a therapeutic device and a fluid pump (e.g. when a plurality of alternative therapeutic devices and/or fluid pumps is provided). Optionally, at least one of the first and second memory devices comprises instructions specific to the combination of the therapeutic device and the fluid pump. Optionally, the first memory device comprises a plurality of control instructions, each specific to a different fluid pump. Optionally, the second memory device comprises a plurality of control instructions, each specific to a different therapeutic device. Optionally, at least one of the first or second memory device comprises instructions or information of the preferred programming (e.g. identification or ranking for program selections) for either or both of the fluid pump or therapeutic device, e.g. when the two are used in conjunction with each other in a system.

With such as system, many advantages can optionally now be provided. For example: Optionally, the system provides one or more of the following advantageous features:

Therapies requiring new combinations of operational heads may be created without first updating all deployed consoles.

The provided therapy can be selected or modified by whichever memory device contains the most-recent therapy information for the combination of Therapeutic Heads detected at the point of treatment.

Software for both devices (therapeutic device and fluid pump) may be updated as specified by the most-recently manufactured device or operational head thereof.

Delivery of therapy is prevented where an inappropriate combination of devices or operational heads thereof detected.

Data from the procedure may be stored in one or both of the first and second memory devices—allowing one or more parties to perform post-procedure performance review.

Example 15 Therapeutic System

In this example, a system is provided as detailed in Example 14, with the exception that only one of the devices (e.g. therapeutic device or irrigation device) comprises a memory device with reversible operable linkage to the controller. The console recognizes the device that does not have its own reversibly linked memory device (e.g. via an analog or digital ID code) and controls the device.

As one example, the reversibly linked memory device comprises instructions for controlling both devices (e.g. therapeutic device or fluid pump). In this example, the memory device of a single therapeutic device can be used to configure therapy from a plurality of d/t devices. As another example, the console comprises a local memory device (e.g. hard drive) comprising instructions for controlling the device which does not have a reversibly linked memory device.

Similarly, for every embodiment taught herein to comprise a first memory device of a first therapeutic device and second memory device of a secondary device, comprising instructions for controlling the respective devices, the invention also provides an alternative embodiment comprising only one of the first and second memory devices, wherein said one of the first and second memory devices comprises instructions for controlling both the therapeutic device and the secondary device.

Example 16 Therapeutic System

A system of the invention is provided, e.g. as depicted in FIG. 9. The system comprises a first console and a second console. Each console comprises a controller and an energy generator. Each console is reversibly connected to a respective therapeutic device. Each therapeutic device is associated with a respective memory device reversibly linked to the respective controllers. Optionally, the first console and the second console are connected by a communications (i.e. data) link.

As one example, a system is provided comprising:
Specifically, the system comprises:
a. a first console comprising a first energy generator (e.g. ventilator) and a first controller configured for controlling the energy output (e.g. pneumatic energy) of the first energy generator ('first energy output');
b. a first therapeutic device comprising:
  I. a first operational head (e.g. patient tube circuit) configured for transmitting the first energy output to biological tissue (e.g. provides air pressure to the lungs); and
  II. a first memory device comprising control instructions for said controlling the first energy output;
c. a first reversible connector configured for operably linking the first energy generator to the first operational head;

d. a first reversible memory operable linkage configured for operably linking the first memory device to the first controller;
e. a second console comprising a second energy generator (e.g. vaporizer) and a second controller configured for controlling the energy output (vaporized or atomized substances such as water or medicine) of the second energy generator ('second energy output');
f. a second therapeutic device comprising:
  I. a second operational head configured for transmitting the second energy output to biological tissue (e.g. face mask for delivering vaporized substances; or inlet to a patient tube circuit or other vaporizer therapeutic head; and
  II. a second memory device comprising control instructions for said controlling the second energy output;
g. a second reversible connector configured for operably linking the second energy generator to the second operational head;
h. a second reversible memory operable linkage configured for operably linking the second memory device to the second controller; and
i. optionally a communications link connecting the first controller and the second controller.

Optionally, the system comprises a sensor (e.g. pressure sensor) reversibly connected to the first controller.

As one example, the system can have a first console comprising a first energy generator which is a ventilator which applies pneumatic energy to reduce the patient energy required for respiration. A first therapeutic device is provided comprising an operational head, e.g. a patient tube circuit, configured for connecting the ventilator to the patient. The ventilator operational head is installed/removed from the ventilator via a first reversible connector. The first therapeutic device also comprises a memory device with control instructions for controlling the ventilator. This operational head delivers the pressurized air to the patient, and the controller controls patient pressure, e.g. reduces the patient pressure when appropriate, according to the control instructions. The Operational Head also includes a pressure sensor that senses the pressure at the point of treatment.

The memory device of the first therapeutic device is reversibly connected to the controller, such as by a wireless connection (not shown) or a wired connection (e.g. through the first reversible connector as depicted in FIG. 9). This memory device optionally comprises specific treatment parameters and algorithms which are suitable for use with the patient tube circuit or other operational head of the first therapeutic device. Optionally, the memory device comprises one or more calibration parameters such as tube resistance, pressure sensor calibration, and sterilization expiration date. Software updates (e.g. complete or partial) for the ventilator controller may also be contained in the memory device. Optionally, the control instructions include pressure parameters or specifications and the controller receives pressure feedback from the pressure sensor and controls the ventilator in accordance with the pressure parameters or specifications of the control instructions, e.g. control the pressure at the point of treatment.

Used in conjunction with the ventilator can be a vaporizer. A second console comprising a controller and vaporizer is provided. This vaporizer is optionally a nebulizer (e.g. which vaporizes or atomizes medications to allow them to be consumed via inhalation) or a humidifier (e.g. which vaporizes water, or saline-containing water, to control the humidity of the air delivered to the patient). A second therapeutic device comprising a vaporizer operational head and a memory device reversibly connected to the second console. The vaporizer operational head is configured to connect the vaporizer to the patient, e.g. comprises a face-mask, is comingled with the operational head (e.g. patient tube circuit) of the ventilator (e.g. the vaporizer operational head comprises an inlet to the operational head of the ventilator), or is configured for use in combination with non-intelligent-connector ventilators.

The memory device of the second therapeutic device is reversibly connected to the controller, such as by a wireless connection (not shown) or a wired connection (e.g. through the first reversible connector as depicted in FIG. 9). The memory device comprises control instructions for controlling the vaporizer. Optionally, the control instructions comprise parameters specific to the vaporizer, such as flow rates, treatment intervals, dosages, or calibration parameters. Optionally, the control instructions comprise one or more treatment algorithms (e.g. instructions for periodic or conditional delivery of vapor). Optionally, the memory device comprises software updates (e.g. complete or partial) for the vaporizer controller, an optional vaporizer UI, or both.

The system can comprise a communications link connecting the ventilator console and the console of the vaporizer. This link is optionally any wired or wireless data link. Examples include USB, Bluetooth, Firewire, Ethernet, RS-232, RS-485, and WiFi. A communications link provides, e.g. a system of coordinated therapies.

Optionally, the memory device of the ventilator therapeutic device comprises control instructions (e.g. parameters, algorithms or software) for the vaporizer controller. Optionally, the memory device of the vaporizer therapeutic device comprises control instructions (e.g. parameters, algorithms or software) for the ventilator controller.

One or both of the consoles optionally comprises a connection for a user input device such as a keyboard. Optionally, the system is configured to allow user input and/or user output (e.g. display) of both systems using a single user input device and/or user output device, respectively. One or both consoles may further comprise a connection to a data network, such as the Internet, for conveyance of data between the manufacturers and the health care provider.

With such a system, many advantages can optionally now be provided. For example:
- Therapies requiring new combinations of therapeutic devices or operational heads may be created without first updating all deployed consoles.
- The provided therapy can be selected or modified by whichever memory device contains the most-recent therapy information for the combination of operational heads detected at the point of treatment.
- Software for both devices (or first and second therapeutic devices) may be updated as specified by the most-recently manufactured therapeutic device or operational head thereof.
- Delivery of therapy is prevented where an inappropriate combination of devices or operational heads thereof detected.
- Data from the procedure may be stored in one or both of the first and second memory devices—allowing one or more parties to perform post-procedure performance review.
- Consoles may be connected in the field to provide integrated therapies not contained within their original programming.
- Consoles may be combined and separated as required for particular installations and situations.

Therapies requiring new combinations of operational heads may be created without first updating all deployed consoles.

Example 17 Therapeutic System

In this example, a system is provided as detailed in Example 16, with the exception that only one of the therapeutic devices comprises a memory device with reversible operable linkage to its respective console. A communications link is provided between the first console and the second console. Through the communications link, the console with the reversibly linked memory device recognizes the other console or therapeutic device attached thereto and provides control instructions to the other console to control its energy generator (e.g. where control instructions for the other console are generic or understood)

As one example, the reversibly linked memory device comprises instructions for controlling both consoles. As another example, the console with the reversibly linked memory device can comprise its own memory device (e.g. hard drive) comprising instructions for controlling the other console, e.g. instructions that are dependent on the control instructions provided by the reversibly linked memory device.

In this example, memory device of a single therapeutic device can be used to control therapy from a plurality of consoles.

Example 18 Therapeutic System

Figure 10:
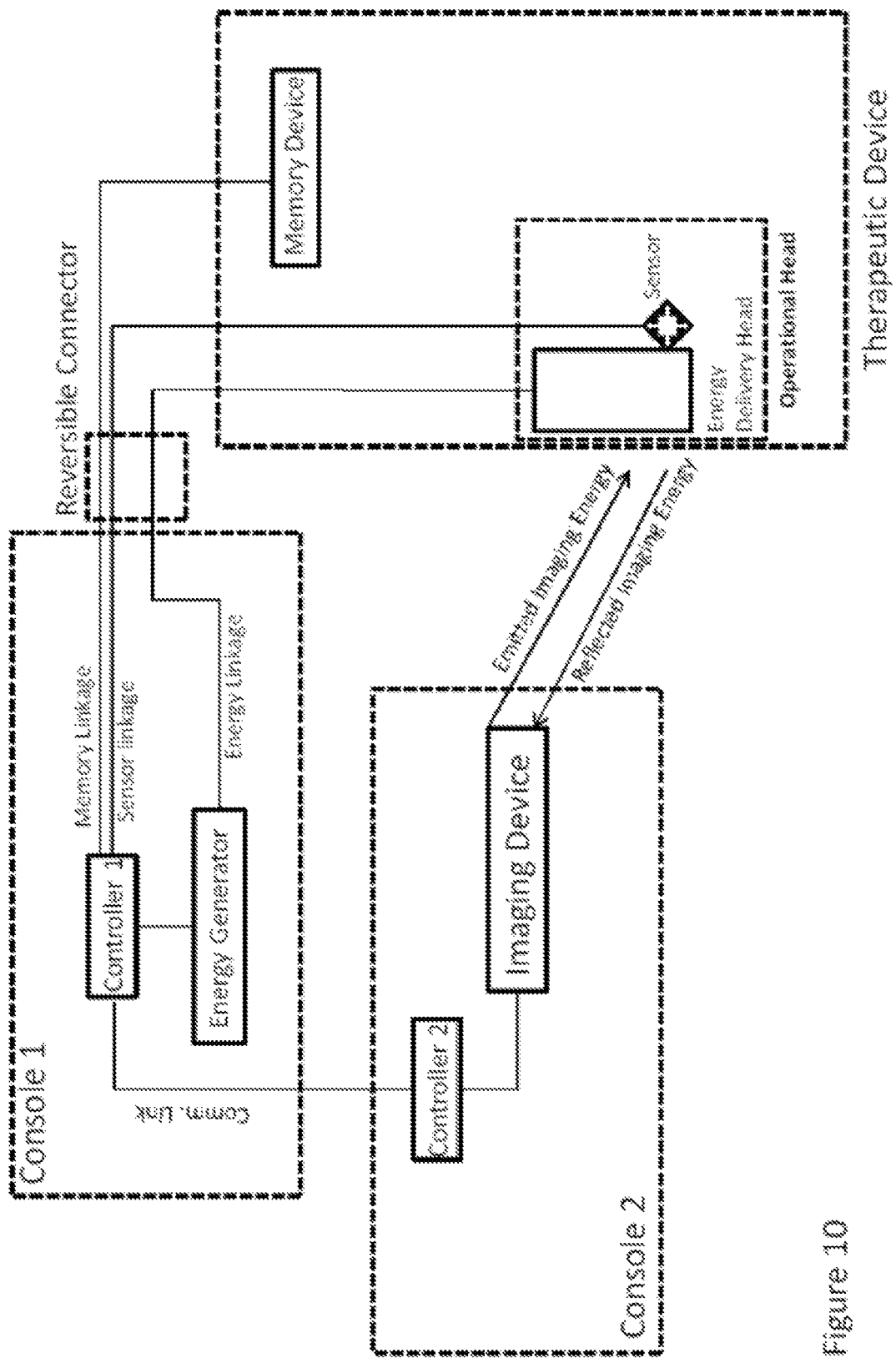
FIG. 10 depicts an examplary system of the present invention.

A system of the invention is provided. The system comprises a first console comprising a controller and an energy generator, and a therapeutic device and memory reversibly connected to the first console. The system further comprises a second console connected to the first console by a communications link. The second console comprises a controller and a diagnostic device connected to the controller. As example of such a system is depicted in FIG. 10.

As one example, the first console provides therapeutic energy (e.g. microwave or RF generator) while the second console provides imaging such as visualization, navigation, or other diagnostic functions e.g. CAT, PET, MRI, X-ray, or fluoroscopy. The first console comprises a controller connected to an energy generator which is reversibly connected to a therapeutic device comprising an ablation (e.g. microwave ablation) head or other energy delivery head as an operational head. The controller of the first console is reversibly connected to a memory device of the therapeutic device (e.g. in an optional plug thereof). The second console comprises a controller connected to a diagnostic device, e.g. that transmits and/or detects imaging energy. The first console and second console are connected by a communications link configured to transmit data between the console controllers.

Using the examplary system set forth above, therapeutic energy such as energy in the microwave band can be used, e.g. to treat tumors in lung liver, kidney, bone and other biological tissues or organs. Such a system can additionally or alternatively be used to create lesions along specific nerves or groups of nerves. Although the example above specifies microwave as the ablation energy, the invention also contemplates the use of any therapeutic or ablation energy. For example, an energy generator can be a generator of any of the following energies: radio frequency energy, ultrasound energy, laser energy, cryoablation energy, plasma energy, electroporation energy, and high intensity focused ultrasound (HIFU) energy. Optionally, energy is delivered directly or in an interferential mode, the former which optionally selectively ablates tissue by combining the energy of two sources in a constructive manner at the desired point of ablation and reduces or eliminates ablation at other locations through destructive interference.

Target biological tissue for ablation therapy can be selected, e.g. to block the conduction of sensor, motor, or combination nerve bundles to prevent either the sensory or motor functions associated with those nerves. Optionally, the therapy comprises sensory blockage, e.g. used for pain management applications or to affect the modulation of other body functions, such as in renal denervation (e.g. where the disruption of nerves associated with the renal system along the renal artery are ablated to cause a reduction in arterial blood pressure). Optionally, the system is used to ablate vascular and pulmonary structures for the treatment of, e.g. asthma or COPD.

Optionally, such a system comprising a therapeutic device and an imaging device is used in therapeutic procedures where direct observation of the ablation by the physician is not possible. Such a system can be used to provide modeling, predictive calculations, visualization systems, and other indirect feedback (e.g. in the form of temperature and impedance readings) to provide the physician with the information required to complete the procedure.

To provide efficacious treatment and accurate information to the physician through these indirect sensors it is useful for the parameters of the energy delivery and sensory devices to be known. Such parameters, such as size, distances, surface areas, impedances, calibration and correction factors, coupling factors, frequency-specific characterizations, resonant frequencies, opacity, among others, vary from device to device due to manufacturing processes and tolerances. In interferential treatments parameters of this type are particularly important because energy of various frequencies and wavelengths must be precisely applied, the calculation of which requires accurate spatial information concerning the separation of two or more points of energy application as well as characterization of the electromagnetic coupling of the energy to the patient. In this embodiment this unique information can be stored within the memory device of the therapeutic device. These parameters allow the predictive algorithms within the energy generator console to accurately deliver the energy required to obtain the predicted ablation results. The parameters can also be communicated to the Imaging console via the communications link where they are used, e.g. to improve the accuracy of the information provided to physician, as well as in any predictive calculations which this system may provide. For example, the energy generator console can send information to the visualization console such as the size, mass, or volume of an electrode on the therapeutic head so that the visualization system can incorporate these into the calculations of lesion size, shape, and/or position. As another example, the energy delivery console can send information such as antenna coupling coefficient(s), e.g. so that the visualization system can predict the amount of energy absorbed by the tissue vs. the amount transmitted so as to predict lesion size, shape, and/or position. As another example, the energy delivery console can send information such as distance and orientation between multiple electrodes (antenna), e.g. so as to predict the effects of the combination of energy from these multiple electrodes on the size, shape, and/or position of the lesion.

Optionally, the imaging console sends data to the energy generator console, e.g. spatial and tissue characterization information back to the energy delivery system. In this example, the energy generator console optionally uses this data in combination with the unique parameters of the energy delivery head to control the energy generator, e.g. by adjusting treatment energies and/or selecting or modifying predictive algorithms appropriately.

The reversibly connected memory device comprises control instructions for controlling the energy generator. Optionally, the control instructions comprise instructions for receiving feedback or other data from the second controller (i.e. the imaging device) and selecting or modifying algorithms or parameters. Optionally, the control instructions comprise algorithms (e.g. general algorithm methods), use data or reuse data, authentication information, system coordination information for the energy generator console and the imaging console, as well as software updates for one or both of the consoles.

With such as system, many advantages can optionally now be provided. For example:
  Unique, accurate and consistent information regarding the parameters of the Operational Head can be provided to multiple consoles in the system.
  Parameters specific to the ablation of tissue and nerves by various energy modalities may be stored in the memory device of the reversibly connected therapeutic device.

Example 19 Therapeutic System with an Intermediate Device

One embodiment of the invention provides a system comprising a console and reversibly connected therapeutic device with a memory device, wherein the system further comprises an intermediate device configured to provide an extension (e.g. greater than any of: 30 cm, 60 cm, 90 cm, 120 cm, or 150 cm) between the therapeutic device and the console, e.g. as depicted in FIG. 11. Optionally, the intermediate device and the therapeutic device each comprise an independent memory device comprising control instructions specific to their respective device.

Optionally, the memory devices of both the intermediate device and the therapeutic device comprise parameters or other instructions associated with their respective device (e.g. software, capabilities, impedance, loss factors, or frequency characterization). These parameters can be used, e.g. by the controller to provide a safe and efficacious treatment.

Optionally, the memory devices of one or both of the intermediate device and the therapeutic device comprise one or more instructions selected from recommend number of uses, authentication and re-use prevention rules, and sterilization validity information.

Optionally, a plurality of therapeutic devices and/or a plurality of intermediate devices are provided that can alternatively be combined to form a system. With this embodiment, different intermediate device/therapeutic device combination can produce different systems, each with their own capabilities and uses.

Such a system allows, e.g. for situations in which the intermediate device and the therapeutic device, or memory devices thereof have different production dates. For example, therapeutic devices or intermediate devices may have been produced at different times with different ideal combinations of software and parameters specified for the treatment procedure. Optionally, data stored on at least one of the devices (e.g. newest device) to provide updates or information that allows the controller to control the energy generator in accordance with the given combination of therapeutic device and intermediate device.

In this example, the system comprises an intermediate device comprising an extension (e.g. cable) reversibly connected on one end to the console and reversibly connected on another end to the therapeutic device. The intermediate device is configured in any manner that provided an operable linkage to connect the energy generator and the therapeutic device. Optionally, the intermediate device further comprises an operable linkage for the memory device of the therapeutic device. Optionally, the intermediate device further comprises a memory device. The intermediate device can be configured, e.g. as a separable cable, enabling a physician to span a substantial distance between the console and the therapeutic device. This configuration can allow, for example, an intermediate device to be provided as a reusable extension that is not sterilized between reuse while the therapeutic device is sterilized between reuse. As another example, this configuration can also provide systems in which the therapeutic device is a single-use device, but the cable may be re-used. This can substantially reduce expense of materials when lengthy cabling is needed to connect the console to the operational head. A system comprising an intermediate device can also be implemented, e.g. where different lengths of cables are appropriate for different situations or therapeutic procedures.

Although the example detailed above provides a single intermediate device, a system can optionally comprise a plurality of intermediate devices, each serially reversibly connected to the next, with the console at one end, and the therapeutic device at the other end. Optionally, each intermediate device comprises its own memory device.

Optionally, the system comprises configuration management software. Such software can be configured to allow the controller to receive, interpret, and/or implement control instructions or other data from a plurality of simultaneously connected memory devices of respective reversibly connected devices. Such software is optionally configured for conflict resolution between control instructions provided on respective memory devices of a therapeutic device and an intermediate device. Optionally, the configuration management software is configured to identify an inconsistent or incoherent combination of two or more sets of control instructions provided by respective memory devices and provide a set of control instructions for a therapeutic procedure (e.g. by selecting a set of control instructions from one of the memory devices or producing a set of control instructions by selecting portions of the control instructions provided on two or more memory devices). For example, combinations of devices into a system may cause conflicts where the parameters or other instructions stored within the memory device of the therapeutic device is inconsistent or incoherent with parameters or other instructions stored in the memory device of the intermediate device (or other devices of a serially connected chain). Examples of inconsistent or incoherent combinations of control instructions that can be identified by the configuration management software include a) two memory devices, each containing a software update for one or more consoles which are different from the other; b) two memory devices, each containing settings or treatment algorithms which are different from the other; c) a memory device which contains settings, and a console which also contains setting for that device which are different from each other; d) a memory device which contains software for the console, attached to a console which already contains a newer software release; e) a memory device whose settings specify use with a set of accessories/console(s) connected to a console which specifies that device for use with another set of accessories/console(s); f)

two memory devices containing software with a different version (e.g. mismatched software revisions or dates); g) two memory devices wherein at least one of the memory devices contains a list of compatible d/t devices (or consoles) that does not include the d/t device (or console) associated with other memory device (e.g. an "unexpected device"); h) two memory devices wherein at least one of the memory devices contains a list of incompatible d/t devices that includes the d/t device associated with other memory device; i) incompatible equipment combinations of therapeutic or diagnostic devices; or j) Software or hardware versions of part of the system not known to be compatible with the device or other parts of the system.

This conflict resolution function of the configuration management software is optionally configured perform steps of collecting data (e.g. control instructions, identifiers, parameters, algorithms) from a memory device of each chained device and making a determination of the most-appropriate combination of software, parameters, and/or algorithms to use during patient treatment. This can be done, e.g. to ensure that the most-recent and most-appropriate treatment is provided. Examples of determinations that can be made include a) the selection of the target temperature when the memory device of a therapeutic device and a memory device of the console each contain control instructions specifying a different temperatures (e.g. the conflict resolution software can be configured to select the target temperature provided by the memory device of the therapeutic device); b the selection of a software version when the memory of the therapeutic device contains a different software version than a memory device of the console (e.g. software is configured to select the software provided by the therapeutic device memory, e.g. downgrading if the console memory contains a more recent software version than the therapeutic device memory; or c) a therapeutic device memory comprises instructions for operation of a particular secondary device (e.g. a cooling pump) but the console detects that a different secondary device is connected (e.g. a different cooling pump) and the console memory device contains control instructions such as business rules for said different secondary device, then, e.g. the conflict resolution software can select the appropriate control instructions for the connected secondary device, resulting in effective treatment being performed using the different secondary device.

In order to provide the configuration management software with the information that can be used to determine this optimal configuration, sets of business and clinical rules are embedded in one or several of the memory devices. Some examples of the rules which may be included are:
1. identifications of combinations of other devices are compatible with a particular device.
2. identifications of which software is compatible with device combinations
3. instructions for selecting a software version from one of the memory devices (reversibly or non-reversibly connected memory devices), e.g. instructions downgrade system software or to utilize newer software provided by a reversibly connected memory device when a console's memory device (e.g. non-reversibly connected) contains more-recent software or information than that specified by any currently connected device
4. override rules, e.g. when instructions on a reversibly connected memory device indicates that its respective therapeutic device or intermediate device chain has use limitations (e.g. an override rule that specifies whether treatment can proceed if a device has met or exceeded its use or re-use limit
5. error-processing rules, e.g. when memory is not present in a reversibly connected device, or cannot be read, the error-processing rule specifies if treatment can proceed.
6. data-write rules, e.g. specifies which memory device, or devices, if any should be written with data or feedback from the current procedure?
7. display rules, e.g. specifies the information should be displayed to the operator for a unique combination of devices With such as system, many advantages can now optionally be provided. For example:
- devices within a system may be separable to reduce cost or increase functionality which retaining the benefits of earlier embodiments.
- authenticity (e.g. anti-counterfeiting) may be enforced on all devices in the system.
- software and treatment updates may be introduced into the system by the most-recently manufactured portion of the system rather than a particular portion of the system.
- portions of the system of devices may not include unique memory devices at the discretion of the manufacturer, for example, the therapeutic device may not contain its own memory device in order to reduce cost but the separable cable, due to a less-frequent replacement cycle, may incorporate a memory device with control instructions for use with a therapeutic device.
- energy delivery consoles may provide connectors of different size and configuration than the therapeutic device. For example, the intermediate device (e.g. separable cable) can provide the physical translation of connections and the memory device within the intermediate device provides the logical and clinical translation for using a particular therapeutic device with the console.

Example 20 Treatment Algorithm

A system of the invention is provided comprising an ablation energy generator and a therapeutic device with an energy delivery head comprising electrodes (e.g. RF electrode). The system comprises a treatment algorithm, for example, stored on a console memory device or the therapeutic device memory.

The treatment algorithm is configured to deliver therapeutic energy (e.g. RF ablation energy) and comprises a plurality of steps:
1. Detect the connected device and retrieve parameters or other data from the therapeutic device memory (e.g. which may provide the settings used, or represent the entirety the algorithm steps below)
2. Delay until conditions are simultaneously met, e.g. each of:
   a. The impedance between two electrodes is within an allowable range (e.g. 50 to 300 ohms)
   b. The temperature at the electrodes is within an allowable range (say 35 to 41 C)
   c. The 'energy activation' button is pressed.
3. Begin energy delivery, e.g. starting at a first power (e.g. 0.0 W) and increasing (e.g. linearly) power (e.g. 10.0 W over 30 seconds). Optionally
   a. If the impedance exceeds a limit (e.g. 300 ohms) stop treatment
   b. If the temperature exceeds a limit (e.g. 80° C.) stop treatment
4. Apply up to given power limit (e.g. 10 W) to achieve and maintain a target temperature (e.g. 85° C.). Optionally, a. After 30 seconds stop treatment
b. If more than 200 Joules are delivered stop treatment
c. If the impedance exceeds 400 ohms stop treatment Example 21 Control Algorithm A system of the invention is provided comprising an irrigation energy generator (e.g. peristaltic pump) and a therapeutic device with an irrigation head. The system comprises a control algorithm, for example, stored on a console memory device or the therapeutic device memory.

The control algorithm is configured to deliver fluid flow or other irrigation by controlling the following steps:
1. Detect the connected device and retrieve parameters or other data from the therapeutic device memory (which may inform the controller of the settings, parameters, or the entirety, of the algorithm below).
   a. Retrieve the energy output parameter of 'flow rate'. By example, the memory device includes a plurality of flow rate settings that may adjusted by the operator within a specified range (e.g. of either 10, 15, 20, 25, or 30 ml/min).
2. The operator (i.e. user) is queried to select the flow rate from these choices
3. The operator selects a flow rate (e.g. 20 ml/min)
4. The operator actuates the control to begin cooling fluid flow
5. The controller retrieves information from its internal Calibration Parameters that a pump speed sensor will report an increase in its value (e.g. 1.0V for every 24.8 roller-strokes per minute).
6. The controller retrieves Internal Calibration Parameters from a console memory device that describe the fluid pump characteristics (e.g. indicating that each roller-stroke produces 32.8 mm of linear displacement)
7. The controller retrieves calibration parameters from the therapeutic device that indicate the inner diameter of the irrigation tubing (e.g. 2.04 mm).
8. The controller uses the parameters to compute the voltage value which the sensor will report when the selected flow rate (e.g. 20.0 ml/min) is being delivered. This is the target value the controller will attempt to maintain.
9. The controller reads a pump speed sensor and compares this to the target value.
10. According to a control law, such as a Proportional, Integral, and Derivative (PID) control loop. The gains of the parameters in the control loop may be fixed, specified by internal calibration parameters within the console, or specified by a set of calibration parameters within the therapeutic device memory to achieve the correct therapeutic outcome.
11. The controller continues to perform steps 10 and 11 periodically to maintain the desired flow until the operator de-activates flow, or an error or anomaly occur.

Example 22 Predictive Algorithm

A system of the invention is provided comprising an ablation energy (e.g. RF) generator and a therapeutic device with an energy delivery head comprising. The system comprises a predictive algorithm, for example, stored on a console memory device or the therapeutic device memory.

As one example, the predictive algorithm is configured to make a lesion prediction using the following steps:
1. Detect the connected therapeutic device and retrieve parameters or other data from memory device (which may inform the settings, parameters, or the entirety, of the algorithm below)
2. Operator selects the size of lesion to create
3. Delay until all of the conditions are simultaneously met, e.g.:
   a. The impedance between two electrodes is within an allowable range (e.g. 50 to 300 ohms)
   b. The temperature at the electrodes is within an allowable range (e.g. 35 to 41° C.)
   c. The 'energy activation' toggle button is pressed.
4. Controller monitors the time, impedance, temperature, and energy delivered and makes a prediction of the lesion size based on a computerized model. The model may, for example, be based on the heat equation of a specific volume of tissue, perfused at a certain blood flow rate, at a certain depth of probe insertion.
5. Controller halts the treatment if a limit (e.g. boundary condition) is violated (e.g. maximum or minimum impedance reached), or when predicted lesion size reaches that specified by the operator.

As another example, the predictive algorithm is configured to make a lesion adaptive prediction using the following steps:
1. Detect the connected therapeutic device and retrieve parameters or other data from the therapeutic device memory (which may inform the settings, parameters, or the entirety of the algorithm below)
2. Operator selects the size of lesion to create
3. Delay until all of the following conditions are simultaneously met, e.g.:
   a. The impedance between two electrodes is within an allowable range (e.g. 50 to 300 ohms)
   b. The temperature at the electrodes is within an allowable range (e.g. 35 to 41C)
   c. The 'energy activation' button is pressed.
4. Controlling computer monitors the time, impedance, temperature, and energy delivered and makes a prediction of the lesion size based on a computerized model of the laws of nature. The model may, for example, be based on the heat equation of a specific volume of tissue, perfused at a certain blood flow rate, at a certain depth of probe insertion. Such a model may be an explicit closed solution, or may be approximated by finite-element solutions. Based on the combination of the monitored parameters the (time, temperature, energy delivered, impedance) the computer modifies its model, or model parameters, or the system. Such adaptive control and parameter estimation algorithms are known in the art, (i.e. Least Squares, or those proposed by Lillacci, PLoS Comput Biol. 2010 Mar. 5; 6(3):e1000696. doi: 10.1371/journal.pcbi.1000696. Parameter estimation and model selection in computational biology. Lillacci G, Khammash M. Center for Control, Dynamical Systems and Computation, University of California at Santa Barbara, Santa Barbara, Calif., United States of America. or Slotine "Applied Nonlinear Control" (Slotine and Li, Prentice-Hall, 1991))
5. The updated model or parameters are then used to more accurately predict the lesion size.
6. Controller halts the treatment if a boundary condition is violated (i.e. maximum or minimum impedance reached), or when predicted lesion size reaches that specified by the operator.

Example 23 System Comprising Parameters

A system of the invention is provided comprising a first console having a first energy generator and a first therapeutic device comprising a memory device and a first energy delivery head configured for transmitting the first energy.

The first energy generator is selected from a wave energy generator, a pneumatic energy generator, a vaporizer, a plasma energy generator, a cryoablation energy generator, an irrigation energy generator (e.g. fluid pump), and an electroporation energy generator. The first therapeutic device and first therapeutic device memory are reversibly attached to the console, e.g. by a first reversible connector. Optionally, the system comprises a user interface device (UI) such as a display. Optionally, the system comprises one or more sensors. Optionally, the system further comprises one or more secondary devices reversibly attached to the console such as an imaging device, an intermediate device, a second therapeutic device, and/or a second console comprising a second energy generator. Optionally, the one or more secondary devices comprise respective memory devices.

The first therapeutic device memory comprises one or more parameters selected from (e.g. each of) therapeutic energy output parameters (e.g. of the first energy generator and/or optional second energy generator), UI output parameters, calibration parameters, verification parameters, and capability parameters. The optional calibration parameters, verification parameters, and capability parameters describe the therapeutic device or hardware thereof (e.g. an energy delivery head). Optionally, the memory device comprises one or more alternatively selectable parameter settings (e.g. as listed under 'device settings').

The optional memory device of the optional secondary device comprises one or more parameters selected from (e.g. each of) therapeutic energy output parameters (e.g. of the first energy generator and/or second energy generator), UI output parameters, calibration parameters, verification parameters, and capability parameters. The optional calibration parameters, verification parameters, and capability parameters describe the secondary device or hardware thereof (e.g. an energy delivery head or sensor). Optionally, the memory device comprises one or more alternatively selectable parameter settings (e.g. as listed under 'device settings').

At least the first console comprises a local memory device comprising system software (e.g. operating system and/or framework) configured to cause the console controller to obtain the parameters from the reversibly connected memory devices. The local memory device of the first console also one or more algorithms (e.g. treatment algorithms, control algorithms, and/or predictive algorithms) that reference the parameters, e.g. as independent variables of equations or treatment steps. Additionally or alternatively, the reversibly connected memory device(s) comprise algorithms that are obtained by the console controller.

Selection of the parameters stored on respective reversibly connected memory devices is made from the following parameter list, which provides categories of useful parameters, and specific examples thereof. The skilled artisan will immediately recognize that the selection of parameters is based, in part, on the selection of energy generator(s), therapeutic device(s), and/or secondary device(s).

Parameter List
Therapeutic Energy output parameters
  Wave energy output parameters
    electromagnetic wave output (e.g. RF or microwave) parameters
      voltage, current, temperature, duty-cycle, pulse rate, pulse duration, pulse shape, ramp time, treatment time, joules delivered, frequency, waveshape, power, phase, and channel used,
    sonic energy output (e.g. ultrasound or HIFU) parameters
      Beam intensity, beam phase, power, frequency, channels used, duty cycle, current, voltage, pulse rate, pulse duration, pulse shape, ramp time, treatment time, waveshape, phase, joules delivered.
    laser energy output parameters
      Average power, peak power, beam intensity, beam size, voltage, current, duty-cycle, pulse rate, pulse duration, pulse shape, ramp time, treatment time, phase, joules delivered, channels used
    Nerve stimulation energy output parameters
      stimulation rate, waveshape, current, voltage, pulse rate, pulse duration, pulse shape, ramp time, treatment time, frequency, phase, power, channel used.
  Mechanical Energy output parameters
    Irrigation output parameters
      Flow rate, pressure, pump speed, pump torque, flow shape, ramp time, duration, volume delivered
  Plasma energy output parameters
    gas flow rate, power, voltage, initiation output level, duty cycle, pulse rate, pulse duration, pulse shape, ramp time, treatment time, joules delivered, channels
  Cryoablation output parameters
    Coolant flow, thermoelectric power, thermoelectric current, coolant pressure, pulse frequency, pulse duty cycle, ramp rate, treatment time.
  Electroporation parameters
    Voltage, charge, pulse rate, pulse width, joules, number of pulses, treatment duration.
UI output (e.g. display) parameters
  Notification parameters
    Data displayed
      Screens
      triggers, and ranges of acceptable values
      All other parameters taught herein
    warning, alerts, alarms
  display parameters
    text size, graph axes, update rate, filtering, color, units of values, precision of values,
Capability parameters
  compatible or incompatible modes of operation, compatible or incompatible therapeutic devices, compatible or incompatible consoles or energy generators
Verification parameters
  use data; recommend number of uses; model number; company/brand; Produced for; Production Plant; time or date of production; maximum number of uses allowed; authentication (e.g. key) of a local device (e.g. authentication of a therapeutic device provided on therapeutic device memory); authentication of a remote device (e.g. authentication of an intermediate device provided on therapeutic device memory); re-use prevention rules; sterilization validity information; sterilization expiration date; device serial number; device authorized for use for this system; device authorized for use in the country or geography in which this system was sold; device authorized for use with this system based on systems owner; device authorized for use with this system based on system's brand name; device authorized for use with this system based on feature set; device authorized for use with this system based on the total number of treatments authorized for this system; device authorized for use with this system based on the re-use history of this device; authentication keys of data stored on the memory device, e.g. software updates encrypted with symmetric (single key) or asymmetric (public/private) methods, the validity of which must be confirmed before the system will provide therapy, authentication keys encrypted with symmetric (single key) or asymmetric (public/private) methods, the validity of which must be confirmed before the system will provide therapy; authentication Keys for or memory device data such as parameters encrypted with symmetric (single key) or asymmetric (public/private key) methods, the validity of which must be confirmed before the system will provide therapy Calibration parameters
    Energy delivery head calibration parameters
        wave energy delivery head (e.g. RF electrode) parameters
            calibration parameters for energy delivery
                loss factors, impedances, including for example R-L-C values, Z and Phase, complex Z and S parameters, surface area, maximum energy allowed, diameter, energy coupling factors, physical lengths (needles, tips, probes, cables), electrode exposure lengths, distance between electrodes, impedances between electrodes, impedance between channels or wiring leads, resonant frequencies, thermal impedance, thermal time constant, temperature feedback gains, offsets, and characteristic equations, cooling flow rates,
            calibration parameters (e.g. electrode parameters) for imaging
                length, area, mass, orientation, volume, opacity, or antenna coupling coefficient of the first energy delivery head)
        pneumatic pressure head and/or vaporizer head (e.g. ventilator or vaporizer head such as patient tube) parameters
            tube resistance, tube diameter, tube volume, tube length, pressure vs. flow characteristic equation parameters, vaporizer output characteristic equations, leak rate, O2 Perfusion sensor characterization curves, O2 sensor gains/offsets/characteristic equation parameters,
        Irrigation head (e.g. irrigation catheter) parameters
            tube diameter, tube volume, tube length, maximum pressure allowed, maximum flow rate allowed, pressure vs. flow characteristic equation parameters, recommended flow rate, balloon volume, flow vs. cooling characteristic equation parameters, electrode size, pressure measurement characteristic equation parameters,
    Intermediate device calibration parameters
        Impedance, Loss factors, Frequency characterization, Length, Contact impedance, Temperature measurement characteristic equation parameters, Pressure measurement characteristic equation parameters, Inter-signal impedances
    Sensor calibration parameters
        pressure sensor parameters
        temperature sensor parameters Input parameters (e.g. monitored value provided as a trigger value, target value, or value limit, or derived values used to control treatment)
    an environmental condition
        Therapeutic- or side-effect of treatment
            air pressure, temperature, chemical composition
    biological condition or physiologic condition
        Therapeutic- or side-effect of treatment
            ECG, EEG, EMG, or EOG, heart rate, respiration, Oxygen saturation Level, Carbon dioxide saturation level, De-oxygenated hemoglobin level, Blood pressure, Breath rate, Blood flow, Muscle contraction
    therapeutic device condition
        contact force or pressure, temperature, acceleration, impedance, phase, volume, position, disconnection, flow rate, chemical composition, rate of change of impedance, rate of change of temperature, rate of change in pressures, change in power required to maintain temperature, change in power required to maintain impedance, change in power required to maintain pressure, change in power required to maintain flow
    image parameter
        image contrast (e.g. monitored image contrast to trigger delivery of additional contrast agent), radiological marker movement, radiological marker position
    user input status (e.g. toggle switch)
    monitored energy output parameters Device Settings
    Energy delivery head calibration parameters
        wave energy delivery head (e.g. RF electrode), Treatment Temperature, Treatment Time, Power, Voltage, Stim amplitude, Stim rates, Stim pulse width, Electrodes to energize, Fluid Flow rate, Duration of treatment, Joules to deliver, Size of lesion, Shape of lesion, Joules to absorb (cooling), Maximum voltage, Maximum flow rate, Minimum Flow rate, Channels to use, Type of procedure, Anatomy targeted, Data output formats, Audible volumes
    pneumatic pressure head and/or vaporizer head (e.g. ventilator or vaporizer head such as patient tube)
        fluid flow rate, fluid volume to deliver, humidification level, Pneumatic flow rate, Pneumatic pressure, Patient type (adult/pediatric, weight, age, gender), Breath Modes allowed, Breath rates allowed, Tidal volumes allowed, Spontaneous breath intervals allowed, Breath rate alarms, Breath tidal volume alarms, Forced-breath timeout, Breath Mode parameters, Intra-cycle pressures (i.e. PIP), Inter-cycle pressures (i.e. PEEP), Target oxygen perfusion, Vascular support pressures, Vascular support pressure gradients, Vascular compression rates
    Irrigation head (e.g. irrigation catheter)
        tube diameter, Volume to inject, Contrast agent flow rate, Pressure to maintain, Maximum pressure to allow, Allowable leakage rate, Bubble detection sensitivity, Fluid pre-heat/cool temperature The citations provided herein are hereby incorporated by reference for the cited subject matter.

What is claimed is:

1. A system comprising:
    a. a console, wherein the console comprises an energy generator and a controller, wherein the controller is configured for controlling the energy output of the energy generator;
    b. a therapeutic device comprising:
        i. an operational head configured for transmitting the energy output to a target site; and
        ii. a first memory device, housed by the therapeutic device, comprising control instructions, wherein the control instructions comprise:
            1. energy control instructions for said controlling the energy output;
            2. one or more calibration parameters of the therapeutic device;

3. one or more verification parameters of the therapeutic device; or
4. one or more capability parameters of the therapeutic device;

c. an intermediate device configured for transmitting the energy output from the console to the therapeutic device;

d. a first reversible connector, positioned between the therapeutic device and the intermediate device, and configured for operably linking the energy generator to the intermediate device;

e. a second reversible connector, positioned between the intermediate device and the console, and configured for operably linking the intermediate device to the operational head of the therapeutic device;

d. a reversible memory operable linkage configured for operably linking the first memory device to the controller;

wherein:

the intermediate device comprises a second memory device, housed by the intermediate device, comprising control instructions for controlling the intermediate device, the therapeutic device, or both, wherein the second memory device is reversibly linked to the controller;

the first reversible connector comprises a first interacting coupler and a second interacting coupler that connect to each other in a jack/plug configuration, wherein the first interacting coupler is comprised by the intermediate device and the second interacting coupler is comprised by the therapeutic device;

the second reversible connector comprises a third interacting coupler and a fourth interacting coupler that connect to each other in a jack/plug configuration, wherein the third interacting coupler is comprised by the intermediate device and the fourth interacting coupler is comprised by the console; and the first reversible connector and the second reversible connector are configured such that, when the first interacting coupler and the second interacting coupler of the first reversible connector are connected to each other and the third interacting coupler and the fourth interacting coupler of the second reversible connector are connected to each other, the energy generator is operably linked, through the intermediate device, to the operational head of the therapeutic device.

2. The system of claim 1, wherein the second memory device comprises one or more calibration parameters corresponding to hardware of the intermediate device, wherein the one or more calibration parameters are selected from the group consisting of impedance, loss factors, frequency characterization, length, contact impedance, temperature measurement characteristic equation parameters, pressure measurement characteristic equation parameters, and inter-signal impedances, and wherein the one or more calibration parameters are used by the controller to control the energy generator for generating energy according to the one or more calibration parameters.

3. The system of claim 1, wherein the second memory device comprises calibration parameters of the intermediate device or capability parameters of the intermediate device, wherein the calibration parameters or the capability parameters are used by the controller to control the energy generation according to the calibration parameters of the intermediate device or the capability parameters of the intermediate device.

* * * * *